US011446043B2

(12) United States Patent
Patrinicola et al.

(10) Patent No.: US 11,446,043 B2
(45) Date of Patent: Sep. 20, 2022

(54) MIS CROSS-CONNECTOR

(71) Applicant: GLOBUS MEDICAL, INC., Audubon, PA (US)

(72) Inventors: Angelo Patrinicola, Audubon, NJ (US); Edward Karpowicz, Sewell, NJ (US)

(73) Assignee: Globus Medical, Inc., Audubon, PA (US)

( * ) Notice: Subject to any disclaimer, the term of this patent is extended or adjusted under 35 U.S.C. 154(b) by 385 days.

(21) Appl. No.: 16/513,994

(22) Filed: Jul. 17, 2019

(65) Prior Publication Data

US 2019/0357923 A1    Nov. 28, 2019

Related U.S. Application Data

(63) Continuation of application No. 15/226,011, filed on Aug. 2, 2016, now Pat. No. 10,398,454, which is a continuation-in-part of application No. 14/936,071, filed on Nov. 9, 2015, now Pat. No. 10,335,205.

(51) Int. Cl.
*A61B 17/16* (2006.01)
*A61B 17/70* (2006.01)

(52) U.S. Cl.
CPC ...... *A61B 17/1671* (2013.01); *A61B 17/7043* (2013.01); *A61B 17/7052* (2013.01); *A61B 17/7079* (2013.01); *A61B 17/7083* (2013.01)

(58) Field of Classification Search
CPC .................................... A61B 17/7049–7052
USPC ................................................ 606/250–279
See application file for complete search history.

(56) References Cited

U.S. PATENT DOCUMENTS

| | | | |
|---|---|---|---|
| 2010/0057131 A1* | 3/2010 | Ely | A61B 17/7049 606/250 |
| 2011/0040328 A1* | 2/2011 | Miller | A61B 17/7091 606/246 |
| 2012/0283778 A1* | 11/2012 | Yeh | A61B 17/7067 606/250 |
| 2013/0096624 A1 | 4/2013 | Di Lauro et al. | |
| 2013/0096637 A1 | 4/2013 | Richelsoph et al. | |
| 2014/0100613 A1 | 4/2014 | Iott et al. | |

(Continued)

FOREIGN PATENT DOCUMENTS

| | | |
|---|---|---|
| WO | 2005006948 A2 | 1/2005 |
| WO | 2015066325 A1 | 5/2015 |

*Primary Examiner* — Eduardo C Robert
*Assistant Examiner* — Tara Rose E Carter

(57) ABSTRACT

A system for implanting a bone fixation system including an implant head inserter associated with each hook member and positionable relative to one of the elongate members to engage the hook member with the elongate member; a preliminary locking instrument associated with each implant head inserter and configured to engage the respective elongate member and lock the position of the hook member and implant head inserter relative to the elongate member; a compressor assembly configured to engage the implant head inserters and compress them toward one another; a path creation tool configured to be extended through holes in the hook members to define a connector member path between the hook members; and a rod introduction instrument configured to support the connector member and direct it through the connector member path. Methods of implanting a bone fixation system are also provided.

20 Claims, 45 Drawing Sheets

(56) References Cited

U.S. PATENT DOCUMENTS

2014/0277163 A1* 9/2014 Kretzer .............. A61B 17/7049
606/278

* cited by examiner

MIS CROSS-CONNECTOR

CROSS REFERENCE TO RELATED APPLICATION

The present application is a continuation application of U.S. patent application Ser. No. 15/226,011, filed Aug. 2, 2016 (published as U.S. Patent Pub. No. 2017-0128101), which is a continuation-in-part of U.S. patent application Ser. No. 14/936,071, filed Nov. 9, 2015, now U.S. Pat. No. 10,335,205, the contents of all of which are incorporated herein by reference in their entireties for all purposes.

FIELD OF THE DISCLOSURE

The present disclosure relates to bone fixation constructs that may include a stabilization element, and, more particularly, to bone fixation constructs that may include a connector system that may be coupled to, for example, one or more elongate members.

BACKGROUND OF THE DISCLOSURE

Intervertebral discs are susceptible to a variety of weaknesses and abnormalities that can affect their ability to provide support and structure. Many of the abnormalities may be the result of, for example, trauma, degenerative disc disease, or tumors, which can cause severe pain or damage to the nervous system. Also, movement of the spinal column may be significantly limited by such abnormalities. Known treatments of such abnormalities typically involve affixing screws or hooks to one or more vertebrae and connecting the screws or hooks to a rod that is aligned with the longitudinal axis of the spinal column to immobilize the spinal segments with respect to each other. Pedicle screw systems are frequently used to provide spinal fixation.

A number of pedicle screw systems are known, which share common techniques and principles of screw placement and rod attachment. Generally, bone screws are screwed into pedicles of vertebrae and coupled to at least one elongated rod. The pedicles, which consist of a strong shell of cortical bone and a core of cancellous bone, are generally used for the bone screw sites because they provide a strong point of attachment to a spine and, thereby, the greatest resistance against bone-metal junction failure. Known pedicle screw systems typically include pedicle screws and rods to stabilize adjacent spinal segments. Such systems may also include variable angled coupling caps (or heads) on the pedicle screws to allow for angular adjustment of the coupling mechanism between the rod and screws. Since pedicle size and angulation varies throughout the spinal column, several different sizes and shapes of pedicle screws are used in these systems. These systems are generally designed to provide stable and rigid structures to promote bone growth and fusion. The systems may include a pair of rods, plates, or other elongate members affixed to the pedicle screws along the longitudinal axis of the spine.

The strength and stability of a multi-rod, plate, or other elongate member assembly can be increased by intercoupling the elongate members with a cross connector that extends substantially horizontal to the longitudinal axes of the elongate members, across the spine. Due to a wide variety of factors, the elongate members are seldom geometrically aligned in clinical applications. Furthermore, typical cross connectors are inserted through either a fully open or mini-open procedure, resulting in resection of the spinal ligaments and bone. A minimally invasive connector system with at least some adjustability is needed that can accommodate for variations in geometrical alignment while minimizing damage to the supporting anatomical structures.

SUMMARY OF THE DISCLOSURE

The present disclosure is generally directed towards a bone fixation system or construct for implanting in bone, wherein the bone fixation system comprises a connector assembly to add additional stability to the system. The bone fixation system comprises: a plurality of bone fastener assemblies that attach to bone; a pair of elongate members that attach to the plurality of bone fastener assemblies; a connector member that contacts the pair of elongate members; and a plurality of locking caps that secure the connector member and the elongate members to the plurality of bone fastener assemblies, wherein at least one of the plurality of locking caps comprises a cap portion and a hook portion, where the cap portion is adapted to rotate while the hook portion is stationary.

At least one of the plurality of bone fastener assemblies may comprise: a bone fastener that attaches to bone; a coupler that connects to the bone fastener; and an extender that connects to the coupler. The extender may comprise: a coupling portion that attaches to the coupler; and a blade portion that attaches to the coupling portion. The coupling portion may comprise a threading. The blade portion may comprise a pair of extender blades. The cap portion of the at least one of the plurality of locking caps may comprise a threading that engages the threading in the coupling portion. The hook portion of the at least one of the plurality of locking caps may comprise a receptacle that receives a contact portion of the connector member. The receptacle may include an interface section that contacts the contact portion of the connector member, and a tapered section that contacts the contact portion of the connector member and allows adjustability of the connector member in the receptacle.

The bone fixation system may further comprise a sleeve that guides the connector member and said at least one of the plurality of locking caps during installation of the bone fixation system.

A system for implanting a bone fixation system is also disclosed. The system includes an implant head inserter associated with each hook member and positionable relative to one of the elongate members to engage the hook member with the elongate member; a preliminary locking instrument associated with each implant head inserter and configured to engage the respective elongate member and lock the position of the hook member and implant head inserter relative to the elongate member; a compressor assembly configured to engage the implant head inserters and compress them toward one another; a path creation tool configured to be extended through holes in the hook members to define a connector member path between the hook members; and a rod introduction instrument configured to support the connector member and direct it through the connector member path. Methods of implanting a bone fixation system are also provided.

Additional features, advantages, and embodiments of the disclosure may be set forth or apparent from consideration of the detailed description and drawings. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to help explain the principles of the disclosure. No attempt is made to show structural details of the disclosure in more detail than may be necessary for a fundamental understanding of the disclosure and the various ways in which it may be practiced. In the drawings.

Figure 1:
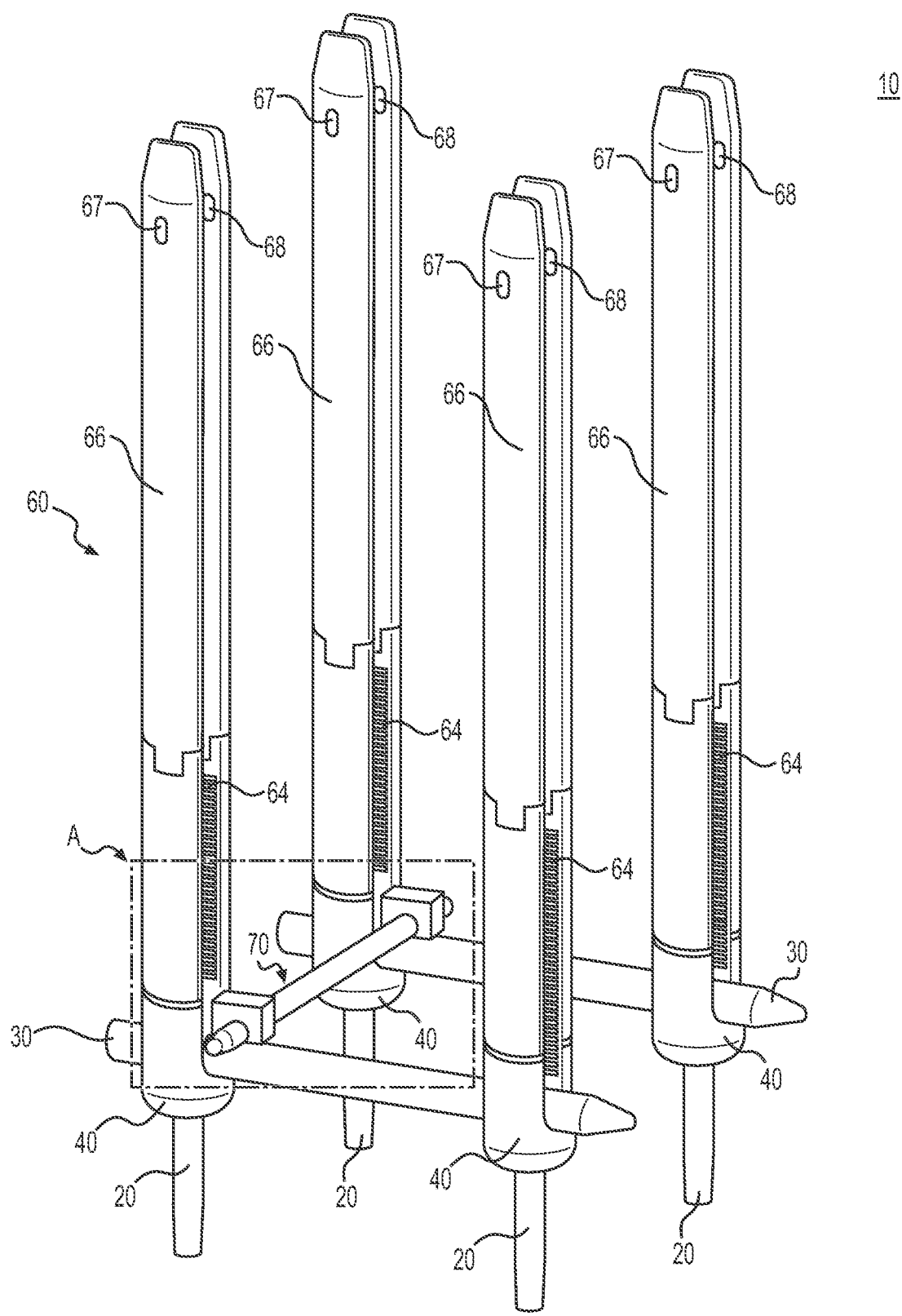
FIG. 1 shows an exemplary embodiment of a bone fixation construct, according to the principles of the disclosure.

The present disclosure is further described in the detailed description that follows.

DETAILED DESCRIPTION OF THE DISCLOSURE

The disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the views of the drawings.

FIG. 1 shows an example of a bone fixation construct 10 that is constructed according to the principles of the disclosure. The bone fixation construct 10 includes a plurality of bone fasteners 20 (for example, four), one or more elongate members 30 (for example, two), a plurality of couplers 40 (for example, four), a plurality of extenders 60 (for example, four), and a connector assembly 70. The various components of the bone fixation construct 10 (or 10A, or 10B, or 10C, discussed below) may be made of a material such as, for example, stainless steel, titanium, titanium-alloy, or the like.

Figure 2:
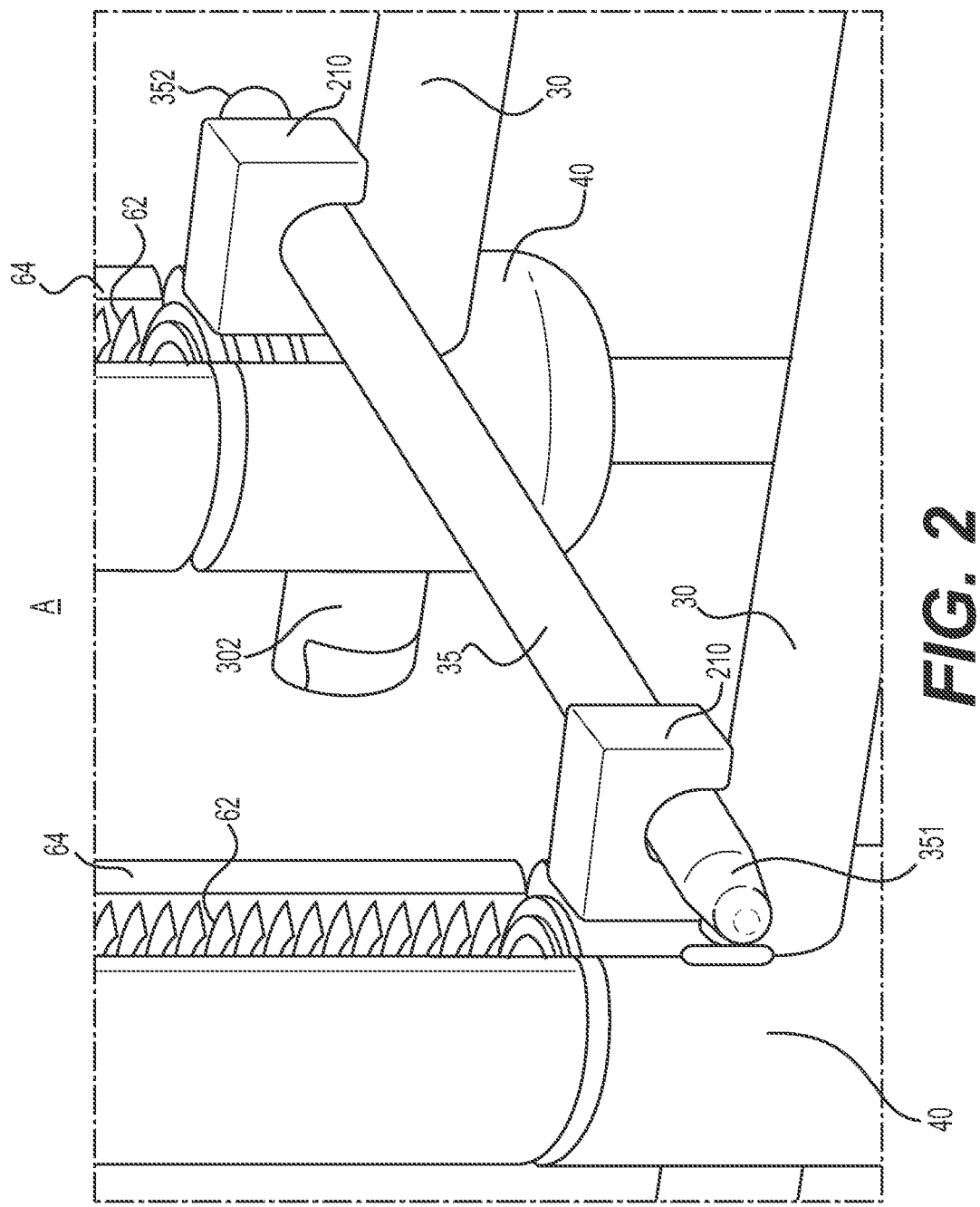
FIG. 2 shows a detailed view of a portion A of the bone fixation construct in FIG. 1.

FIG. 2 shows a detailed view of a portion A of the bone fixation construct 10 in FIG. 1, which includes the connector assembly 70. As seen in the illustration, the connector assembly 70 includes a pair of locking caps 210 and a connector member 35.

Referring to FIGS. 1 and 2, and referring to one of the bone fasteners 20 with the understanding that the description may apply equally to the other bone fasteners 20, the bone fastener 20 may include a bone screw, such as, for example, any of the various pedicle screws common in the art, including, for example, a polyaxial pedicle screw. The bone fastener 20 may include a shaft portion that may be configured at the distal end to penetrate and facilitate insertion of the bone fastener 20 into bone. At the proximal end, the bone fastener 20 may include a head portion (not shown) that may be coupled to a corresponding coupler 40 and configured to be, for example, polyaxially adjustable with respect to the corresponding coupler 40. For instance, the coupler 40 may pivot and/or rotate with respect to the corresponding bone fastener 20.

The head portion of the bone fastener 20 may include a tool receptacle (not shown) at its proximal end that is configured to receive a driver tool (not shown) to drive the bone fastener 20 into bone. The tool receptacle may have a hexagon shape, a torque-screw shape, or any other shape that may facilitate the bone fastener 20 being driven into a bone by the driver tool.

The shaft portion of the bone fastener 20 may have a thread (not shown) that is adapted to be screwed into a bone, such as, for example, a vertebra. Alternative formations may be formed in/on the shaft portion which provide the intended purposes of securing the bone fastener 20 within a bone, as described herein. The shaft may have a tapered shape, which may be provided with a high pitch thread. It is noted that the length, diameter, thread pitch, and thread diameter ratio of the shaft may be selected based on the particular application of the bone fastener 20, as understood by those skilled in the art.

The bone fasteners 20 may be substantially the same or substantially different from each other with respect to, for example, shaft length, shaft diameter, thread pitch, thread diameter ratio, and the like.

The elongate member 30 may include, for example, an elongate rod, a pin (not shown), a brace (not shown), a spring (not shown), a cord (not shown), a resilient extension (not shown), or any other stabilization device that may be secured by the locking cap(s) 210 in the coupler(s) 40 to provide stabilization to the construct 10. The locking cap(s) 210 may be used to secure the elongate member 30 in the coupler(s) 40, as illustrated in FIG. 1.

Figure 7:
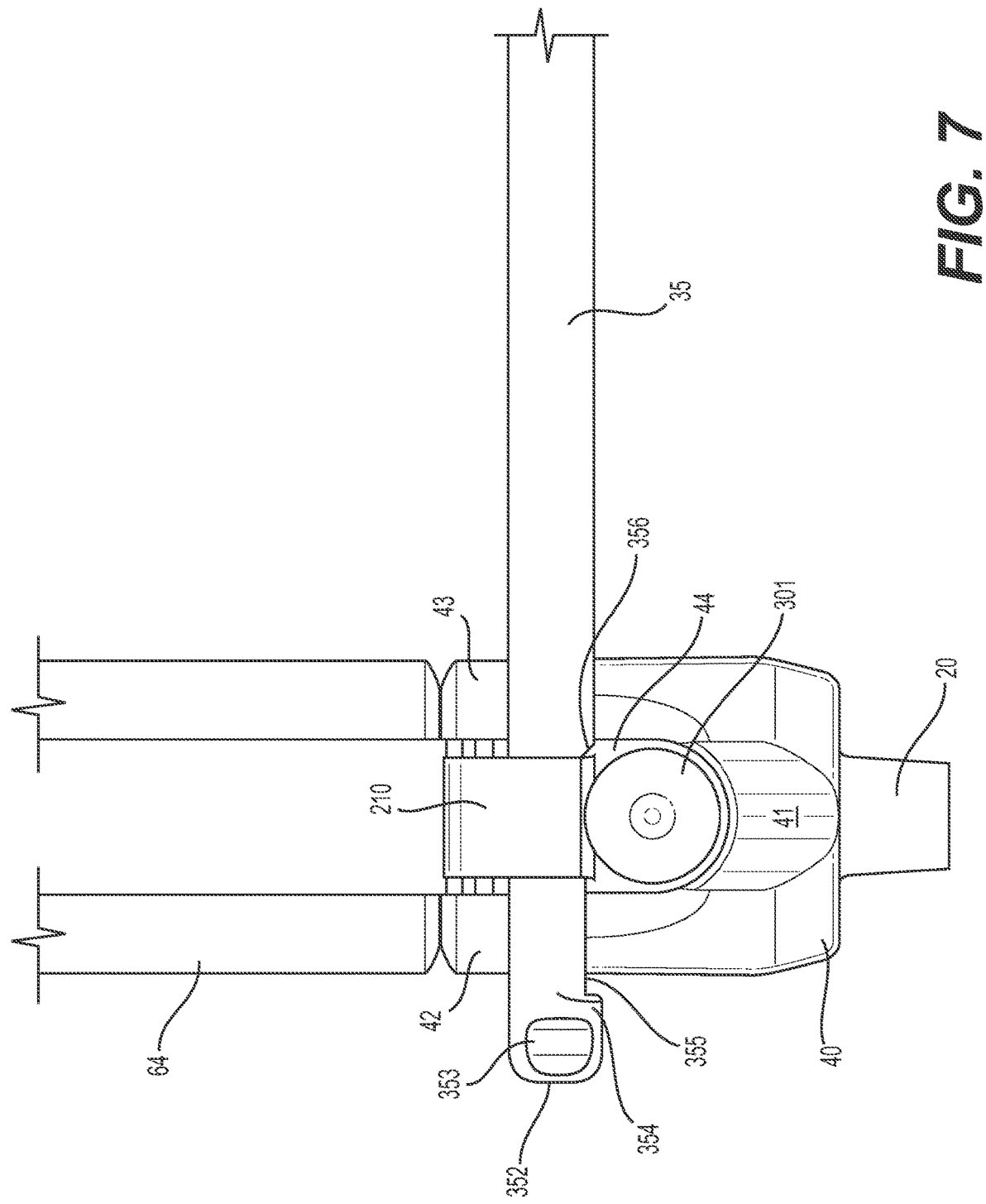
FIG. 7 shows a detailed front (or back) view of the portion of the fixation construct in FIG. 4 after insertion of the connector member.

Referring to one of the couplers 40, with the understanding that the description may apply equally to the other couplers 40, the coupler 40 may include a coupler body 41 that may have, for example, a "tulip" shape (shown in FIG. 7). The coupler body 41 may be configured to rotate and/or pivot with respect to the bone fastener 20. At its proximal end, the coupler body 41 may include a pair of upwardly extending arms 42, 43 and a slot 44 formed between the extending arms 42, 43 (for example, shown in FIG. 7). The slot 44 may be configured to receive the elongate member 30, as illustrated in FIG. 7. The coupler body 41 may be configured to receive and hold the locking cap 210, as seen in FIG. 1.

The coupler body 41 may hold the locking cap 210 in a predetermined location along the longitudinal axis of the coupler body 41 after insertion in the coupler body 41, so that a contact surface 216 (shown in FIG. 3B) of the locking cap 210 contacts and presses upon a surface of the elongate member 30 to hold and secure the elongate member 30 in a fixed position, preventing the elongate member 30 from moving rotationally, angularly or longitudinally.

The coupler body 41 may include a threading that may be provided on the interior surfaces of the upwardly extending arms 42, 43, as seen in FIG. 1. The threading may be configured to receive and engage a corresponding threading 212 on the locking cap 210 (shown in FIG. 3B). Alternatively, the coupler body 41 may include a tongue and grove mechanism (not shown), or any other retaining mechanism that can secure the locking cap 30 in a predetermined location in the coupler body 41.

Referring to FIG. 7, the upwardly extending arms 42, 43 of the coupler body 41 may extend longitudinally in a superior direction and include an interior, an exterior, and upper surfaces. One or both of the extending arms 42, 43 may include one or more extender engaging portions (not shown), which may be configured to receive and engage corresponding portions of the extender 60. The coupler body 41 may be configured to receive and engage a driver tool (not shown) and be driven by the tool to rotate and/or angularly adjust the coupler body 41. The coupler body 41 may be adjusted (for example, rotated and/or pivoted) simultaneously with the corresponding extender 60. The extender 60 may be configured to be attachable to and/or removable from the coupler body 41. The extender 60 may be integrally formed with the coupler body 41 and configured to be removable from the coupler body 41.

Referring to one of the extenders 60, with the understanding that the description may apply equally to the other extenders 60, the extender 60 may include, for example, a coupling portion 64 and a blade portion 66. The blade portion may include a pair of extender blades 67, 68. The length and/or diameter of the extender 60 may vary to meet varying patient anatomy. The blade portion 66 may be coupled to, or integrally formed with the coupling portion 64. The coupling portion 64 may include a threading 62 (shown in FIG. 2) that may be configured to receive and engage the threading 212 on the locking cap 210 (shown in FIG. 3B). The coupling portion 64 may be removably connected to a corresponding coupler 40. The interface between the coupling portion 64 and the corresponding coupler 40 may be configured to be substantially seamless, allowing the locking cap 210 to be seamlessly screwed longitudinally along the inner surfaces of the coupling portion 64 and the threading in the coupler body 41.

Figure 24:
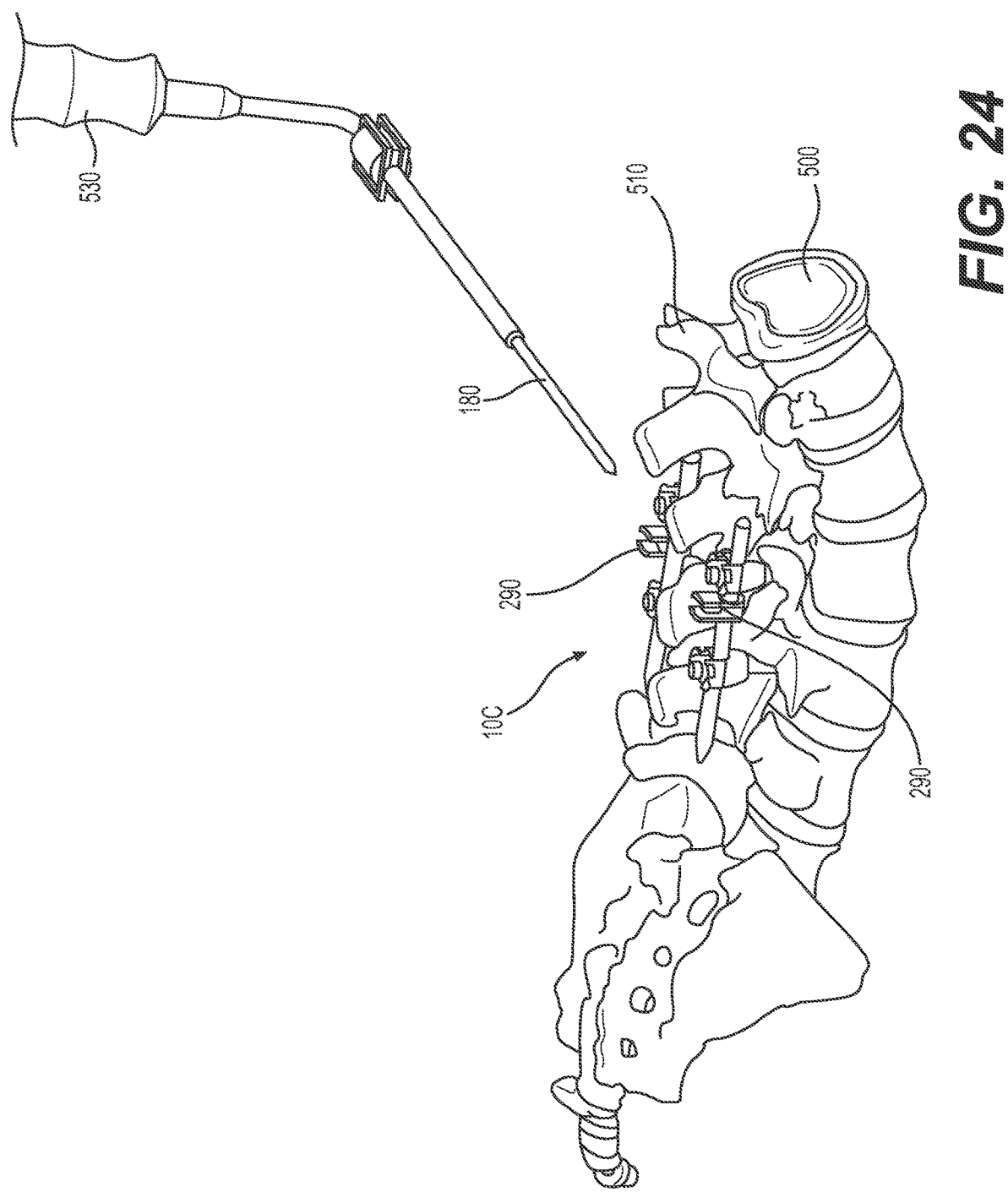

The extender 60 may be configured to retract tissue and provide an unobstructed channel for insertion of tools (not shown), such as, for example, a screw driver (not shown), rod introduction instrument 530 (shown in FIGS. 24-25), and the like. For instance, the blade portion 66, including the extender blades 67, 68, may be configured to provide a longitudinal channel that extends from the proximal ends of the extender blades 67, 68, to the head portion (not shown) of the bone fastener 20, allowing for tools, such as, for example, the screw driver (not shown) to be inserted into, engage the head portion (not shown) and drive the bone fastener 20 into bone (not shown). The extender channel may be configured to receive and guide, for example, the elongate member 30, which may be introduced at the proximal end of the extender blades 67, 68 and travel through the extender channel (for example, percutaneously) to the distal end of the blade portion 66. At the distal end of the blade portion 66, the elongate member 30 may be manipulated and maneuvered using, for example, the rod introduction instrument 530 (shown in FIGS. 24-25) into a desired position in the bone fixation construct 10 (shown in FIG. 1).

Figure 3A:
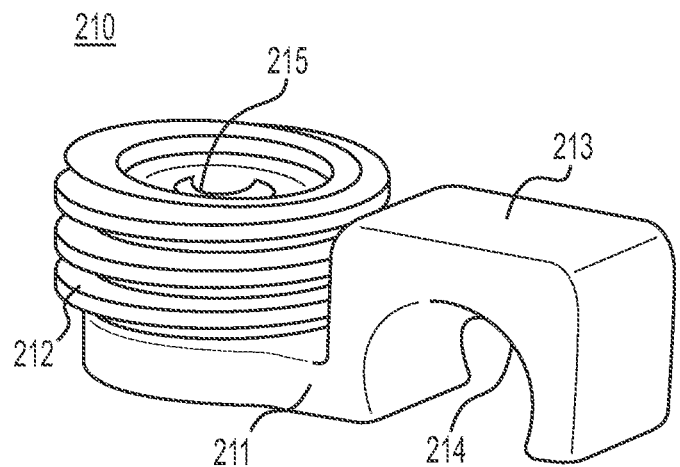
FIGS. 3A-3C show a perspective view, a side view and a bottom view, respectively, of an exemplary embodiment of a locking cap, according to the principles of the disclosure.
Figure 3B:
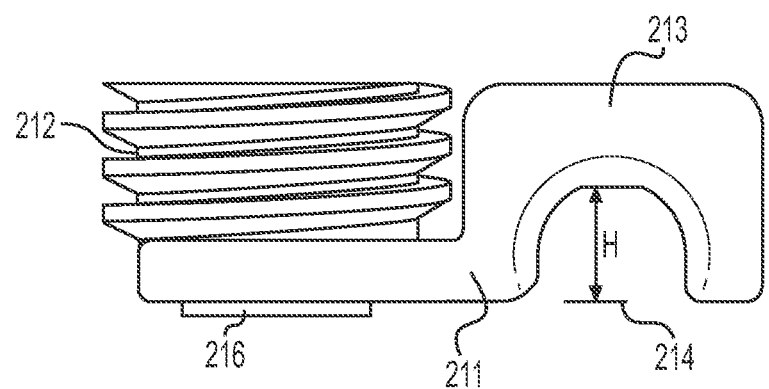
Figure 3C:
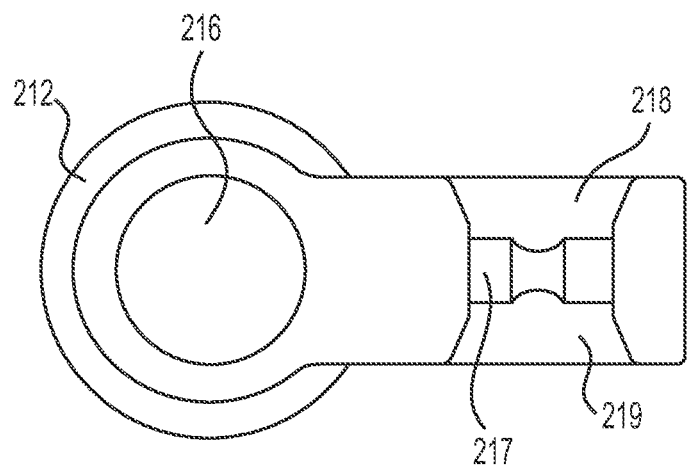
Figure 3D:
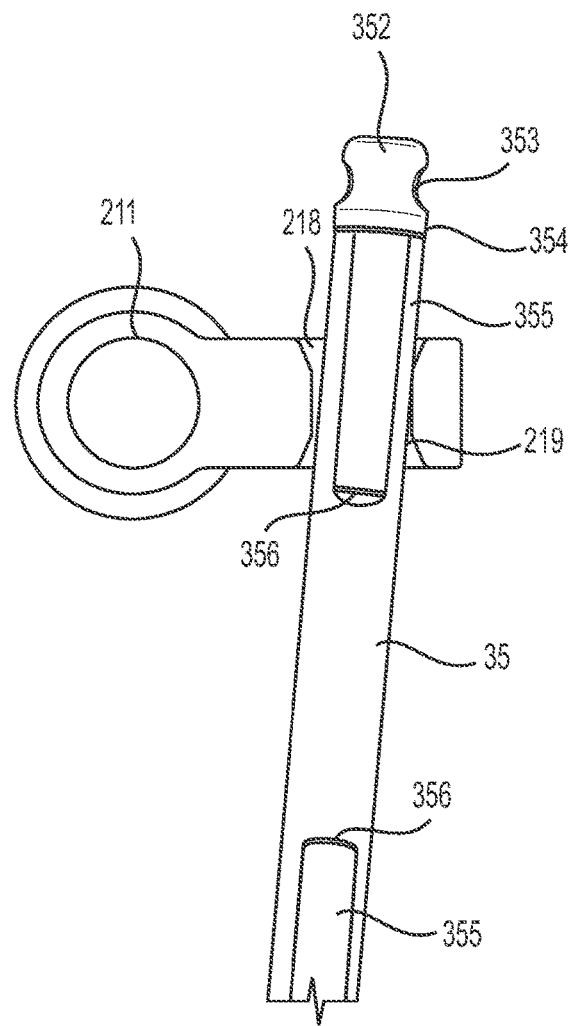
FIGS. 3D-3E show a bottom view of the locking cap in FIGS. 3A-3C with a connector member.
Figure 3E:
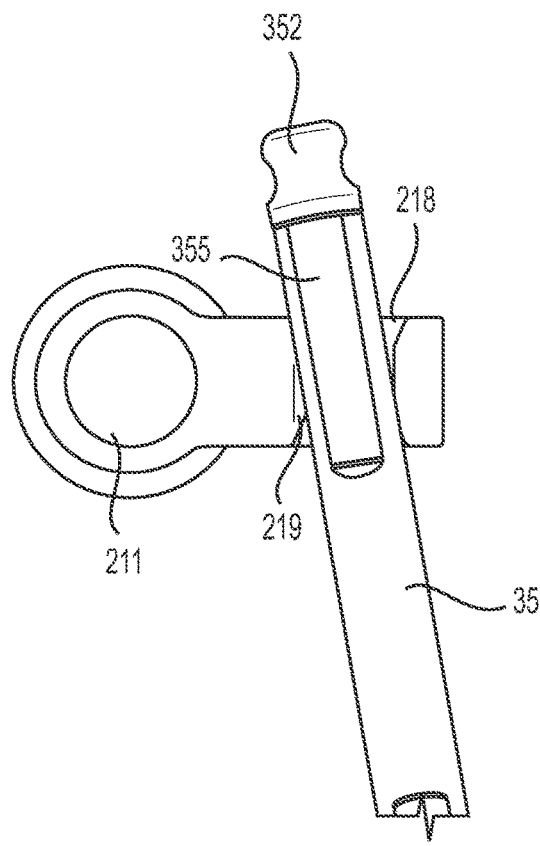

FIGS. 3A-3C show a perspective view, a side view and a bottom view, respectively, of an exemplary embodiment of the locking cap 210; and FIGS. 3D-3E show a bottom view of the locking cap 210 with a connector member 35 adjustably positioned at different angles with respect to the locking cap 210. As seen in FIGS. 1-2 and 3A-3E, the connector assembly 70 may include the pair of locking caps 210 and the connector member 35.

Referring to FIGS. 1-2 and 3A-3C, each of the locking caps 210 may be positioned in a corresponding coupler 40 and adjusted to secure a contact portion 355 of the connector member 35 in the bone fixation construct 10. Each locking cap 210 may include a cap portion 211 and a hook portion 213. The cap portion 211 may be attached to the hook portion 213 such that the cap portion 211 may be capable of spinning freely with respect to the hook portion 213. The cap portion 211 may include the threading 212 and a tool receptacle 215. The tool receptacle 215 may have a hexagon shape, a torque-screw shape, or any other shape that may facilitate the cap portion 211 being driven to, for example, rotate in and fasten to the coupler body 41 by the driver tool (not shown).

As seen in FIGS. 3A-3C, the hook portion 213 may include a receptacle 214 that may be configured to receive a portion (for example, the contact portion 355) of the connector member 35. The receptacle 214 may include an interface section 217 and one or more tapered sections 218, 219. The interface section 217 has an inner diameter this is greater than the outer diameter of the portion of the connector member 35 to be secured by the locking cap 210. The tapered sections 218, 219 may have a conical shape. The tapered sections 218, 219 have varying inner diameters that range from a diameter that is substantially equal to the inner diameter of the interface section 217 nearest the interface and increasing to an inner diameter that is greater than the inner diameter of the interface section 217, so as to allow angular movement of the contact portion 355 of the connector member 35 in the receptacle 214, and, thereby, adjustability of the connector member 35 with respect to the locking cap 210. The receptacle 214 may have a height H (shown in FIG. 3B) that is less than the height (or thickness) of, for example, the contact portion 355, such that a part of the contact portion 355, when the connector member 35 is installed in the receptacle 214, extends below the lower surface of the hook portion 213, so that it may be forced by the hook portion 213 to contact and engage the surface of the elongate member 30, thereby securing the connector member 35, elongate member 30 and locking cap 210 to the coupler 40.

Referring to FIGS. 3D-3E, the connector member 35 may be substantially the same as, or different from the elongate member 30. The connector member 35 may be substantially round in its cross-section and substantially elongated in its length. The connector member 35 may include, for example, an elongate rod (shown in FIG. 2), a pin (not shown), a brace (not shown), a spring (not shown), a cord (not shown), a resilient extension (not shown), or any other stabilization device that may be secured by the locking caps 210 to the construct 10. The connector member 35 may include attributes that may be selected based on, for example, variations in anatomy. For instance, the connector member 35 attributes that may be selected include a length, width, configuration, shape, or the like, depending on the particular application.

The connector member 35 may include the contact portion 355 at one or both ends. The contact portion 355 may be formed between ends 354, 356, as seen in FIG. 3D. The contact portion 355 may be substantially flat, or it may be shaped to match to and receive the outer surface of the elongate member 30. For instance, the contact portion 355 may include an interface portion similar to interface section 217 (shown in FIG. 3C) and/or at least one tapered portion similar to tapered section(s) 218 (and/or 219). The contact portion 355 may be configured to provide greater surface contact between the surface(s) of the contact portion 355 and the surface of the elongate member 30, thereby preventing the elongate member 30 from moving (for example, sliding, rotating, or pivoting). The contact portion 355 may have any structure that may facilitate engaging and securing the connector member 35 on top of the elongate member(s) 30, without departing from the scope or spirit of the disclosure. The contact portion 355 may be configured to rest atop of the elongate member 30, as seen in FIG. 2.

The connector member 35 includes an end 352 that may include a tool engagement portion 353. The tool engagement portion 353 may be configured to be securely held by the rod introduction instrument 530 (shown in FIGS. 24-25), such that the connector member 35 may be rotated about its longitudinal axis, and linearly and/or angularly adjusted in the real-world coordinate system, including the x-axis, y-axis, and z-axis (shown in FIG. 5).

Figure 4:
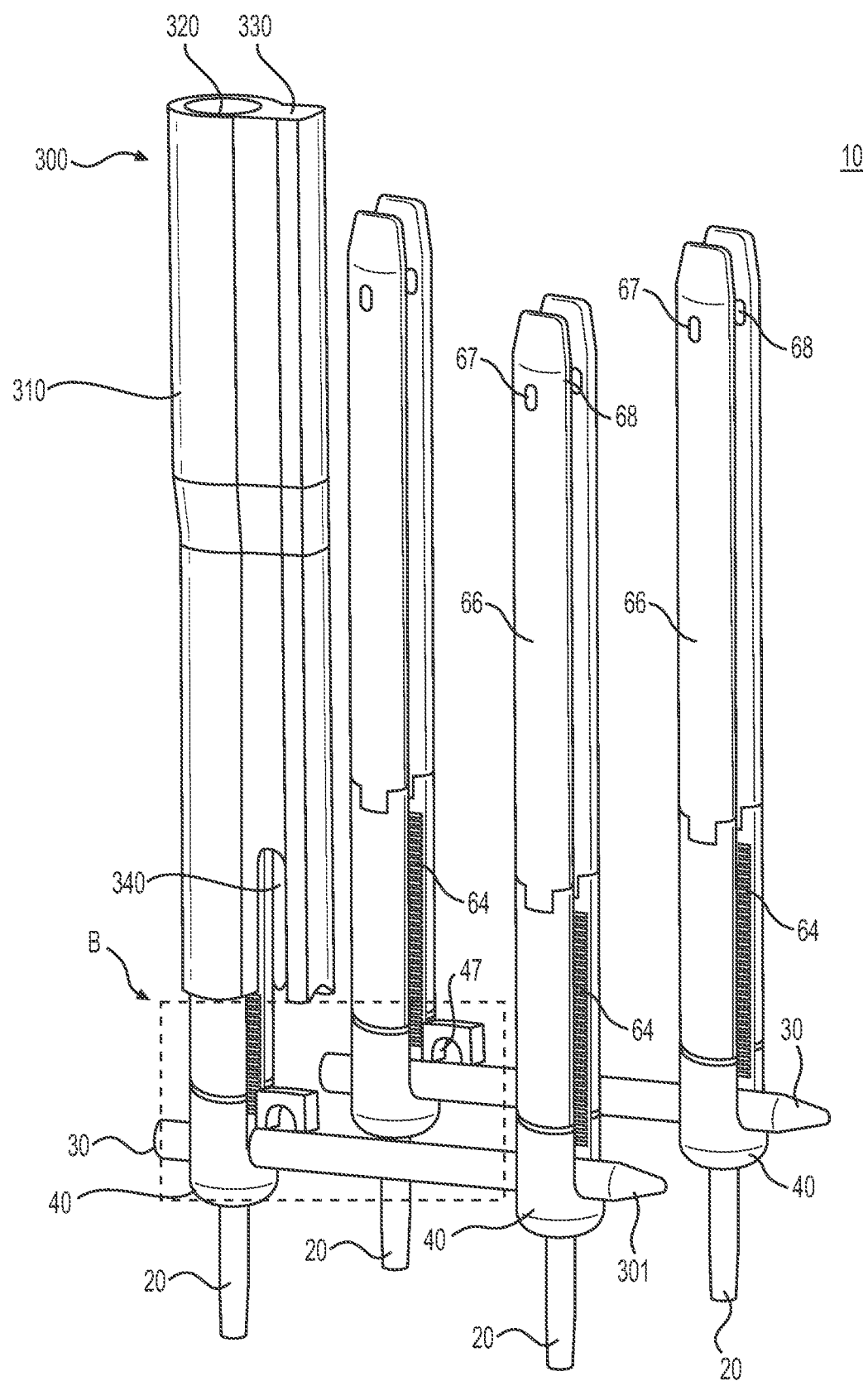
FIG. 4 shows the bone fixation construct of FIG. 1 during a process of installing the connector member.

FIG. 4 shows the bone fixation construct 10 in a near-complete form during a process of installing the connector member 35; and, FIGS. 5-8 show detailed views of a portion B of the bone fixation construct 10 after installation of the connector member 35 in the bone fixation construct 10.

Referring to FIG. 4, after a surgical area is cleaned on a patient, a minimally invasive incision made, muscle tissue moved to the side(s), and other common surgical procedures carried out, tracks for the bone fasteners 20 may be prepared. In this regard, hard bone surface may be removed and a guide track may be inserted under x-ray guidance into, for example, the pedicle of the vertebrae. The depth and position of the guide track may be checked. Where the bone fastener 20 includes a bone screw, a thread may be tapped into the bone to form a tap (not shown) to receive and securely hold the bone fastener 20. The process would be repeated for each bone fastener 20 of the bone fixation construct 10.

Using a driver tool (not shown), as is known by those skilled in the art, the driver tool may be inserted in and moved through the extender channel of the extender 60 toward the bone fastener 20. The tool may contact the head portion (not shown) of the bone fastener 20 and the driver tool may be manipulated until the driver tool head (not shown) is sufficiently seated in and engaged with the tool receptacle (not shown) in the bone fastener 20 to ensure a secure connection. The driver tool, including the bone fastener assembly that comprises the bone fastener 20, the coupler 40, and the extender 60, can then be aligned with the tap (not shown) in the bone and screwed into the threaded tap.

Alternatively, the bone fastener assembly, including the bone fastener 20, the coupler 40, and the extender 60, may be partially installed in the tap before being contacted by the driver tool. Once the bone fastener assembly is implanted in the desired position, the driver tool may be removed and the process repeated for each bone fastener assembly, including the bone fastener 20, coupler 40, and extender 60 of the bone fixation construct 10.

After the bone fasteners 20 are securely and properly placed in corresponding taps, a first elongate member 30 may be inserted into and moved through the extender channel of the extender 60 toward the distal end of the coupling portion 64 of the extender 60. The elongate member 30 may be positioned in the slots 44 (shown in FIG. 7) of the pair of adjacent couplers 40. The pair of couplers 40 may be adjusted and positioned such that the slots 44 of the couplers substantially line up with each other, providing a virtual channel for the elongate member 30. Once the elongate member 30 is seated in a desired position with respect to the pair of couplers 40, a cap (not shown) may be installed in the coupler 40 proximate the distal end 301 of the elongate member 30 (shown in FIG. 4) and positioned to secure a portion of the elongate member 30 in the coupler 40. In the case where cap (not shown) includes a threading, the cap may be screwed into the coupler 40 using a screw driver (not shown).

Alternatively, the cap (not shown) may be partially installed in the coupler 40 prior to installation of the bone fastener assembly, which includes the bone fastener 20, coupler 40, and extender 60. The distal end 301 of the elongate member 30 may be inserted through the opening in the coupler 40 formed by the slot 44 and bottom side of the cap (not shown). After the elongate member 30 is seated in a desired position, the cap (not shown) may be positioned to secure the distal end 301 of the elongate member 30 in the coupler 40, such as, for example, by screwing the cap (not shown) in the coupler 40.

The process may be repeated for the second elongate member 30, which may be positioned in the slots 44 (shown in FIG. 7) of a second pair of adjacent couplers 40. The second pair of couplers 40 may be adjusted and positioned such that the slots 44 of the second pair of couplers substantially line up with each other, providing a virtual channel for the second elongate member 30. Another cap (not shown) may be installed in the coupler 40 that is located proximate the distal end 301 of the elongate member 30 (shown in FIG. 4), and positioned to secure end 301 in the coupler 40.

The cap(s) (not shown) may include the locking cap 210 (shown in FIGS. 3A-3E), a cap 50 (shown in FIG. 8), a cap 92 (shown in FIG. 12), or any other cap that is known in the art and that may be installed in the coupler 40 to secure the elongate member 30 in the coupler, including, for example, a set screw, or the like, or any of the various caps that include a bottom portion (not shown) that may be shaped to match the shape of the elongate member 30 so as to provide increased surface contact between the cap (not shown) and elongate member 30.

As seen in FIG. 4, after the pair of elongate members 30 are positioned in the bone fixation construct 10, a sleeve 300 may be positioned over a proximate end of the extender 60 and slid over the extender body toward its distal end. The sleeve 300 may be slid over part of the length of the extender 60, leaving sufficient space at its distal end to introduce and install the connector member 35 (shown in FIG. 5). Once the connector member 35 is in position, the locking cap(s) 210 may be inserted into the corresponding coupler(s) 40.

Alternatively, one of the locking caps 210 may be installed prior to installation of the connector member 35. In this instance, an end of the connector member 35 may be inserted through an opening 47 that is formed by the receptacle 214 (shown in FIG. 3A) and the elongate member 30, as seen in FIG. 4.

Figure 5:
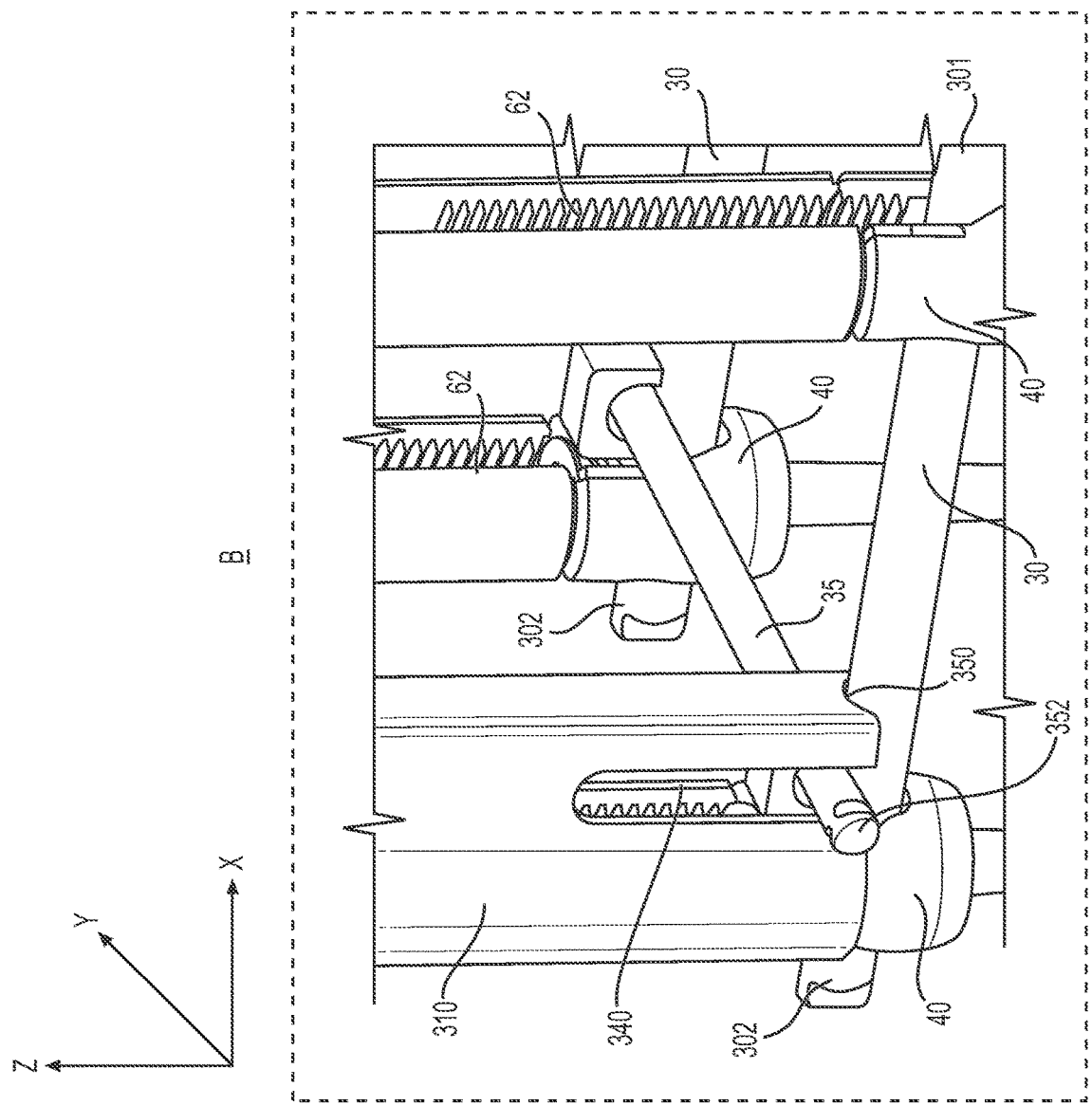
FIG. 5 shows a detailed perspective view of a portion of the bone fixation construct in FIG. 4 after insertion of the connector member.
Figure 6:
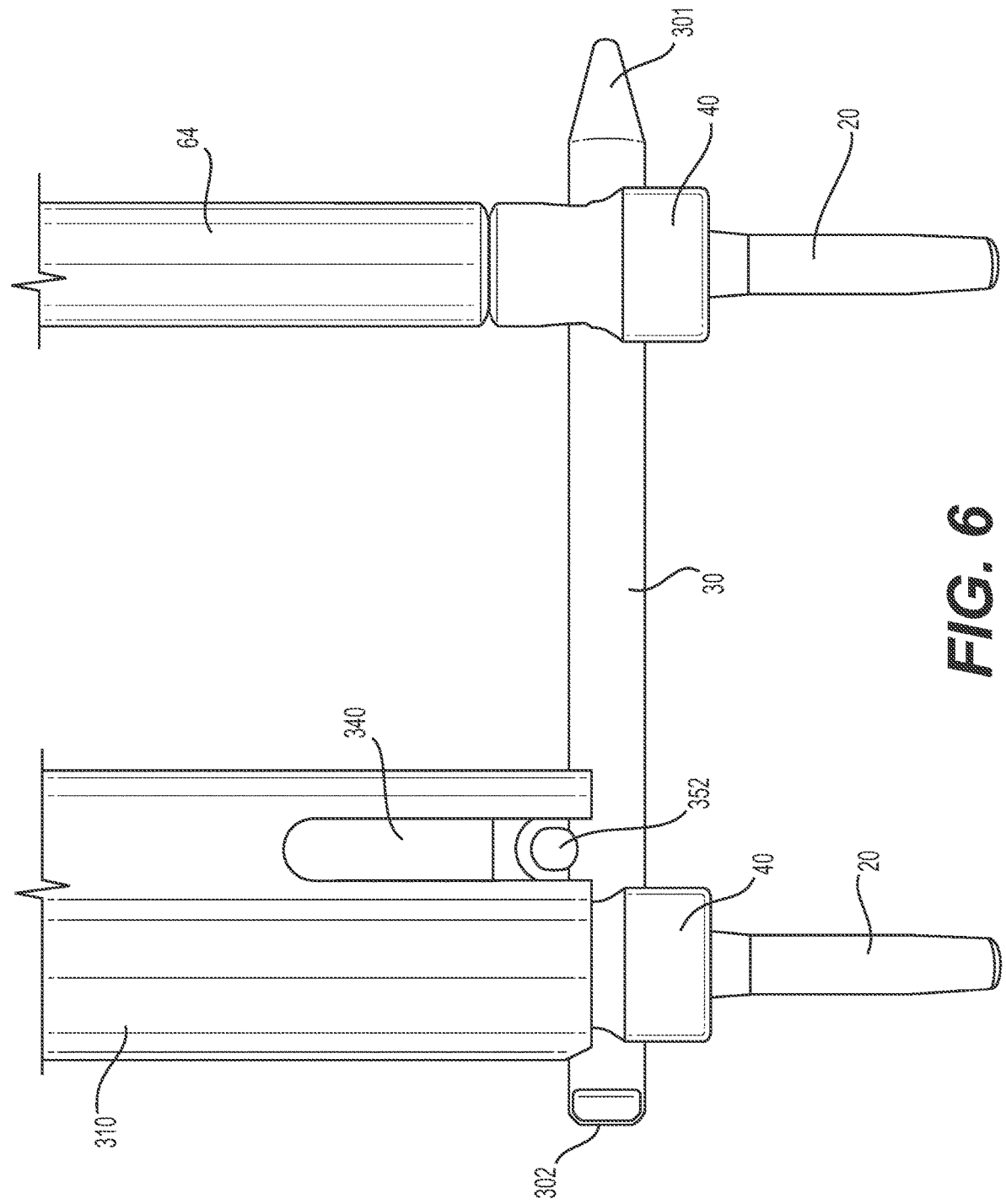
FIG. 6 shows a detailed side view of the portion of the bone fixation construct in FIG. 4 after insertion of the connector member.

Referring to FIGS. 4-6, the sleeve 300 includes a sleeve body 310 that may have a longitudinal extender channel 320 formed therein and extending from (and through) the proximal end of the sleeve body 310 to (and through) the distal end of the sleeve body 310. The extender channel 320 may have an internal geometry (not shown) that prevents it from spinning around the extender 60. The extender channel 320 is configured to receive and slide on the extender 60, having an inner diameter that is greater than the outer diameter of the extender 60.

The sleeve body 310 may also include an instrumentation channel 330 formed therein. The instrumentation channel 330 extends from (and through) the proximal end of the sleeve body 310 to (and through) the distal end of the sleeve body 310. The instrumentation channel 330 may have an internal geometry (not shown) that guides the connector member 35 to and through a sleeve opening 340 formed in the distal end of the sleeve 300. The sleeve opening 340 may be formed on one side of the sleeve body 310, allowing for exit of the connector member 35 on that side of the sleeve body 310; or, the sleeve opening 340 may be formed as, for example, a cut-out in the distal end of the sleeve body 310, allowing for exit of the connector member 35 on either side of the sleeve body 310.

The sleeve 310 may include a sleeve cutout 350 at its distal end that may be contoured to match the shape of the elongate member 30. The sleeve cutout 350 may facilitate proper alignment of the sleeve 310 with the elongate member 30, as well as help to keep the sleeve 310 stationary with respect to the elongate member 30.

The extender channel 320 and the instrumentation channel 330 may be configured such that the locking cap 210 may be inserted in the proximal end of the sleeve body 310 and moved through the channels 320, 330 to and through the distal end of the sleeve body 310, and to the corresponding coupler 40. The inner diameter (or width) of the instrumentation channel 330 may be less than the inner diameter (or width) of the extender channel. The instrumentation channel 330 may include an inner geometry that may help to align and position the hook portion 213 of the locking cap 210 (shown in FIG. 3A) such that the longitudinal axis of the locking cap 210 is substantially parallel to the elongate member 30 in the corresponding coupler 40.

Referring to FIGS. 5-6, the bone fixation construct 10 may be secured by threading the locking caps 210 into locked positions. In this regard, as each of the locking caps 210 is threaded (or screwed) in the corresponding coupler 40, the locking cap 210 travels toward the elongate member 30, locking the elongate member 30 in place and simultaneously locking the connector member 35 on top of the elongate member 30.

Referring to FIG. 7, the connector member 35 may be positioned such that the contact portion 355 is positioned on top of the elongate member 30. The ends 354, 356 may assist in positioning the contact portion 355 on top of the elongate member 30, as well as properly positioning the connector member 35 in the connector assembly 70. The ends 354, 356 may function as stops to prevent the connector member 35 from moving beyond either end 354, 356 with respect to the elongate member 30. The connector member 35 may include a contact portion 355 (not shown) at its other end (not shown), which may be similarly seated on top of and secured to the second elongate member 30.

Figure 26:
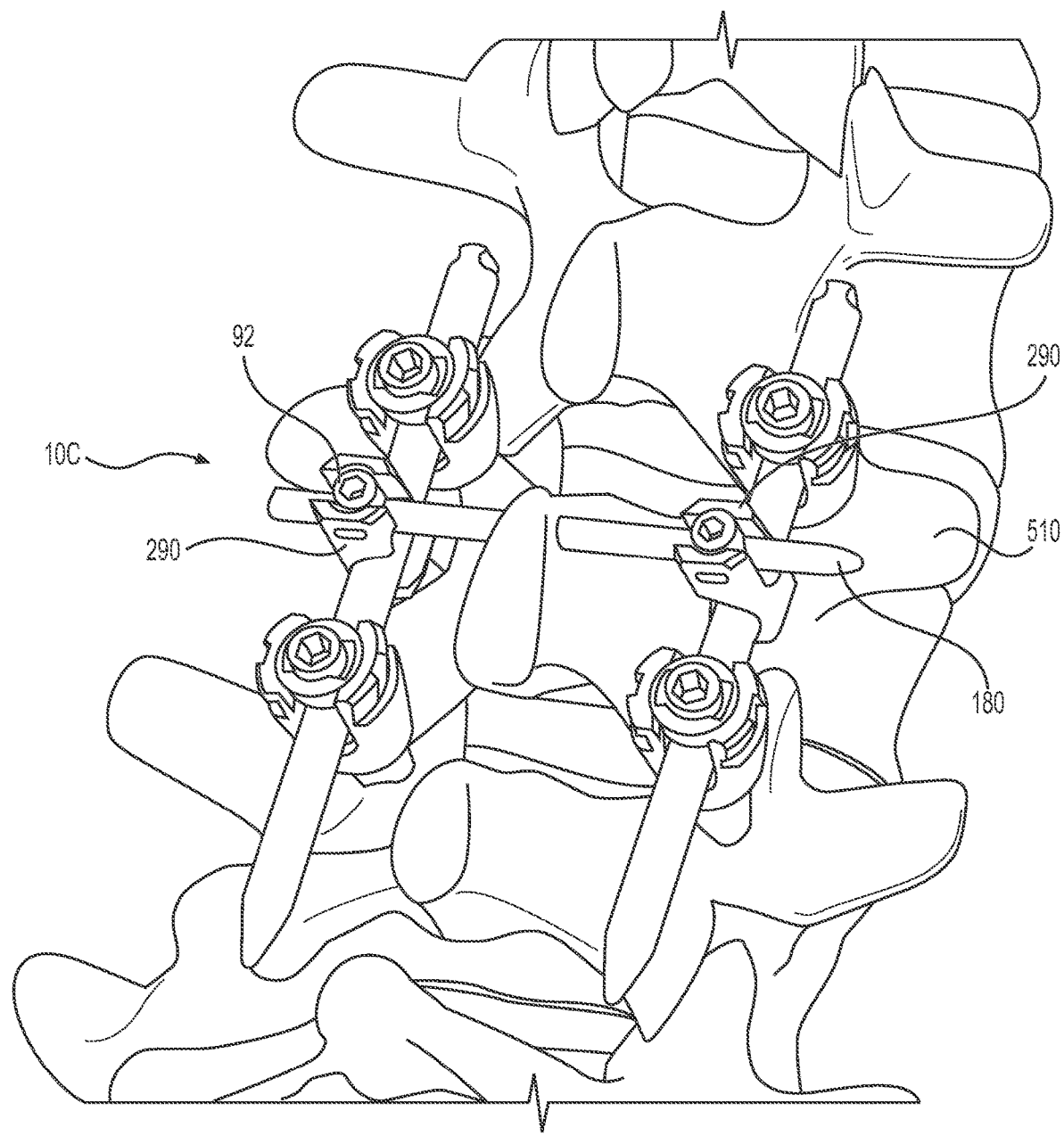

At completion of placement of the bone fixation construct 10, the construct may be installed in adjacent vertebrae, with the bone fasteners 20 implanted in the pedicles of the vertebrae. FIG. 26 shows an example of a bone fixation construct 10C installed in adjacent vertebrae, which is discussed in greater detail below. The connector member 35 (secured with locking caps 210) connects and secures the adjacent elongate members 30 to each other, thereby providing rigidity and stabilization between the elongate members 30.

Figure 8:
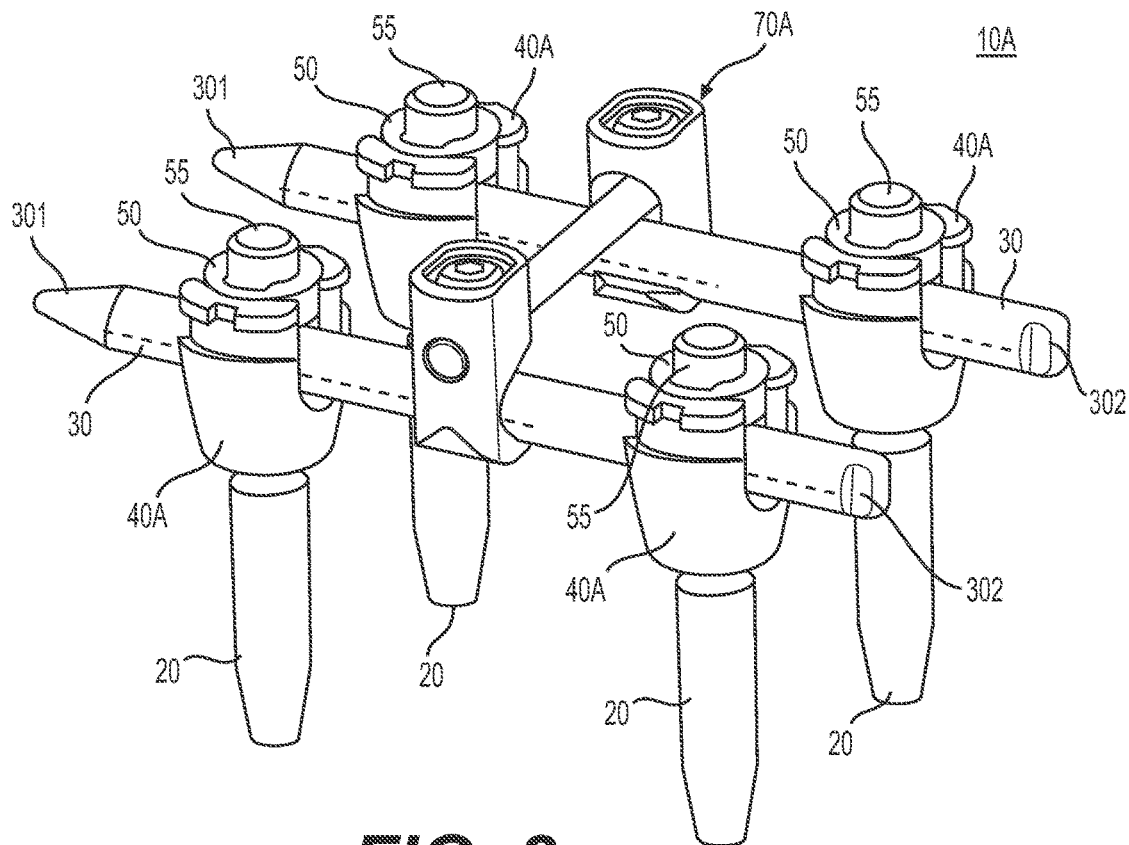
FIG. 8 shows another exemplary embodiment of a bone fixation construct, according to the principles of the disclosure.

FIG. 8 shows another exemplary embodiment of a bone fixation construct 10A, according to the principles of the disclosure. The bone fixation construct 10A includes a plurality of the bone fasteners 20, a plurality of couplers 40A, a plurality of caps 50, and a connector assembly 70A. Each of the caps 50 may include a driver receptacle 55 that receives and is engaged by a driver (not shown) to rotate and, thereby, travel toward the elongate member 30 seated in the coupler 40A, contacting and securing the elongate member 30 in the coupler 40A. The contact surface (not shown) of the caps 50 may be shaped to substantially match the outer shape of the elongate member 30, thereby increasing the surface contact and coefficient of static friction between the elongate member 30 and bottom surface of the caps 50.

The bone fixation construct 10A may be installed according to a process similar to that described above with respect to the bone fixation construct 10, or any other process commonly used to implant constructs, as understood by those skilled in the art. Once the bone fixation construct 10 is installed, the connector assembly 70A may be installed, as described herein, thereby providing increased stability of the construct.

Figure 9:
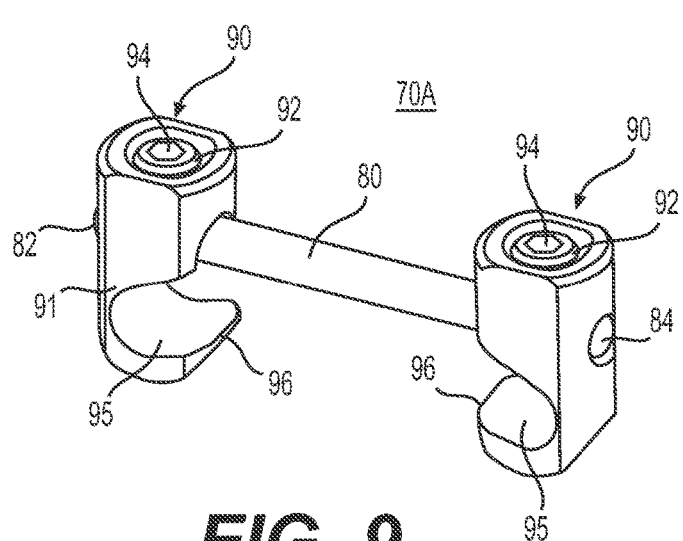
FIG. 9 shows an exemplary embodiment of a connector assembly, according to the principles of the disclosure.

FIG. 9 shows an exemplary embodiment of the connector assembly 70A, which provides a low profile configuration that can be inserted through a minimally invasive surgery (MIS) opening, and which may easily attach to pre-existing elongate members. The connector assembly 70A includes a connector member 80 and a pair of hook members 90. The connector member 80 may be similar to the connector member 35 (shown in FIG. 1) or the elongate member 30.

The connector member 80 may include, for example, an elongate rod (shown in FIG. 9), a pin (not shown), a brace (not shown), a spring (not shown), a cord (not shown), a resilient extension (not shown), or any other stabilization device that may be secured in the hook members 90 to provide stabilization. The connector member 80 may include attributes that may be selected based on, for example, variations in anatomy. For instance, the connector member 80 attributes may be selected from various lengths, widths, shapes, or the like, depending on the particular application.

The connector member 80 may be secured at each end 82, 84 to the hook members 90 by means of fasteners 92. Each fastener 92 may include a recess 94 that receives and is engaged by a driver tool (not shown) to drive the fastener 92 in and toward the connector member 80, thereby contacting and securing the connector member 80 to the hook member 90. The fastener 92 may include a threading 99 (shown in FIG. 12). The fastener 92 may include, for example, a set screw, a bolt, a screw, a cap, a pin, or the like.

Figure 10:
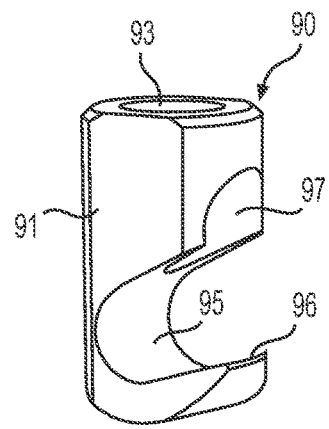
FIG. 10 shows an exemplary embodiment of a hook member that may be included in the connector assembly of FIG. 9.

FIG. 10 shows an exemplary embodiment of the hook member 90. As seen, the hook member 90 includes a hook member body 91 that may include an opening 93, a receptacle 95, a hook portion 96, and an opening 97. The opening 93 may be configured to receive and engage the fastener 92. The opening 93 may include a threading that may engage the corresponding threading 99 on the fastener 92 and cause the fastener 92 to be screwed downward (or upward) when the fastener 92 is rotated with respect to the hook member body 91.

The receptacle 95 may be shaped to receive and securely hold the elongate member 30 (shown in FIG. 8) in the hook member body 91. The receptacle 95 may be configured to catch and hold the entirety of the width (or diameter) of the elongate member 30 in the hook member body 91.

The hook portion 96 forms a lower part of the receptacle 95. The hook portion 96 may be shaped to catch and aid in attaching and securing the hook member 90 to the elongate member 30. For instance, the hook portion 96 may include an upwardly inclined configuration to catch the elongate member 30, such that the hook member body 91 will move upward with respect to the elongate member 30 as the elongate member 30 is moved deeper into the receptacle 95.

The opening 97 may be shaped to substantially match the shape of the end 82 (or 84) of the connector member 80. In the example seen in FIGS. 8-10, the opening 97 has a round shape, which receives and holds a cylindrically-shaped end 82 (or 84) of the connector member 80. The inner diameter of the opening 97 is greater than the outer diameter of the connector member end 82 (or 84). The inner diameter of the opening 97 extends into the receptacle 95 (shown in FIG. 10), such that when the elongate member 30 is properly seated in the receptacle 95 and the end 82 (or 84) of the connector member 80 is inserted into the opening 97, the connector member 80 may contact and force the elongate member 30 toward the hook portion 96 and inward toward the connector member body 91. The connector member 80 may be forced against the elongate member 30 by operation of the fastener 92, which contacts the connector member 80 and forces the connector member 80 against the elongate member 30 as the fastener 92 is screwed into the connector member body 91.

The opening 97 may include internal geometry such that it guides the connector member 80 toward the hook portion 96 as the connector member end 82 (or 84) is inserted further into the opening 97. For instance, the interior surface of the opening 97 may be angled so that the surfaces of inner walls of the opening 97 force the connector member 80 downward as the end 82 (or 84) travels deeper into the opening 97.

Referring to FIGS. 9-10, after the bone fixation construct 10A is implanted, the connector assembly 70A may be installed in the construct. According to a non-limiting example of an installation process, one of the hook members 90 may be delivered to the site of the construct through a minimally invasive surgical opening, positioned proximate a predetermined portion of one of the elongate members 30, and hooked onto the elongate member 30 using a tool (not shown) that may be similar to, for example, the implant head inserter 400 (shown in FIGS. 15A-15D), such that the elongate member 30 is positioned completely within the receptacle 95. Using the same tool (not shown) or another tool (not shown) the connector member 80 may be delivered to the installation site of the hook member 90 and the end 82 (or 84) may be inserted into the opening 97 in the hook member 90. The fastener 92 may be rotated using, for example, a screw driver (not shown) to drive the fastener 92 toward the hook portion 96, thereby contacting and forcing the connector member 80 against the elongate member 30 and forcing the elongate member downward and inward in the hook member body 91, against the inner and lower surfaces of the receptacle 95. As illustrated, the hook portion 96 may be shaped so as to prevent removal of the elongate body 30 from the hook member body 91 without first releasing the fastener 92 and/or removing the connector member 80.

The second hook member 90 may be delivered to the site of the connector assembly 70A and attached to the end 84 (or 82) of the connector member 80 (via opening 97 in the hook member 90) substantially simultaneously with attachment to the second elongate member 30 (via receptacle 95). Alternatively, the second hook member 90 may be attached to the second elongate member 30 and rotated about the elongate member to receive and insert the connector member 80 into the opening 97 of the second hook member 90. Once installed in the desired position, the second fastener 92 may be tightened to securely lock the connector member 80 and elongate member 30 in the hook member 90.

Figure 11:
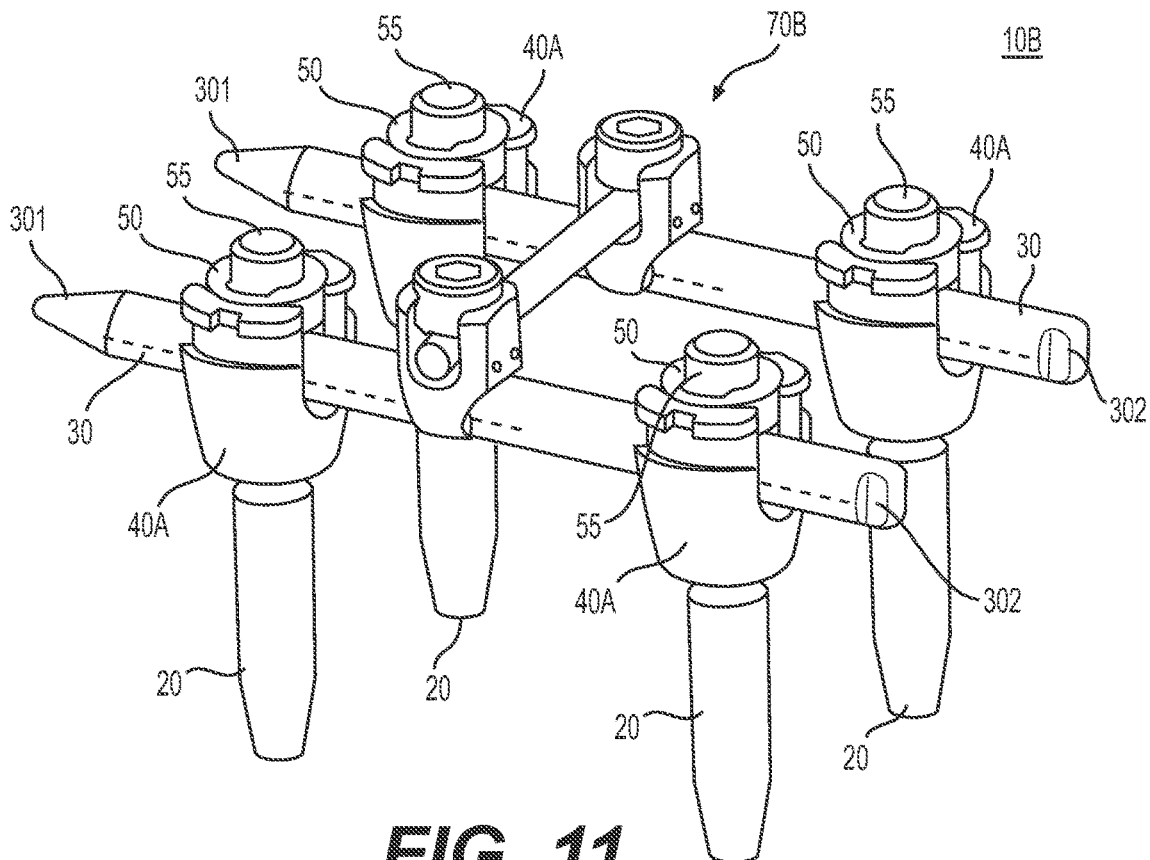
FIG. 11 shows yet another exemplary embodiment of a bone fixation construct, according to the principles of the disclosure.

FIG. 11 shows yet another exemplary embodiment of a bone fixation construct 10B. The bone fixation construct 10B may include substantially the same elements as the bone fixation construct 10A (shown in FIG. 9), except that the construct 10B includes a connector assembly 70B in lieu of the connector assembly 70A.

Figures 12, 13:
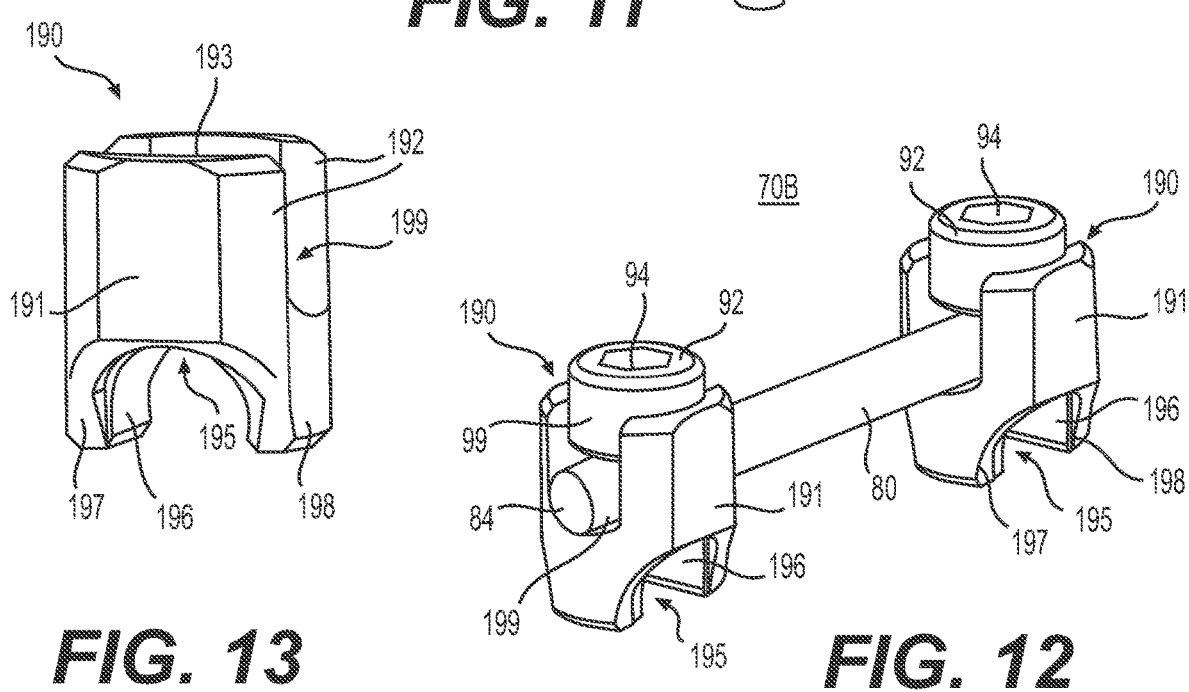
FIG. 12 shows another exemplary embodiment of a connector assembly, according to the principles of the disclosure.
FIG. 13 shows an exemplary embodiment of a hook member that may be included in the connector assembly of FIG. 12.

FIG. 12 shows a perspective view of the connector assembly 70B that may be introduced to the bone fixation construct 10B through an MIS opening to add stability to the construct, while minimizing damage to supporting anatomical structures. As seen in FIG. 12, the connector assembly 70B is a low profile structure that may easily attach to pre-existing elongate members.

FIG. 13 shows an example of a clip member 190 that may be included in the connector assembly 70B.

Referring to FIGS. 11-13, the connector assembly 70B may include a pair of clip members 190, a pair of fasteners 92 and the connector member 80. The clip member(s) 190 may include a clip member body 191 and a clamp 196. The clamp 196 may include, for example, a spring clamp housed within an external collet, such that when the clamp 196 is pushed onto an elongate member 30, the external collet pushes on the spring forks, keeping the clip member 190 locked to the elongate member 30. The clip member body 191 may include a pair of upwardly extending arms 192 and a pair of downwardly extending arms 197, 198. The upwardly extending arms 192 of the clip member body 191 may extend longitudinally in a superior direction and include an interior, an exterior, and upper surfaces. The interior of the upwardly extending arms 192 may include a threading (not shown) and form an opening 193 to receive and engage a corresponding threading on the cap 92. The arms 192 form a slot 199 therebetween that is configured to receive and hold the connector member 80, as illustrated in FIGS. 11 and 12.

The downwardly extending arms 197, 198 may extend longitudinally in an inferior direction and include an interior, an exterior, and lower surfaces. The interior of the downwardly extending arms 197, 198 may include a receptacle (not shown) formed by inner walls of the clip member body 191 and extending arms 197, 198. The receptacle (not shown) may include an opening in the superior direction, such that when the clamp 196 is installed therein, the connector member 80 may contact and press upon the upper surface (not shown) of the clamp 196, thereby forcing the clamp 196 to compress and reduce the diameter of the opening between the extending arms 197, 198. In this regard, the interior of the clip member body 191 may be hollowed along its longitudinal axis, providing an unobstructed pass-through from the opening 193 and downward through the slot 195.

The interior of the extending arms 197, 198 may include channels (not shown) or cut-outs (not shown) that are configured to receive and hold portions of the clamp 196. The arms 197, 198 form a slot 195 therebetween that is configured to receive and hold the elongate member 30, as illustrated in FIG. 11. The channels (not shown) or cut-outs (not shown) may be formed to have a gradient angle such that when the clamp 196 is pressed (for example, by the connector member 80 under force of the cap 92), the side walls of the clamp 196 are forced inward by the interior walls of the extending arms 197, 198, toward the center point of the slot 195. The channel formed by the slot 195 may be substantially orthogonal to the channel formed by the slot 199.

Referring to FIGS. 11-12, after the bone fixation construct 10B is implanted, the connector assembly 70B may be installed in the construct. According to a non-limiting example of an installation process, one of the clip members 190 (with the clamp 196) may be delivered through a MIS opening to the site of the construct, positioned proximate a predetermined portion of one of the elongate members 30, and clipped onto the elongate member 30 using a tool (not shown), which may be similar to the implant head inserter 400 (shown in FIGS. 15A-15D), such that the slot 195 is positioned on and envelopes the diameter of the elongate member 30. The process may be repeated for the second clip member 190.

The fasteners 92 may be pre-installed in the clip members 190, and positioned so as to form sufficient space in the slots 199 to allow the connector member 80 to pass there-through and be installed in the clip members 190.

Once the clip members 190 are in place, using the same tool (not shown), or another tool (not shown), the connector member 80 may be delivered to the installation site of the clip members 190 and the connector member 80 may be passed through the slot 199 of one of the clip members 190 and positioned with the end 82 (or 84) in the slot 199 of the other clip member 190, as seen in FIG. 12. The fasteners 92 may be rotated using, for example, a screw driver (not shown) to drive the fastener 92 against the connector member 80, thereby forcing the connector member 80 against the upper surface (not shown) of the clamp 196, forcing the clamp 196 to compress around and secure to the elongate member in the slot 195.

Alternatively, the connector assembly 70B may be pre-assembled with the fasteners 92 partially tightened so as to keep the connector assembly 70B intact during insertion, delivery, positioning and mounting of the connector assembly 70B to the elongate members 30, but sufficiently loose to allow for manipulation of the connector member 80 and/or installation of the clip members 190 onto the corresponding elongate members 30. Once the connector assembly 10B is mounted and positioned in the desired locations on the elongate members 30, the fasteners 92 may be tightened and, thereby, the connector assembly 70B may be locked and secured in the bone fixation construct 10B.

Figures 14A, 14B, 14C:
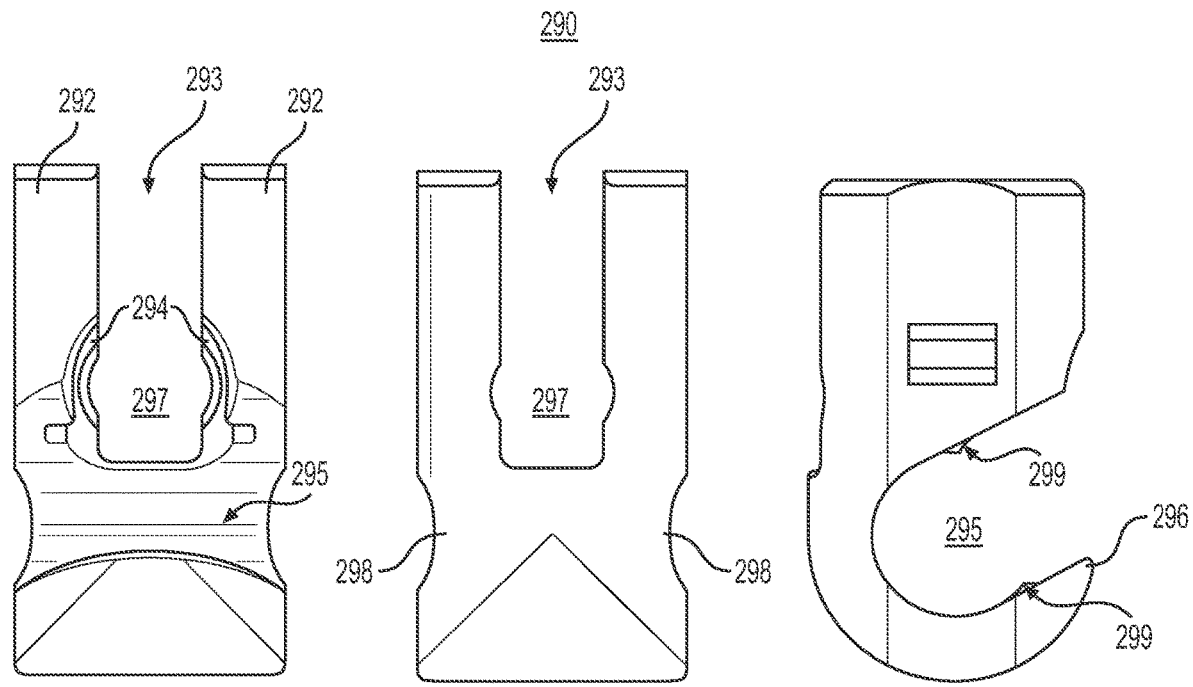
FIGS. 14A-14D show yet another exemplary embodiment of a hook member, according to the principles of the disclosure.
Figure 14D:
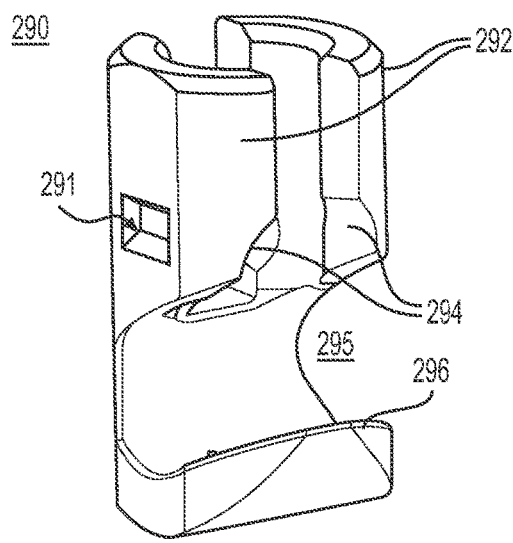

FIGS. 14A-14D show yet another exemplary embodiment of a hook member 290 that may be included in a connector assembly 70C (shown in FIG. 18) of a bone fixation construct 10C. FIG. 14A shows a front (or back) view of the hook member 290; FIG. 14B shows a back (or front) view of the hook member 290; FIG. 14C shows a side view of the hook member 290; and, FIG. 14D shows a perspective view of the hook member 290.

Referring to FIGS. 14A-14D, the hook member 290 comprises a hook member body that may include an opening 293, a receptacle 295, a hook portion 296, and an opening 297. The hook member body may include a guide(s) 298 that may facilitate alignment of the hook member during installation by, for example, the implant head inserter 400 (shown in FIGS. 15A-15D). The hook member 290 may include a tool engagement portion 291 that may be contacted and engaged with, for example, the implant head inserter 400 (shown in FIGS. 15A-15D) to assist the implant head inserter 400 to grasp and hold the hook member 290 during installation.

The opening 293 may be configured to receive and engage the fastener 92. The opening 293 may include, for example, a stab incision. The opening 293 may include a threading that may engage a corresponding threading on the fastener 92 and cause the fastener 92 to be screwed downward (or upward) when the fastener 92 is rotated with respect to the hook member body. The opening 293 may be formed by a pair of upwardly extending arms 292.

The receptacle 295 may be shaped to receive and securely hold the elongate member 30 (shown in FIG. 18) in the hook member body. The receptacle 295 may be configured to catch and hold the entirety of the width (or diameter) of the elongate member 30 in the hook member body. The receptacle 295 may include one or more capture members 299 that help to pre-lock and hold the elongate member 30 in the receptacle 295, preventing the hook member 290 from falling off once in place. The one or more capture members 299 may provide a user with tactile feel once the elongate member 30 is secured in the receptacle 295.

The hook portion 296 forms a lower part of the receptacle 295, and may be shaped to catch and aid in attaching and securing the hook member 290 to the elongate member 30. For instance, the hook portion 296 may include an upwardly inclined configuration to catch the elongate member 30, such that the hook member body will move upward with respect to the elongate member 30 as the elongate member 30 is moved deeper into the receptacle 295.

Figure 18:
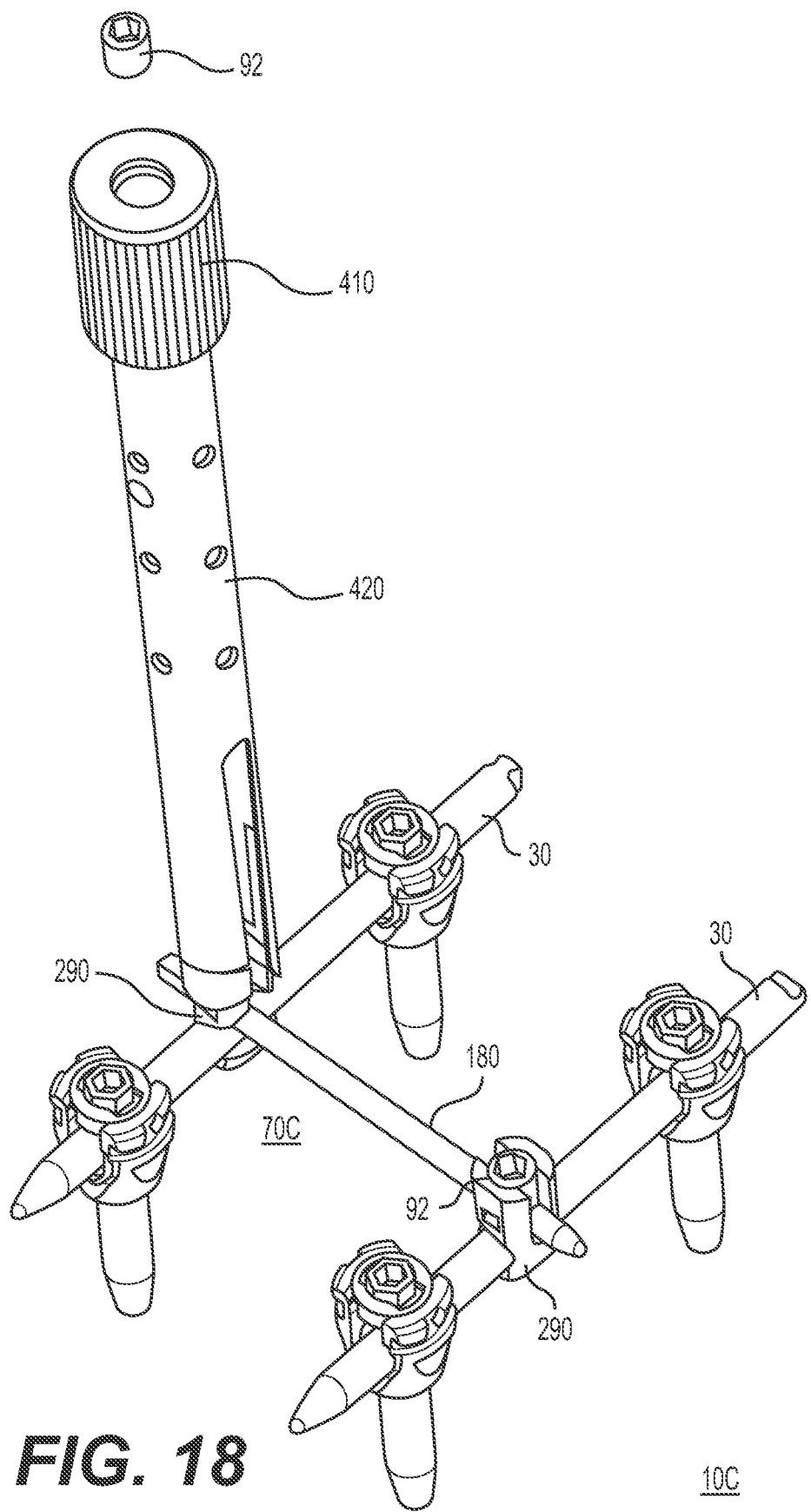
Figure 19:
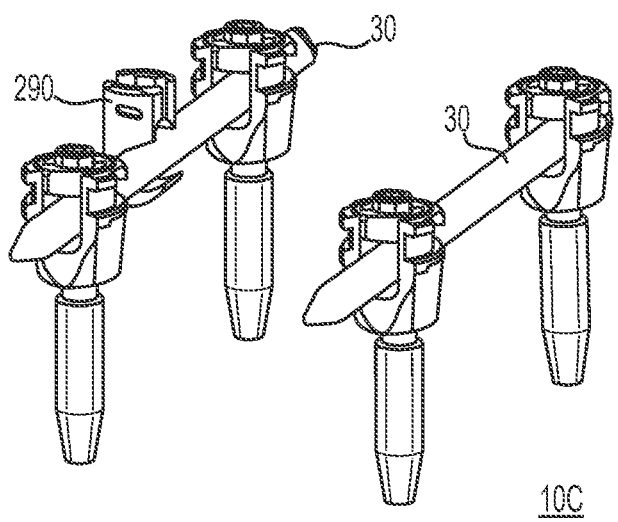
Figure 20:
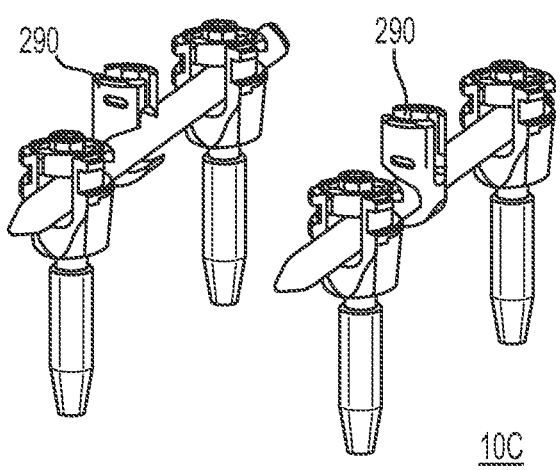
Figure 21:
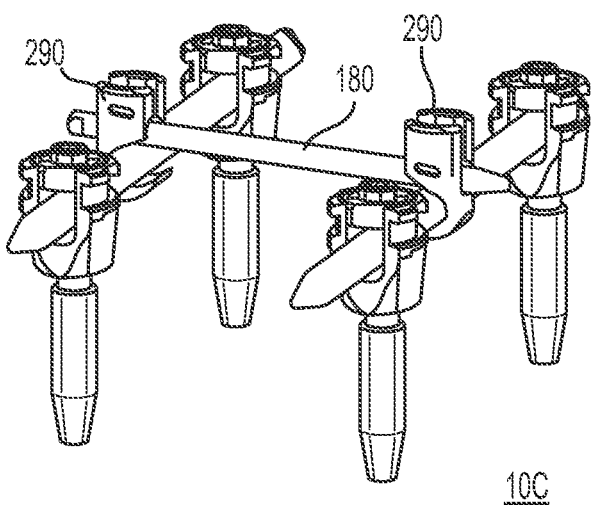
Figure 22:
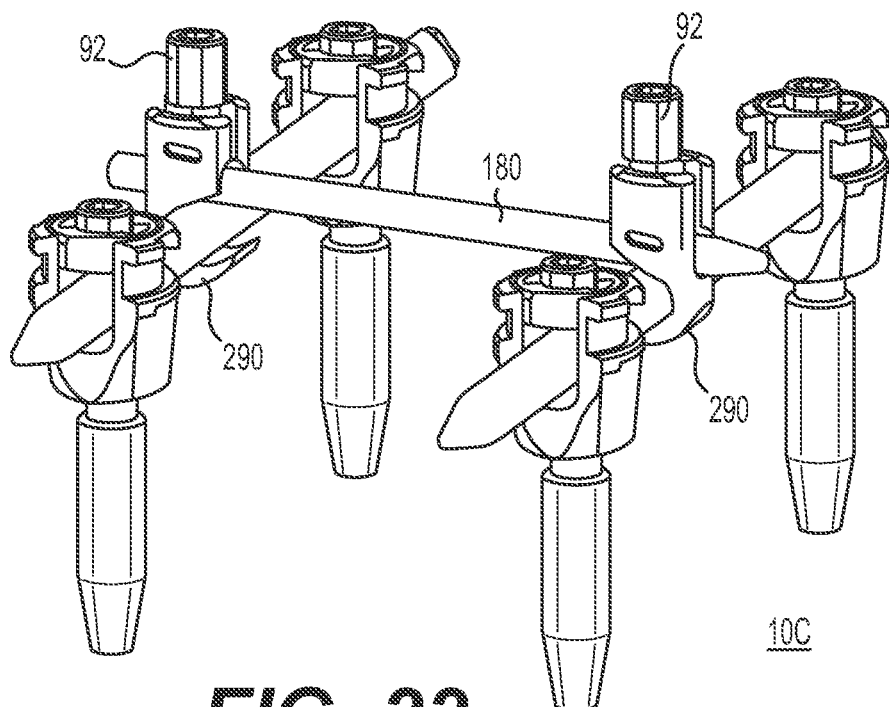
Figure 23:
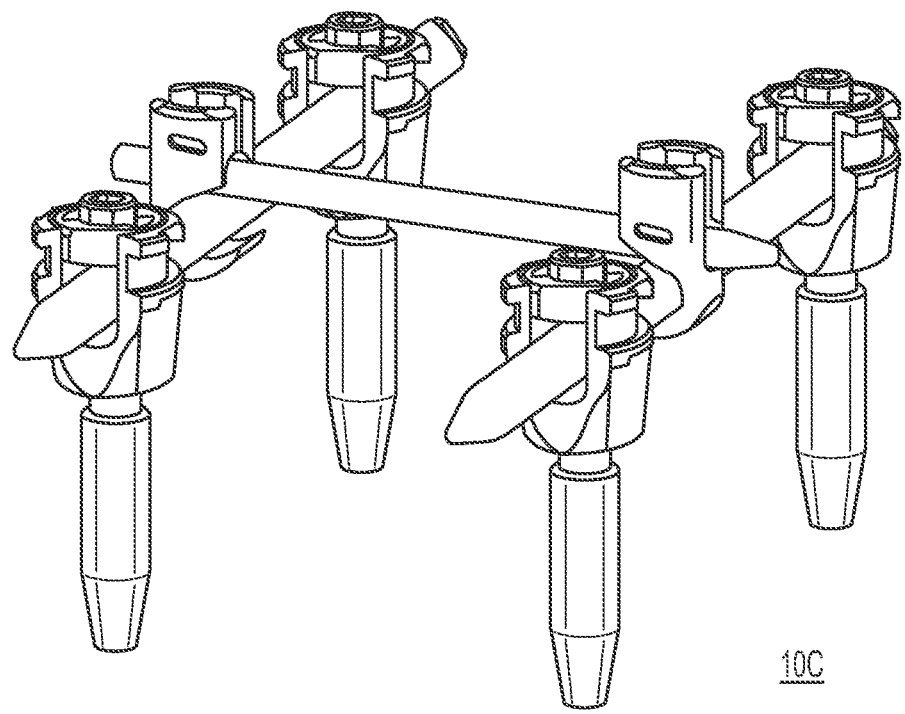

The opening 297 may be shaped to substantially match the shape of the connector member 180 (shown in FIG. 18). As seen in FIGS. 14A and 14B, the opening 297 may have a round shape that receives and holds a cylindrically-shaped connector member 180. The inner diameter of the opening 297 is greater than the outer diameter of the connector member 180. The inner diameter of the opening 297 extends into the receptacle 295, such that when the elongate member 30 is properly seated in the receptacle 295 and the connector member 180 is inserted into the opening 297, the connector member 180 may contact and force the elongate member 30 toward the hook portion 296 (or bottom surface of the receptacle 295) and inward toward the connector member body under force of the fastener 92. For instance, the connector member 180 may be forced against the elongate member 30 by operation of the fastener 92, which contacts the connector member 180 and forces the connector member 180 against the elongate member 30 as the fastener 92 is screwed into the connector member body.

The connector member 180 may be similar to the connector member 35 (shown in FIG. 1), the elongate member 30 (shown in FIG. 1), the connector member 80 (shown in FIG. 9), or the like. The connector member 180 may include, for example, an elongate rod (shown in FIG. 18), a pin (not shown), a brace (not shown), a spring (not shown), a cord (not shown), a resilient extension (not shown), or any other stabilization device that may be secured in the hook members 290 to provide stabilization. The connector member 180 may include attributes that may be selected based on, for example, variations in anatomy. For instance, the connector member 180 attributes may be selected from various lengths, widths, shapes, or the like, depending on the particular application.

The opening 297 may include a geometry such that it guides the connector member 180 toward the hook portion 296 as the end of the connector member 180 is inserted further into the opening 297. For example, the interior surface of the opening 297 may include tapered sections 294, which may be angled so that the surface of the tapered sections 294 forces the connector member 180 toward the center and/or downward as the end of the connector member 180 travels deeper into the opening 297.

Figure 15A:
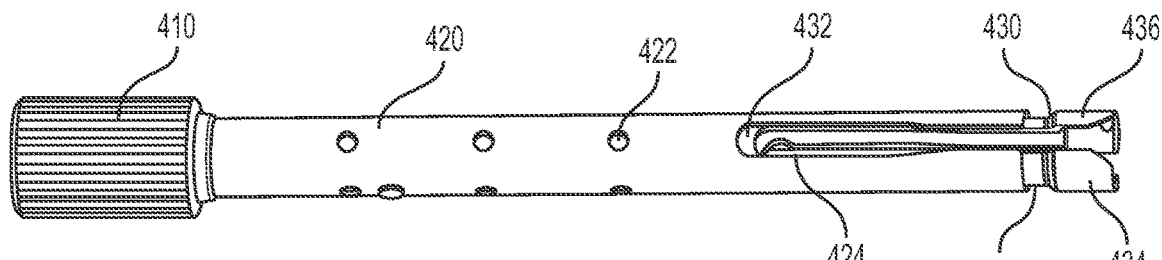
FIGS. 15A-15D show an example of an implant head inserter that may be used with the hook member of FIGS. 14A-14D.
Figure 15B:
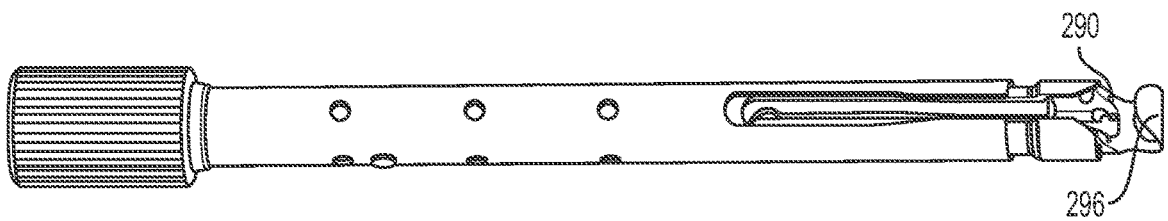
Figure 15C:
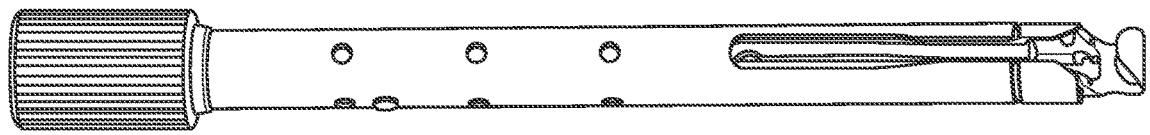
Figure 15D:
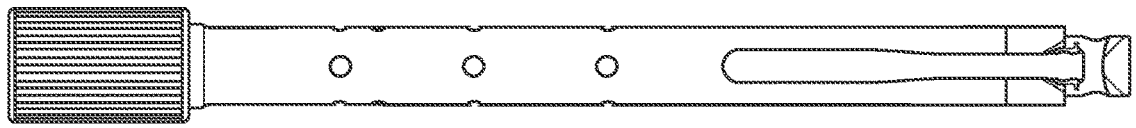

FIGS. 15A-15D show an example of an implant head inserter 400 that may be used with the hook member 290 to install the hook member 290 in a bone fixation construct 10C (shown in FIG. 18). FIG. 15A shows the implant head inserter 400 in an unlocked position; FIG. 15B shows the implant head inserter 400 in the unlocked position with a hook member 290 attached at the distal end; FIG. 15C shows the implant head inserter 400 in a locked position with the hook member 290 attached at the distal end; and, FIG. 15D shows another view of the implant head inserter 400 in the locked position with the hook member 290 attached at the distal end.

Referring to FIG. 15A, the implant head inserter 400 may include a handle 410, a sleeve 420, and an inner member 430. The inner member 430 may include a spring clamp that may be compressed by the sleeve 420 as the inner member 430 travels in the direction of the handle 410. Conversely, the sleeve 420 may release the inner member 430 as the inner member 430 travels in the direction away from the handle 410. The sleeve 420 may include a functional gap (or cutout) 424 formed between a pair of extending members, as seen in FIG. 15A, which may be configured to flex outward or inward as the inner member 430 travels toward and away from the handle 410.

The sleeve 420 may include a handle engagement portion (not shown) that attaches to the handle 410, allowing the handle 410 to rotate about the longitudinal axis of the sleeve 420. The handle 410 may be coupled to the inner member 430 and configured to drive the inner member 430 as the handle 410 is rotated. The sleeve may include one or more openings 422, which may show portions of the inner member 430.

The inner member 430 may include a substantially cylindrical body with a pair of extending members 434, 436 at its distal end 433. The extending members 434, 436 may be made of a memory-shape material (for example, a metal, a plastic, or the like, that is made to hold a predetermined shape, but compress under force) whereby the extending members 434, 436 expand away from each other as the distal end 433 moves out and away from the distal end of the sleeve 420. Conversely, the extending members 434, 436 compress toward each other as the distal end 433 moves into the sleeve 4320. The extending members 434, 436 may include a guide-contact portion (not shown) that contacts and engages the guide(s) 298 on the hook member 290 to properly align the hook member 290 during installation.

Referring to FIGS. 15B and 15C, the implant head inserter 400 may be configured into the unlocked position by, for example, turning the handle 401 in a predetermined direction, and a hook member 290 may be attached to the distal end 433 (shown in FIG. 15B). The implant head inserter 400 may then be operated to the locked position by, for example, turning the handle 410 in the opposite direction, thereby locking the hook member 290 at its distal end (shown in FIG. 15C). FIG. 15D shows another view of the implant head inserter 400 in the locked position with the hook member 290 attached at the distal end.

FIGS. 16-26 show yet another exemplary embodiment of a bone fixation construct 10C during a process of installing the construct in bone. The bone fixation construct 10C may include substantially the same elements as the bone fixation construct 10A (shown in FIG. 8) or 10B (shown in FIG. 11), except that the construct 10C includes a connector assembly 70C in lieu of the connector assembly 70A or 70B, respectively. The bone fixation construct 10C may be installed according to a process similar to that described above with respect to the bone fixation construct 10 (or 10A, or 10B), or any other process commonly used to implant constructs, as understood by those skilled in the art. Once the bone fixation construct 10C is installed, the connector assembly 70C may be installed, as described herein, thereby providing increased stability of the construct.

Figure 16:
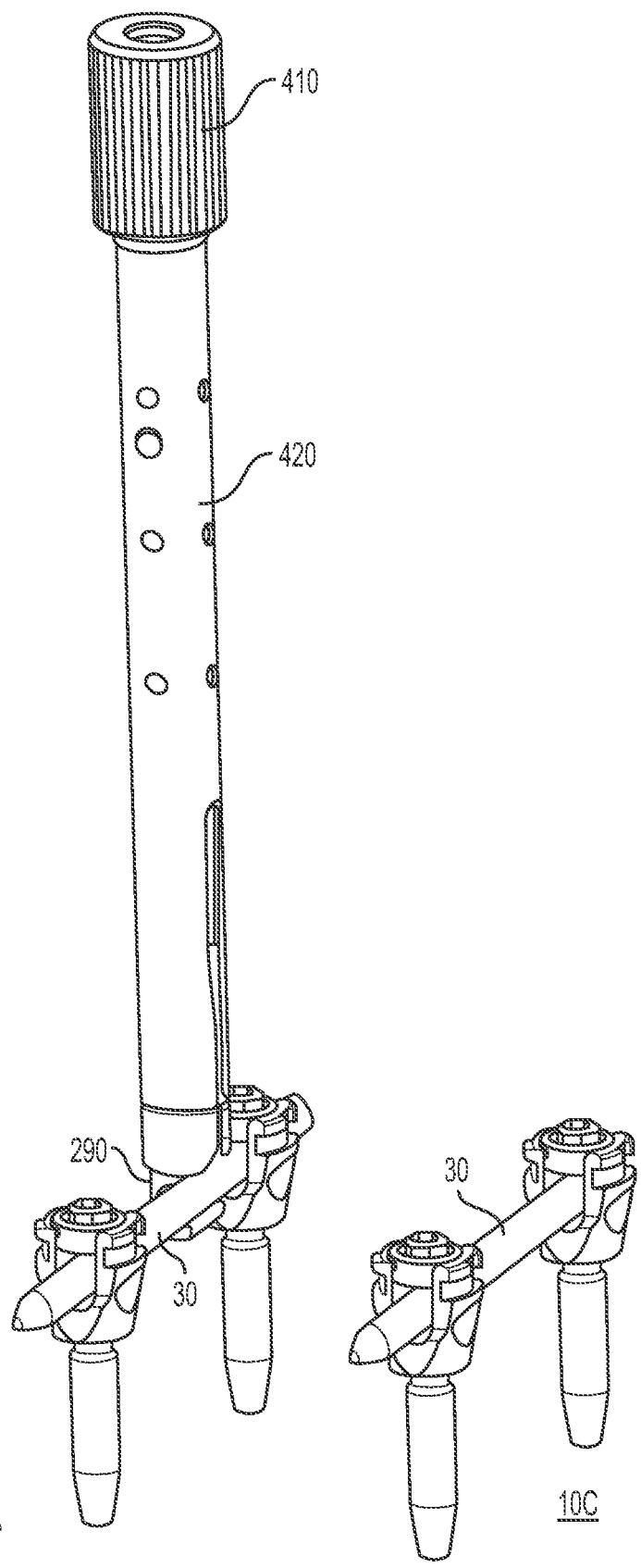
FIGS. 16-26 show yet another exemplary embodiment of a bone fixation construct during a process of installing the construct in bone.
Figure 17:
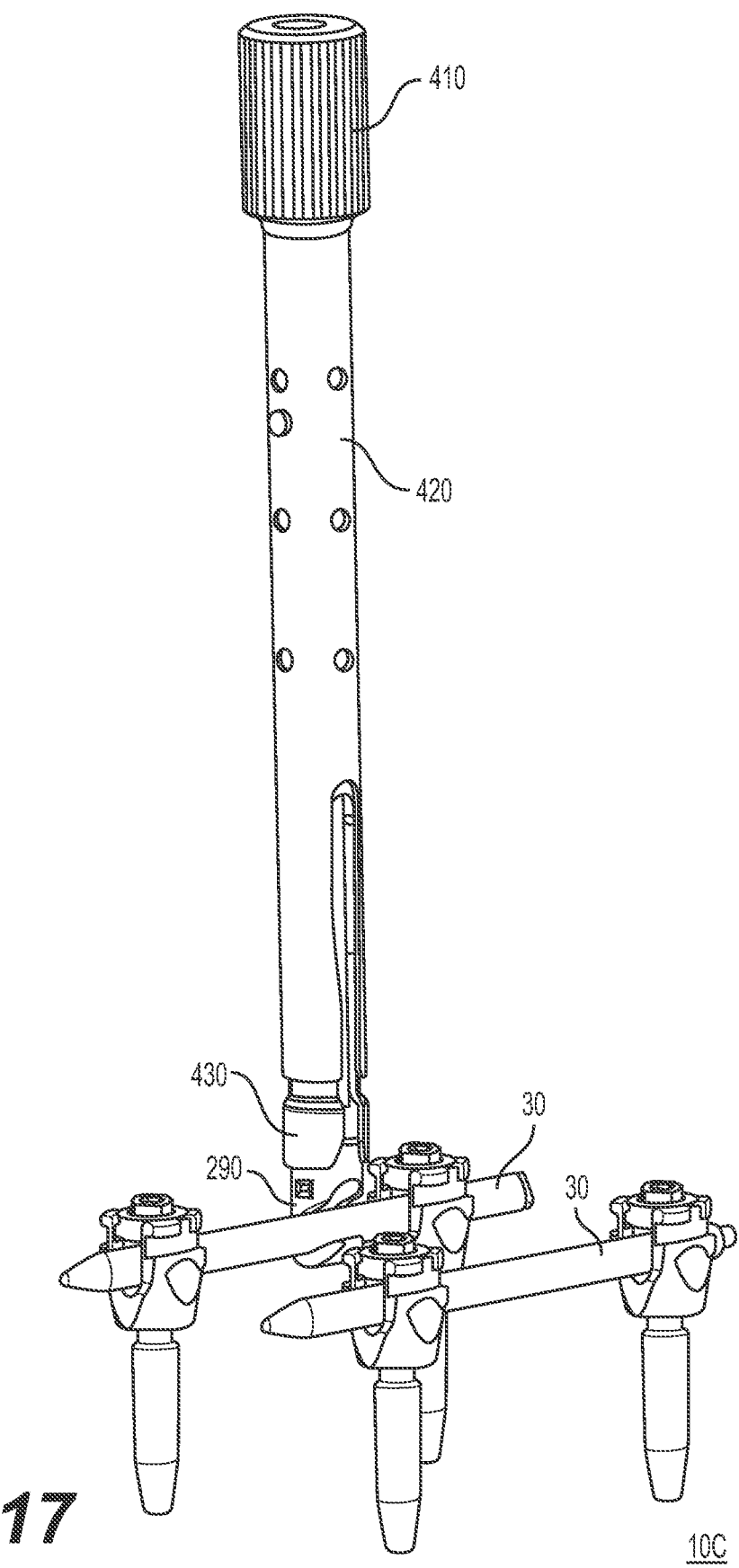

Referring to FIGS. 16-18, after the bone fixation construct 10C is implanted, the connector assembly 70C may be installed in the construct. According to a non-limiting example of an installation process, one of the hook members 290 may be delivered to the site of the construct through a minimally invasive surgical opening, positioned proximate a predetermined portion of one of the elongate members 30, and hooked onto the elongate member 30 using the implant head inserter 400 (shown in FIG. 16), such that the elongate member 30 is positioned completely within the receptacle 295. Once the hook member 290 is properly hooked on to the elongate member 30, such as, for example, when the elongate member 30 is within the receptacle 295 (shown in FIG. 14C) and caught by the capture member(s) 299, the handle 410 may be operated to extend the inner member 430, thereby releasing the hook member 290 (shown in FIG. 17).

FIG. 18 shows an example of inserting the fastener 92 into an inner channel of the sleeve 420 and inner member 430, so as to deliver the fastener 92 to the hook member 290 and install the fastener 92 into the hook member 290, thereby securing the connector member 180 in the hook member 290, and securing the connector member 180 and hook member 290 to the elongate member 30.

Figure 25:
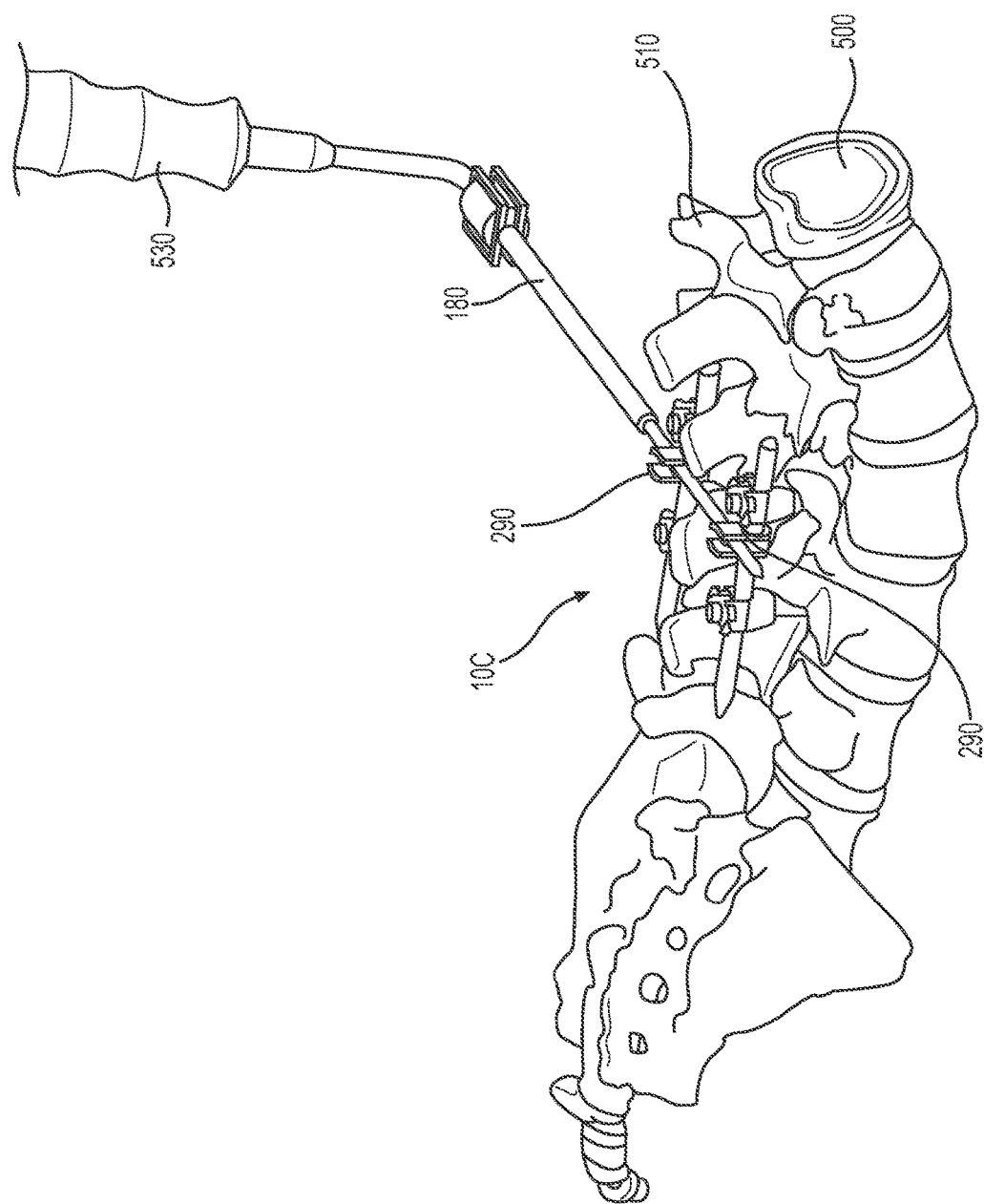

FIGS. 19-26 show the various stages of installation of the connector assembly 70C in the bone fixation construct 10C. Initially, using the implant head inserter 400, a first hook member 290 may be attached to one of the elongate members 30 (shown in FIG. 19). The process may then be repeated for the second hook member 290, attaching it to the second elongate member 30 (shown in FIG. 20). With both hook members 290 attached to respective elongate members 30, the connector member 180 may be installed in the hook members 290 using, for example, the rod introduction instrument 530 to insert and position the connector member 180 in the hook members 290 (shown in FIGS. 21 and 24-25). The connector member 180 may include a frustoconical end which may facilitate introduction of the connector member 180 through various tissue including ligaments and bone. For example, FIGS. 25 and 26 show connector element 180 being passed through a spinous process of a vertebra during installation. It is contemplated that this is achieved by making the end of the connector member 180 sharp enough to penetrate tissue or to use a separate instrument to create an initial through bore for the connector member 180 to travel through during installation. Once the connector member 180 is properly positioned in the hook members 290, fasteners 92 may be installed in the hook members 290, thereby securing the connector member 180 and hook members to the elongate members 30, and bone fixation construct 10C (shown in FIGS. 22-23 and 26).

FIG. 26 shows an example of the bone fixation construct 10C, including connector assembly 70C implanted in a pair of adjacent vertebrae 510 of a spine 500, according to the principles of the disclosure. As seen, the bone fixation construct 10C provides a low profile structure with increased stability.

Figure 27:
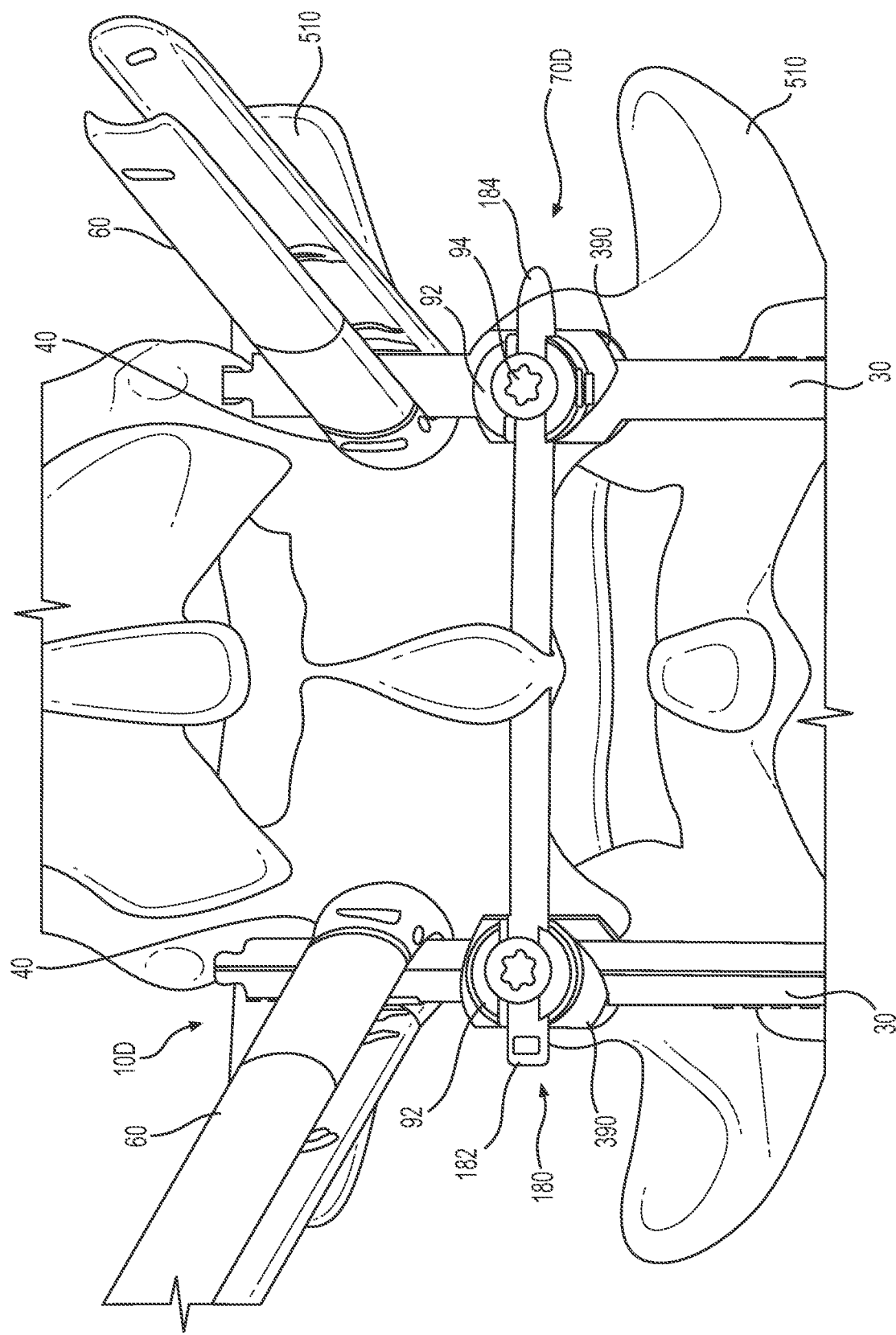
FIGS. 27-43 show yet another exemplary embodiment of a bone fixation construct during a process of installing the construct in bone.

Referring to FIGS. 27-43, another exemplary embodiment of a bone fixation construct 10D and an exemplary method of implanting such construct according to the principles of the disclosure will be described. With reference to FIGS. 27 and 30, the bone fixation construct 10D is similar to the previous embodiments and includes a plurality of the bone fasteners 20, a pair of elongate members 30, a plurality of couplers 40, 40A, a plurality of caps 50, and a connector assembly 70D. In the illustrated embodiment, the bone fixation construct 10D includes a pair of couplers 40 with an extender 60 similar to those described with respect to FIG. 1 and a pair of couplers 40A which do not include extenders. It is understood that any desired combination of couplers 40, 40A may be utilized in the bone fixation construct 10D. Each coupler 40, 40A is configured to receive one of the caps 50 which contacts and secures the elongate member 30 in the respective coupler 40, 40A. The contact surface (not shown) of the caps 50 may be shaped to substantially match the outer shape of the elongate member 30, thereby increasing the surface contact and coefficient of static friction between the elongate member 30 and bottom surface of the caps 50.

Figure 28:
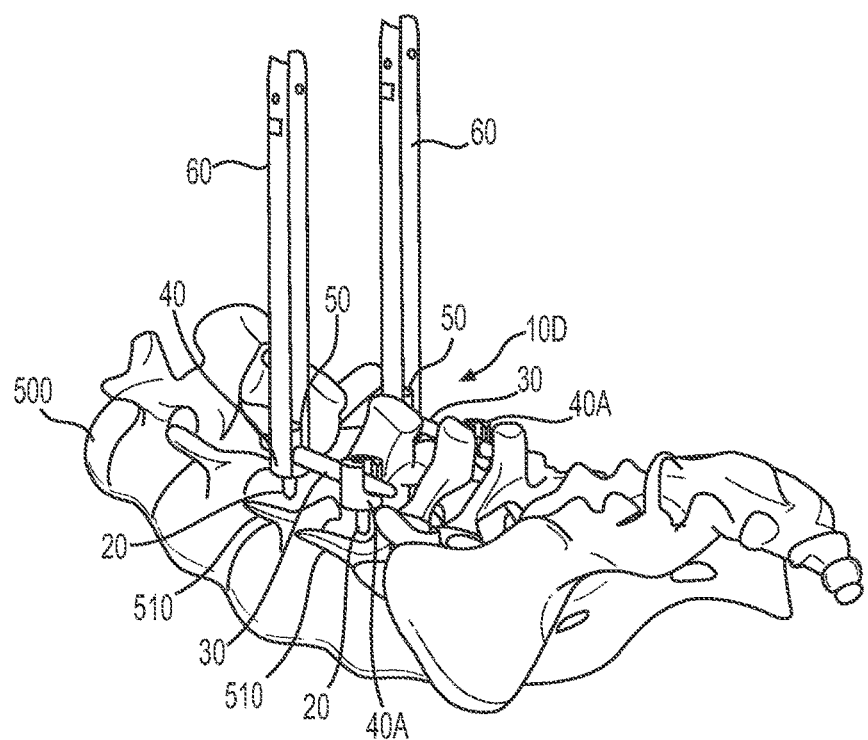

The bone fasteners 20, elongate members 30, couplers 40, 40A, and caps 50 may be installed according to a process similar to that described above or any other process commonly used to implant constructs, as understood by those skilled in the art. Once the bone fasteners 20, elongate members 30, couplers 40, 40A, and caps 50 are installed as illustrated in FIG. 28, the connector assembly 70D may be installed, as described herein, thereby providing increased stability of the construct.

Referring to FIGS. 27, 30 and 32-34, the connector assembly 70D is similar to the previous embodiment and includes a pair of hook members 390 and a connector member 180. The connector member 180 is similar to the previous embodiment and may include, for example, an elongate rod (shown in FIG. 27), a pin (not shown), a brace (not shown), a spring (not shown), a cord (not shown), a resilient extension (not shown), or any other stabilization device that may be secured in the hook members 390 to provide stabilization. The connector member 180 may include attributes that may be selected based on, for example, variations in anatomy. For instance, the connector member 180 attributes may be selected from various lengths, widths, shapes, or the like, depending on the particular application. The connector member 180 may be secured at each end 182, 184 to the hook members 390 by means of fasteners 92 similar to those described above.

Figure 33:
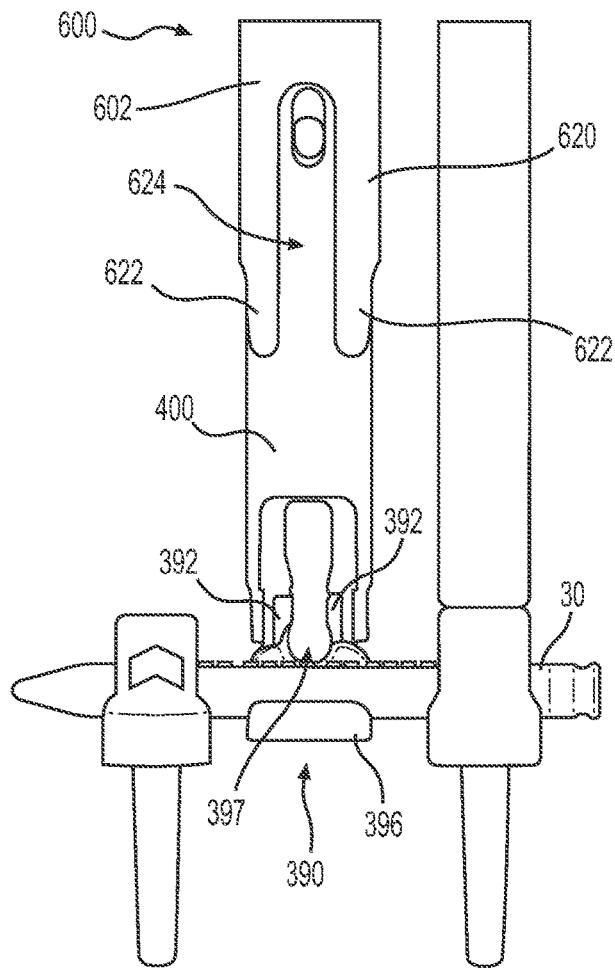

The hook members 390 are similar to the previous embodiment with each hook member 390 comprising a hook member body including an opening 393 formed between a pair of upwardly extending arms 392, a receptacle 395, a hook portion 396, and an opening 397. The primary distinction from the hook member 290 of the previous embodiment is that the hook member body of the present embodiment tapers to the upwardly extending arms 392, as seen in FIG. 33, such that the arms 392 are easily received in the implant head inserter 400.

The opening 393 is configured to receive and engage the fastener 92. The opening 393 may include, for example, a stab incision. The opening 393 may include a threading that may engage a corresponding threading on the fastener 92 and cause the fastener 92 to be screwed downward (or upward) when the fastener 92 is rotated with respect to the hook member body. The receptacle 395 is shaped to receive and securely hold the elongate member 30 in the hook member body as in the previous embodiments. The hook portion 396 forms a lower part of the receptacle 395, and may be shaped to catch and aid in attaching and securing the hook member 390 to the elongate member 30 as in the previous embodiments. The opening 397 may be shaped to substantially match the shape of the connector member 180, for example, the opening 397 may have a round shape that receives and holds a cylindrically-shaped connector member 180. In at least one embodiment, the inner diameter of the opening 397 is greater than the outer diameter of the connector member 180. The inner diameter of the opening 397 extends into the receptacle 395, such that when the elongate member 30 is properly seated in the receptacle 395 and the connector member 180 is inserted into the opening 397, the connector member 180 may contact and force the elongate member 30 toward the hook portion 396 and inward toward the connector member body under force of the fastener 92. For instance, the connector member 180 may be forced against the elongate member 30 by operation of the fastener 92, which contacts the connector member 180 and forces the connector member 180 against the elongate member 30 as the fastener 92 is screwed into the connector member body.

The connector member 180 may be similar to the connector member 35 (shown in FIG. 1), the elongate member 30 (shown in FIG. 1), the connector member 80 (shown in FIG. 9), or the like. The connector member 180 may include, for example, an elongate rod (shown in FIG. 27), a pin (not shown), a brace (not shown), a spring (not shown), a cord (not shown), a resilient extension (not shown), or any other stabilization device that may be secured in the hook members 390 to provide stabilization. The connector member 180 may include attributes that may be selected based on, for example, variations in anatomy. For instance, the connector member 180 attributes may be selected from various lengths, widths, shapes, or the like, depending on the particular application.

Figure 29:
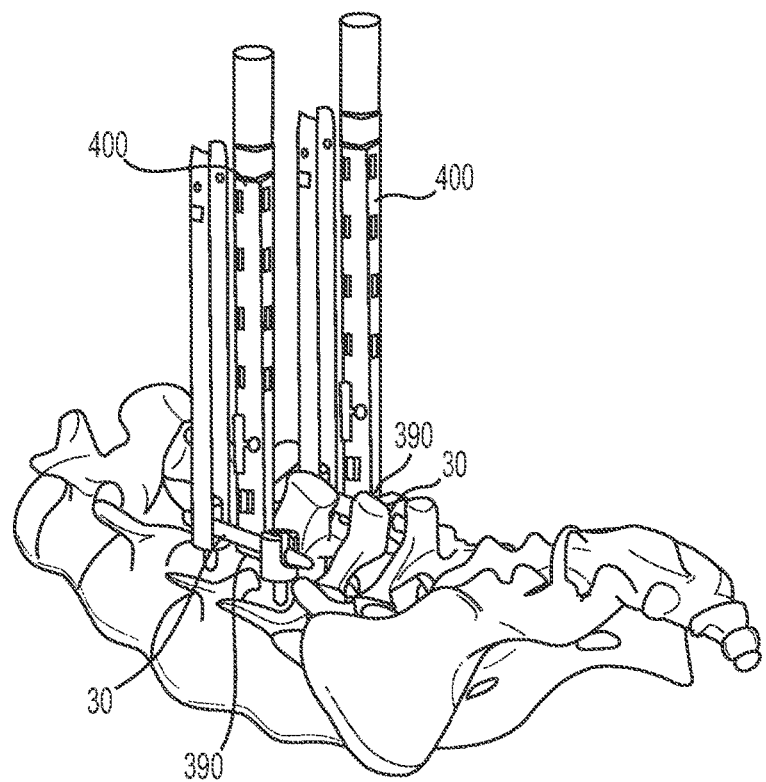
Figure 30:
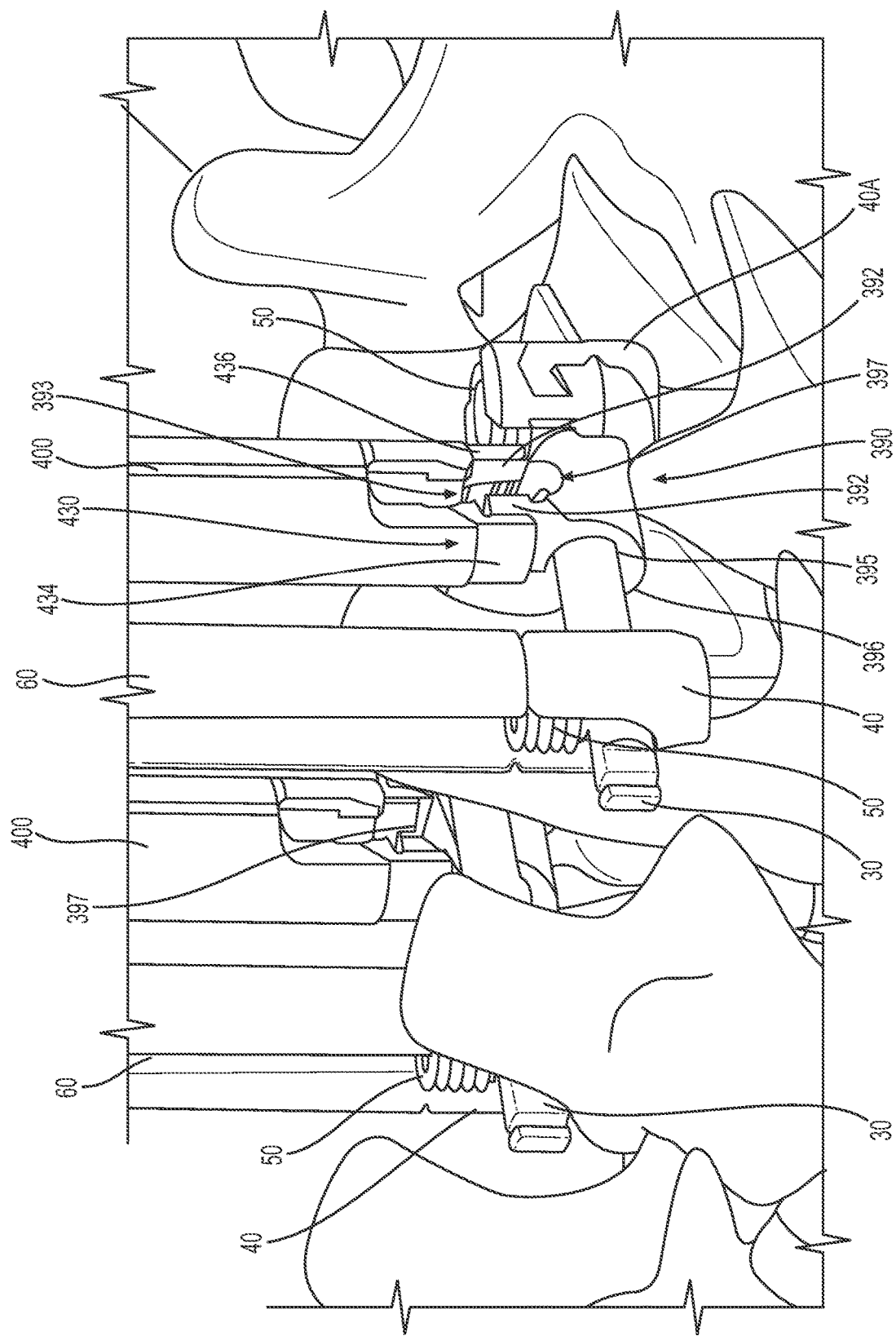
Figure 31:
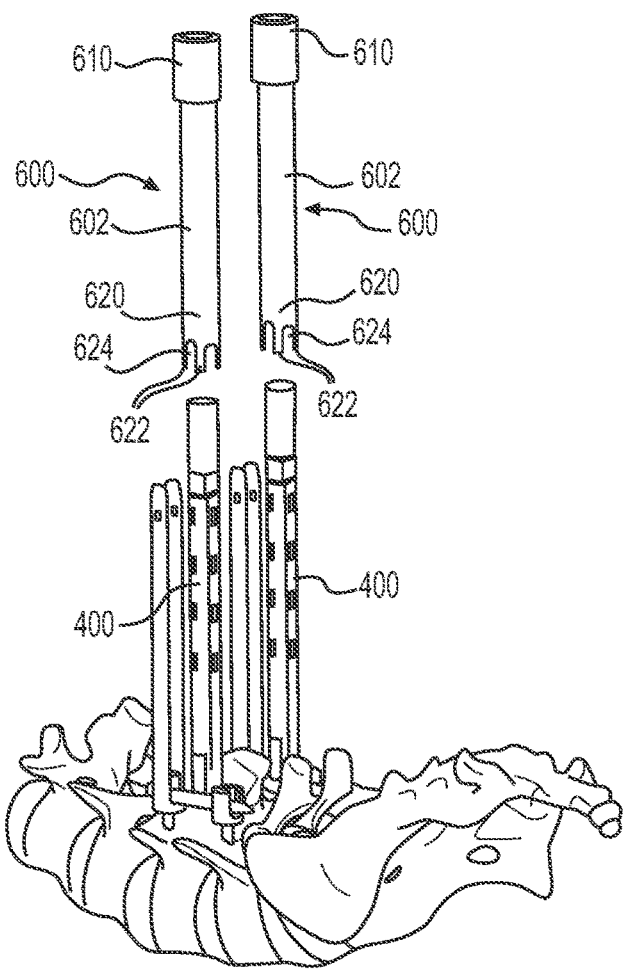
Figure 32:
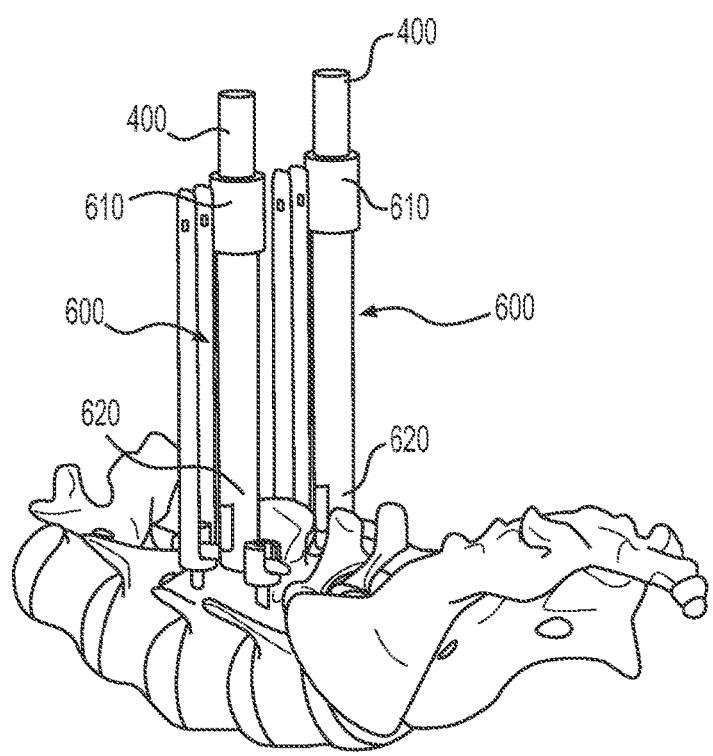

Referring to FIGS. 29-30, according to a non-limiting example of an installation process, each of the hook members 390 may be delivered to the site of the construct through a MIS opening, positioned proximate a predetermined portion of one of the elongate members 30, and hooked onto the elongate member 30 using the implant head inserter 400 (similar to that shown in FIG. 16), such that the elongate member 30 is positioned completely within the receptacle 395. Once each of the hook members 390 is properly hooked on to the elongate member 30, such as, for example, when the elongate member 30 is within the receptacle 395, a preliminary locking instrument 600 is positioned relative to each implant head inserter 400 to temporarily maintain the position of the hook member 390 and prevent disengagement thereof from the respective elongate member 30.

Figure 34:
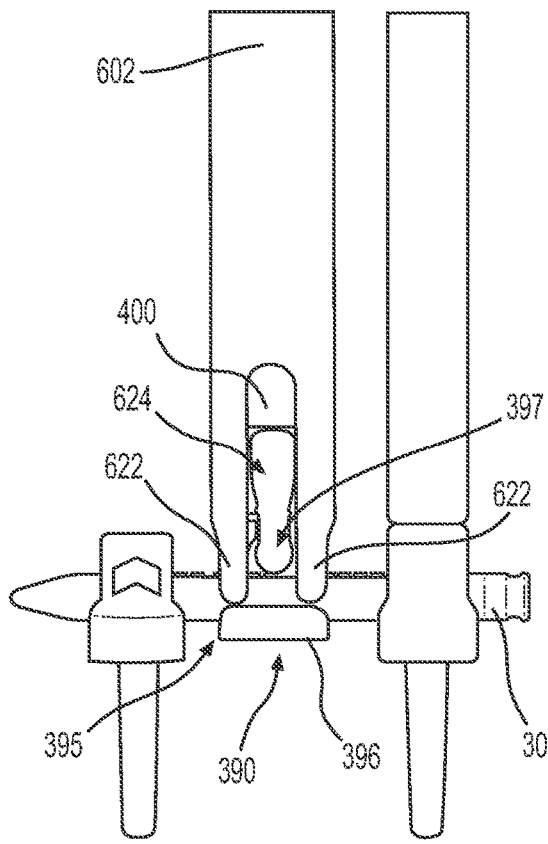

Referring to FIGS. 31-34, in the present embodiment, each preliminary locking instrument 600 includes a hollow locking sleeve 602 extending from an open proximal end 610 to a distal end 620. The distal end 620 of the locking sleeve 602 includes a plurality of fingers 622 circumferentially spaced from one another by a plurality of openings 624. The locking sleeve 602 is configured to slide over the outer surface of the implant head inserter 400 such that the distal end 620 may be advanced toward the hook member 390 as illustrated in FIGS. 33 and 34. With the preliminary locking instrument 600 fully advanced, the distal end 620 of the locking sleeve 602 extends about the hook member arms 392 with fingers 622 extending on opposed sides of the elongate member 30 and the elongate member 30 passing through two of the openings 614. The fingers 612 may extend proximate the hook portion 396 such that the elongate member 30 is prevented from moving out of the receptacle 395.

Figure 35:
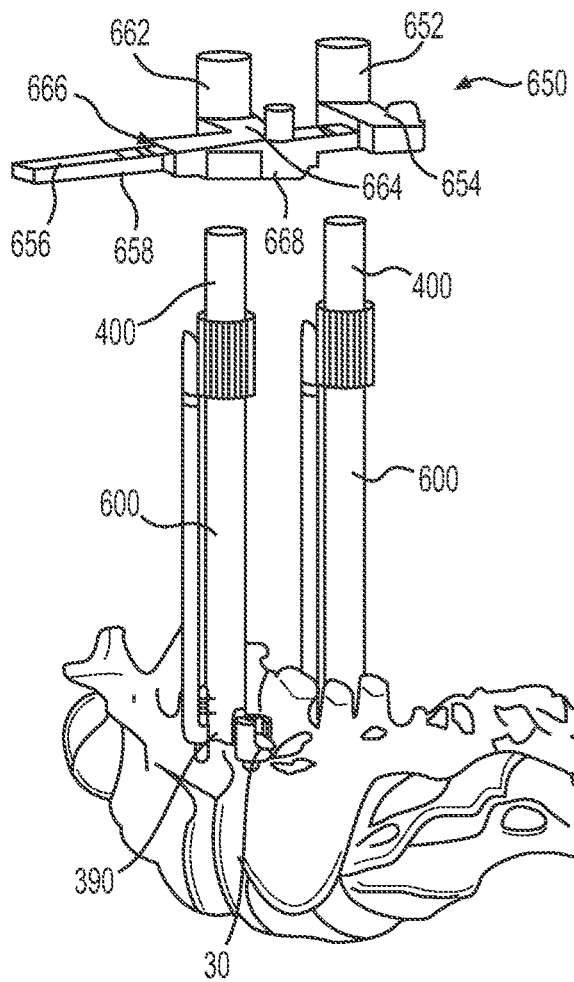
Figure 36:
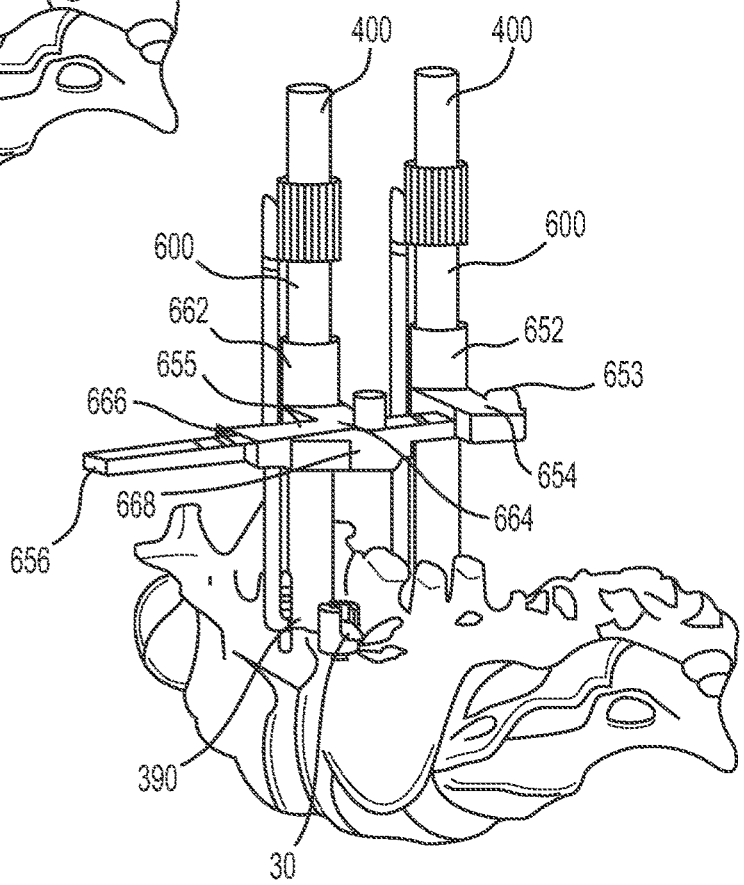
Figure 37:
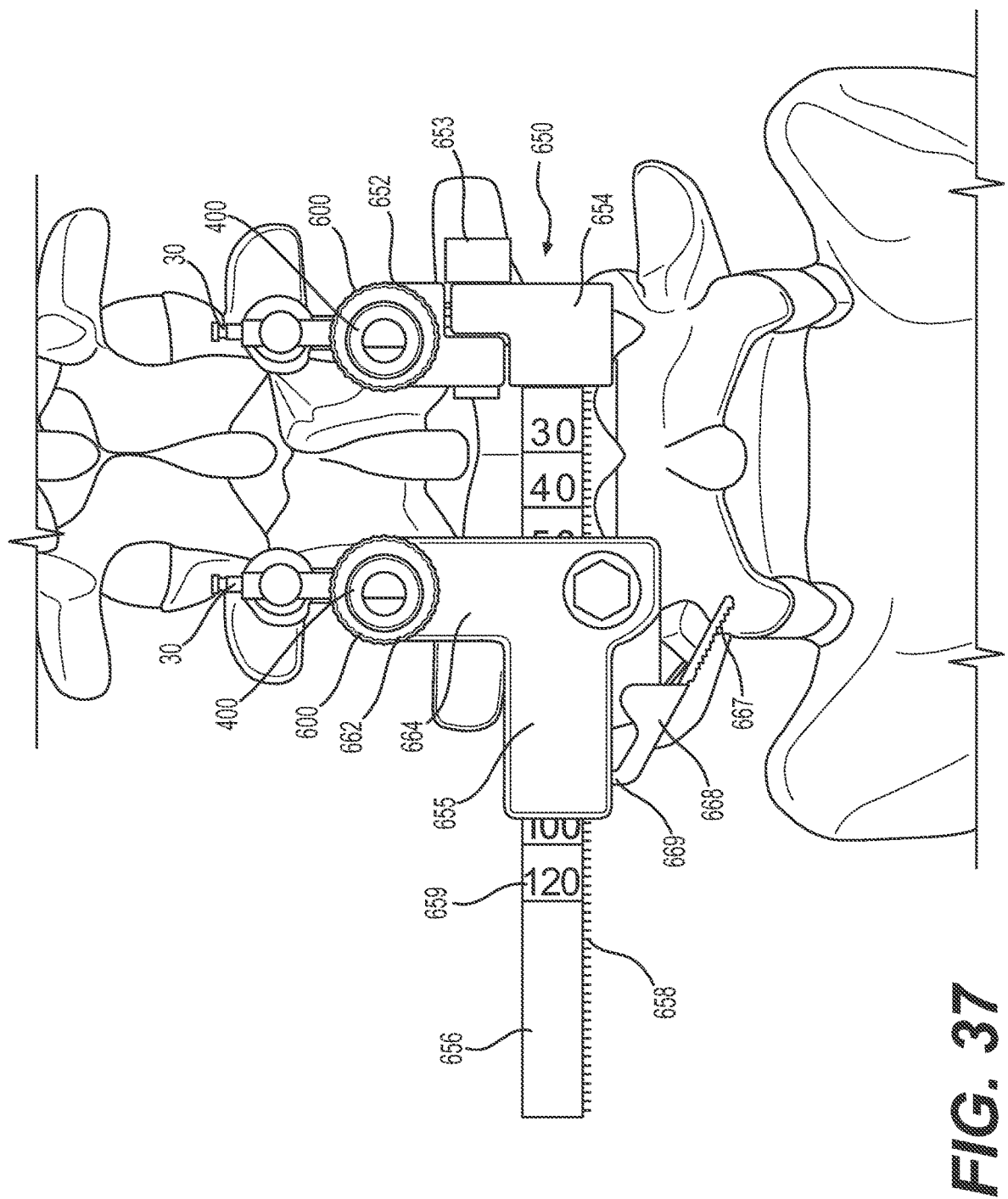

Turning to FIGS. 35-37, a compressor assembly 650 is positioned over the locking sleeves 602. The compressor assembly 650 includes a first tube 652 configured to slide over a first of the sleeves 602 and a second tube 662 configured to slide over the other sleeve 602. The first tube 652 is pivotally connected to a first body 654 via a pivot pin 653. A slide bar 656 extends from the first body 654 such that the first tube 652, the first body 654 and the slide bar 656 define a generally right angle. The slide bar 658 includes a series of teeth 658 defined along one edge thereof and configured to be engaged by a pivotal pawl 668 associated with the second tube 662, as will be described in more detail hereinafter. In the illustrated embodiment, the slide bar 656 has a scale 659 along a surface thereof. The scale 659 may be used to determine a desired size of the connector member 180.

The second tube 662 has a second body 664 extending therefrom. The second body 664 includes a slide bar receiving portion 665 with a through opening 666 extending therethrough. The slide bar receiving portion 665 extends parallel to the slide bar 656 which extends through the opening 666. A pawl 668 is pivotally connected to the second body 664 and is biased such that a tip 669 of the pawl 668 is normally biased into engagement with the teeth 658 along the slide bar 656. An opposite end 667 of the pawl 668 may be pressed to disengage the tip 669 from the teeth 658. In the illustrated embodiment, the tip 669 is configured such that it may ratchet along the teeth 658 when the first and second tubes 652, 662 are moved toward one another, but remains engaged with the teeth 658 and prevents separation when a force is applied to separate the first and second tubes 652, 662. With the tubes 652, 662 positioned on the respective sleeves 602, the first and second bodies 654, 664 may be moved toward one another to compress the sleeves 602, and thereby the elongate members 30, toward one another. The ratchet design of the pawl tip 669 maintains the compressive force.

Figure 38:
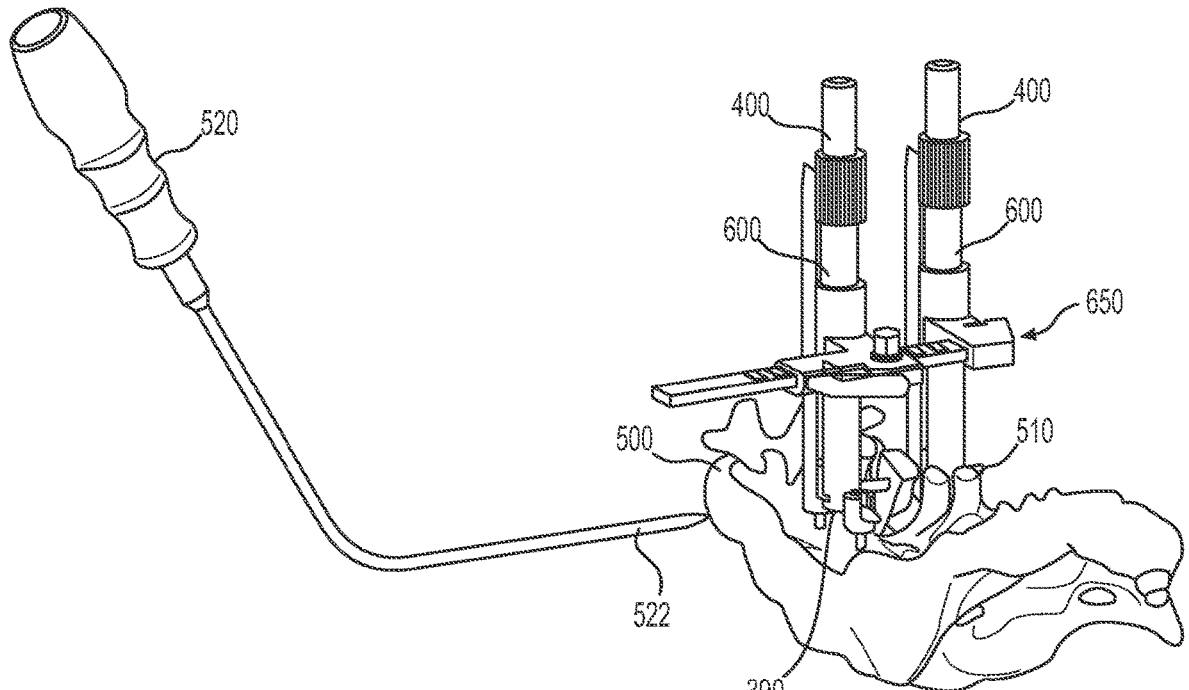
Figure 39:
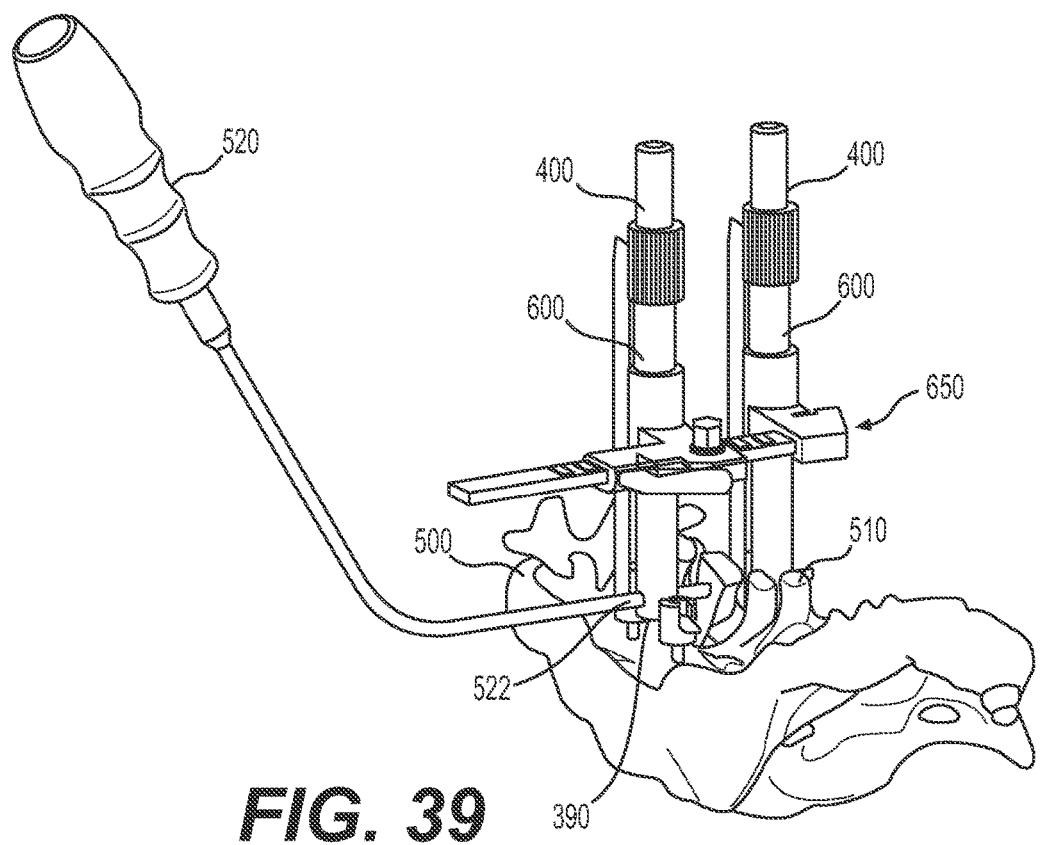

With the hook members 390 maintained in a desired position and orientation, an awl 520 or the like is extended into the surgical opening and through the openings 397 of the hook members 390, as illustrated in FIGS. 38-39. The awl 520 creates a path through various tissue, including ligaments and bone, for the connector member 180 to be inserted. For example, as illustrated in FIG. 27, in the final construct, the connector member 180 passes through a spinous process of a vertebra 510.

Figure 40:
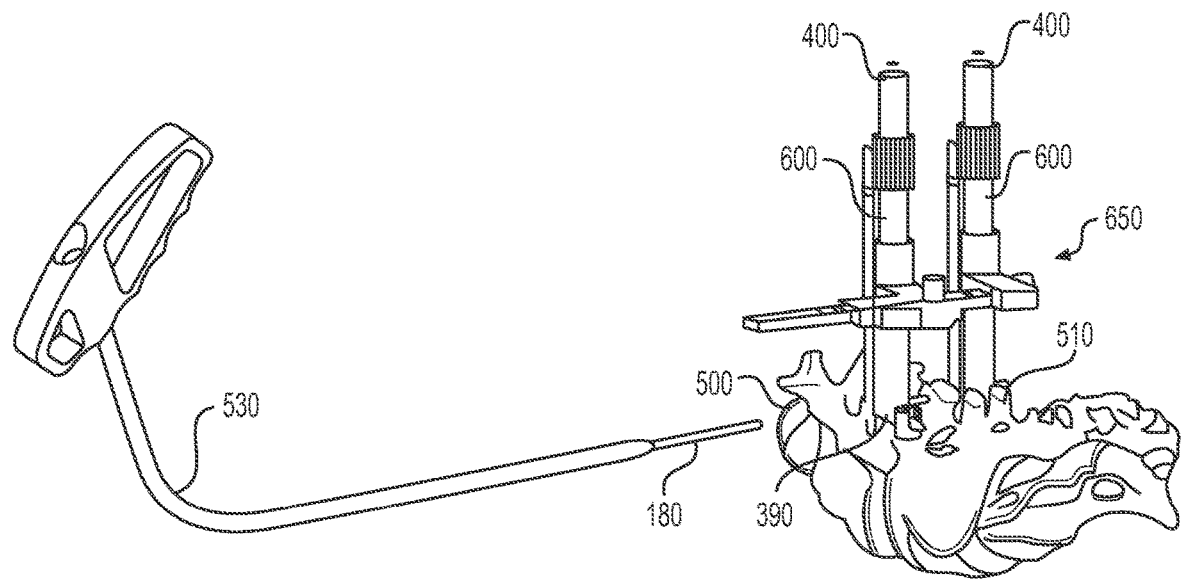
Figure 41:
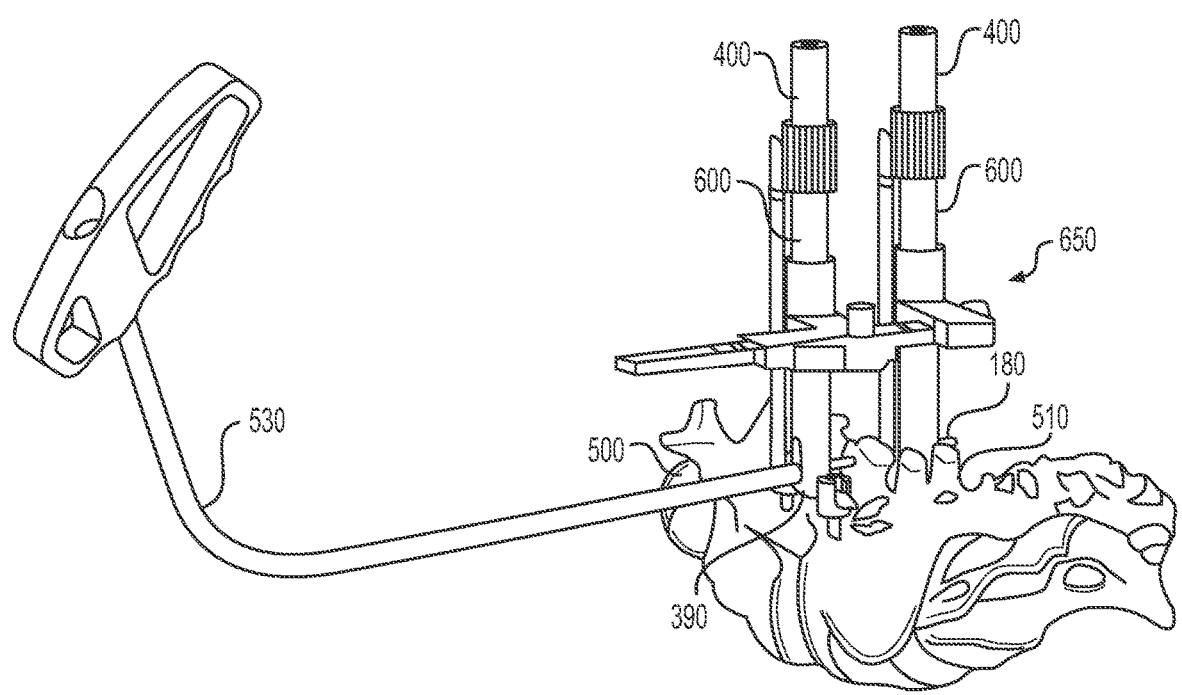

The awl 520 is removed and the connector member 180 is installed in the hook members 390 using, for example, the rod introduction instrument 530 to insert and position the connector member 180 in the hook members 390 (shown in FIGS. 40-41). In addition to the path created by the awl 520, the connector member 180 may include a frustoconical end which may further facilitate introduction of the connector member 180 through the various tissue including ligaments and bone.

Figure 42:
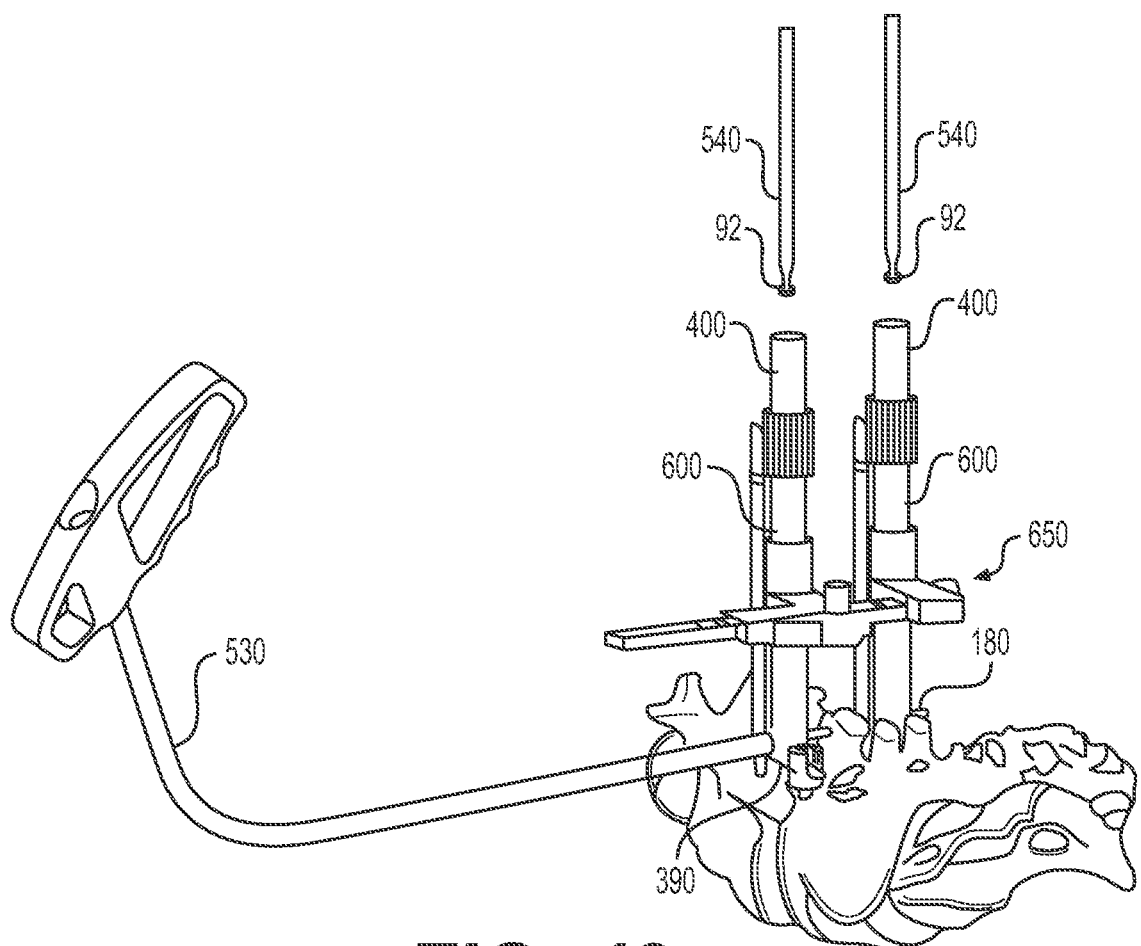
Figure 43:
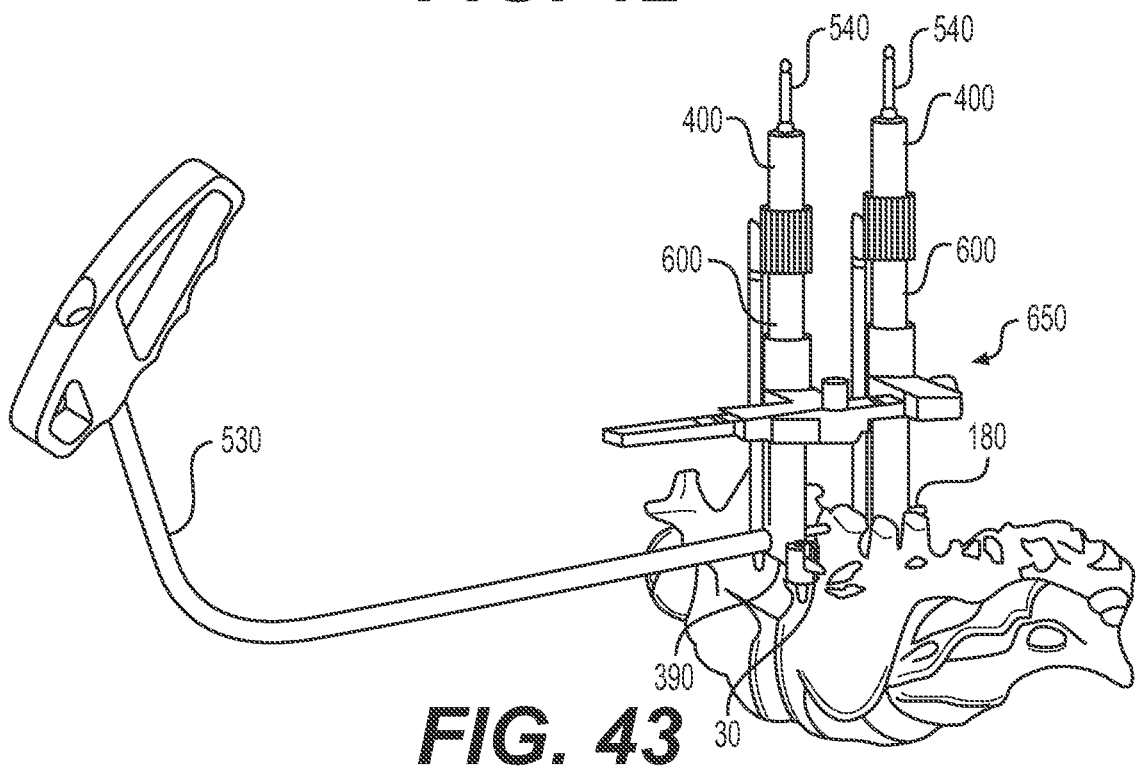

Once the connector member 180 is properly positioned in the hook members 390, fasteners 92 are installed in the hook members 390, as illustrated in FIGS. 42 and 43. Each fastener 92 is positioned on the tip of an insertion tool 540 and is then passed through an inner channel of the implant head inserter 400 so as to deliver the fastener 92 to the hook member 390 and install the fastener 92 into the hook member 390. Once the fasteners 92 are installed, the insertion tools 540, the compressor assembly 650, the sleeves 602 and the implant head inserters 400 may all be removed. The fasteners 92 secure the connector member 180 in the hook members 390 and the connector member 180 and hook members 390 to the elongate members 30 such that the final construct illustrated in FIG. 27 is achieved.

FIGS. 44-67 show another exemplary method of installing the bone fixation construct 10D, as illustrated in FIG. 27, in bone. In the present embodiment, two of couplers 40 have extenders 60 extending therefrom similar to the embodiment illustrated in FIG. 1.

Figure 44:
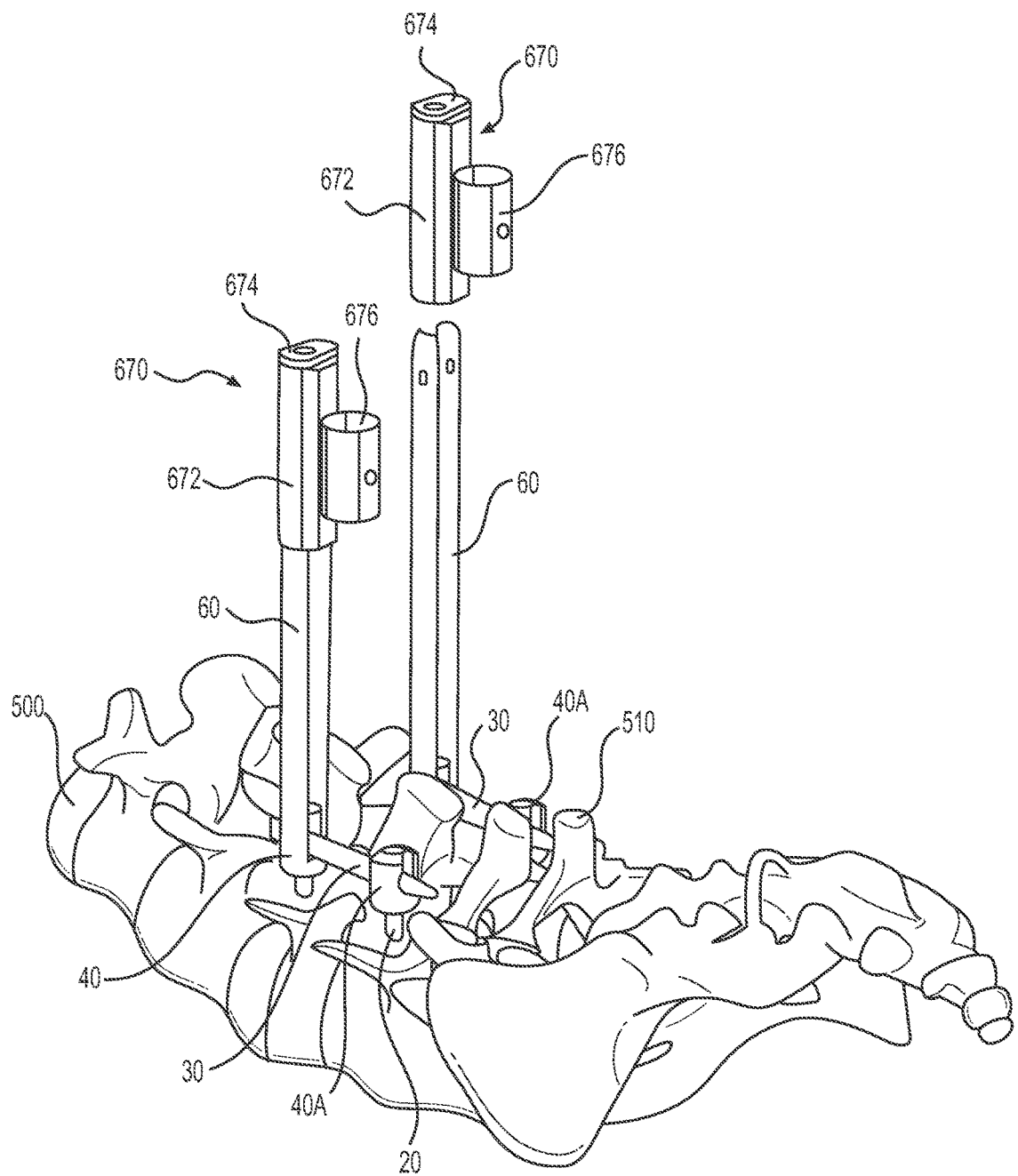
FIGS. 44-67 show yet another exemplary embodiment of a bone fixation construct during a process of installing the construct in bone.

Referring to FIG. 44, the bone screws 20, couplers 40, 40A, elongate members 30 and caps 50 are installed in a manner similar to that described above. In accordance with a non-limiting example of an installation process, as an initial step, an alignment clip 670 is positioned on each extender 60. Each alignment clip 670 includes a tubular body 672 configured to slidingly engage the respective extender 60. The proximal end of each tubular body 672 includes an inwardly extending shoulder 674 which acts as a stop to maintain the position of the tubular body 672 on the extender 60. An alignment tube 676 extends from each tubular body 672. While the illustrated alignment clip 670 has the alignment tube 676 in abutting relationship with the tubular body 672, the alignment tube 676 may be supported spaced away from the tubular body 672 to achieve a desired position of the hook member 390 along the elongate member 30.

Figure 45:
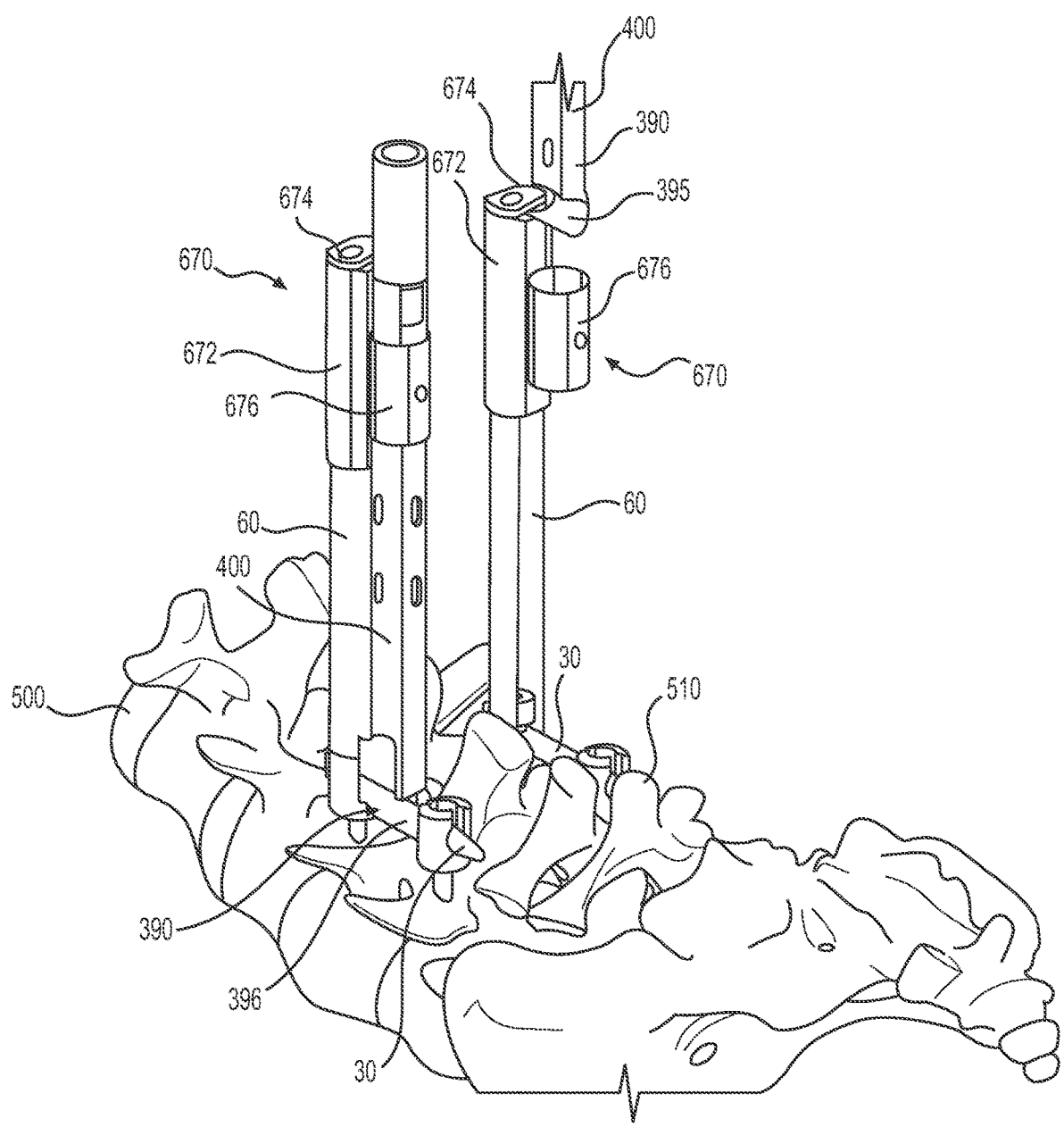

Similar to the previous embodiment, each of the hook members 390 is delivered to the site of the construct through a MIS opening, positioned proximate a predetermined portion of one of the elongate members 30, using an implant head inserter 400. In the present embodiment, each implant head inserter 400 is extended through a respective alignment tube 676, as illustrated in FIG. 45. The implant head inserters 400 are moved through the alignment tube 676 until the hook member 390 is positioned proximate to and then hooked onto the elongate member 30 such that the elongate member 30 is positioned completely within the receptacle 395. The alignment tubes 676 ensure that each implant head inserter 400 extends generally perpendicularly to the respective elongate member 30 with the hook member 390 in a generally desired position.

Figure 46:
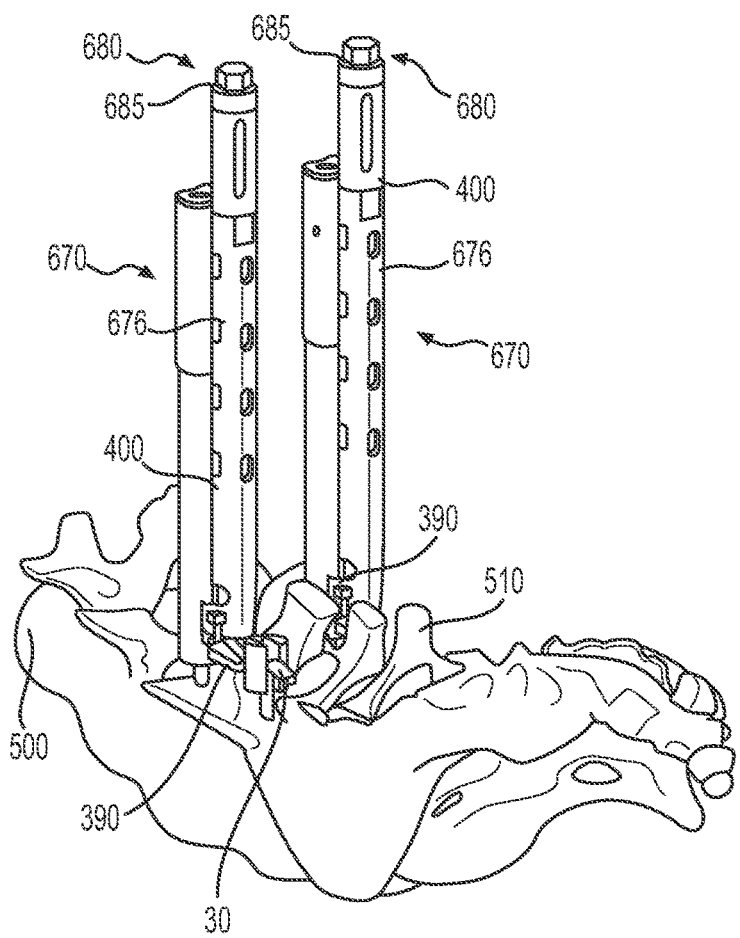
Figure 47:
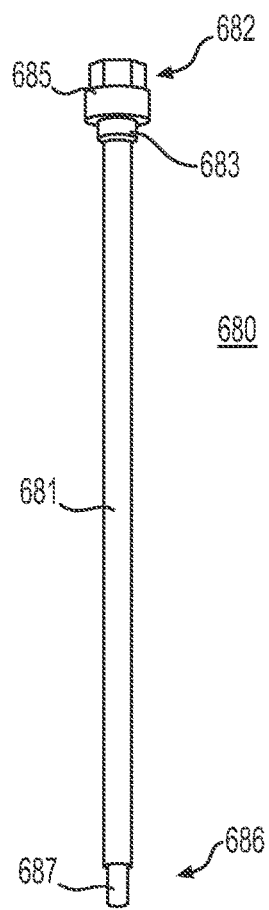
Figure 48:
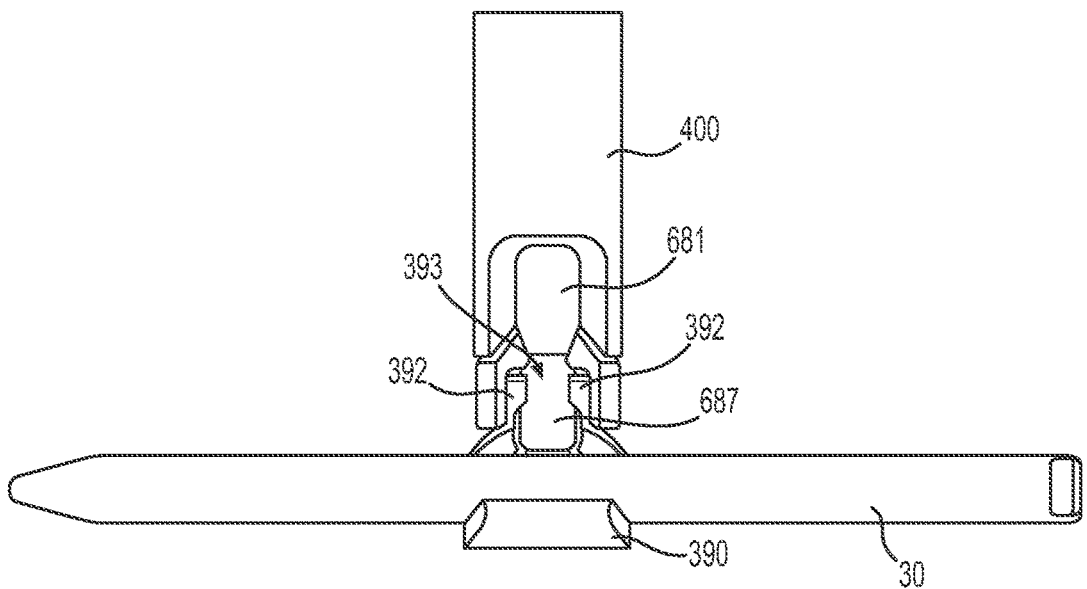
Figure 49:
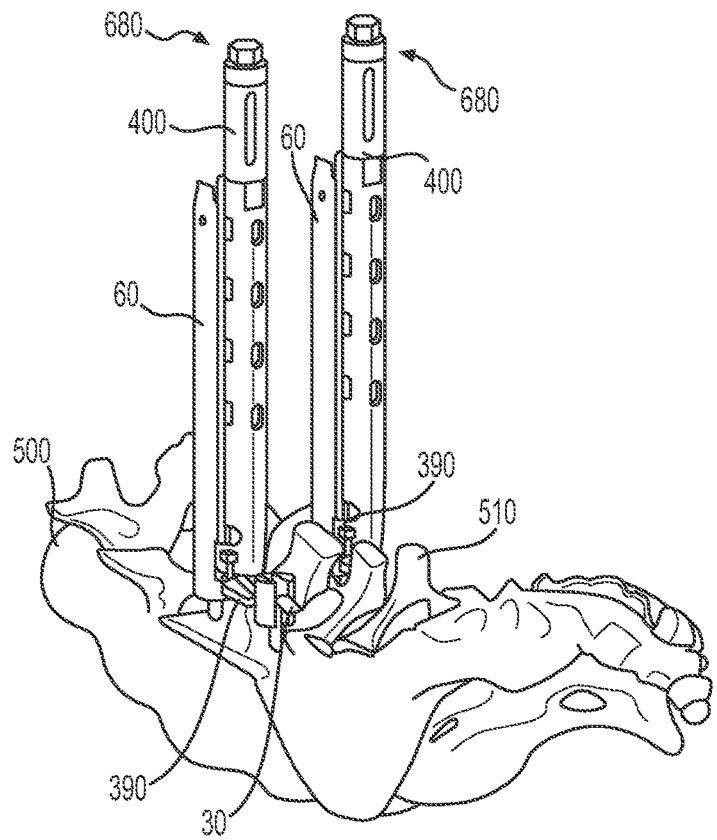

Referring to FIGS. 46-48, a preliminary locking instrument 680 is positioned relative to each implant head inserter 400 to temporarily maintain the position of the hook member 390 and prevent disengagement thereof from the respective elongate member 30. In the present embodiment, each preliminary locking instrument 680 includes an elongate shaft 681 extending from a proximal end 682 to a distal end 686. In the illustrated embodiment, the proximal end 682 includes a series of threads 683 and a fastener head 685 which facilitate securing the preliminary locking instrument 680 within a respective implant head inserter 400. The distal end 686 of the elongate shaft 681 includes a contact member 687. With the preliminary locking instrument 680 fully positioned within the implant head inserter 400, the contact member 687 engages the elongate member to retain the elongate member 30 within the receptacle 395. With the hook members 390 and implant head inserters 400 locked in position via the preliminary locking instruments 680, the alignment clips 670 may be removed as illustrated in FIG. 49.

Figure 50:
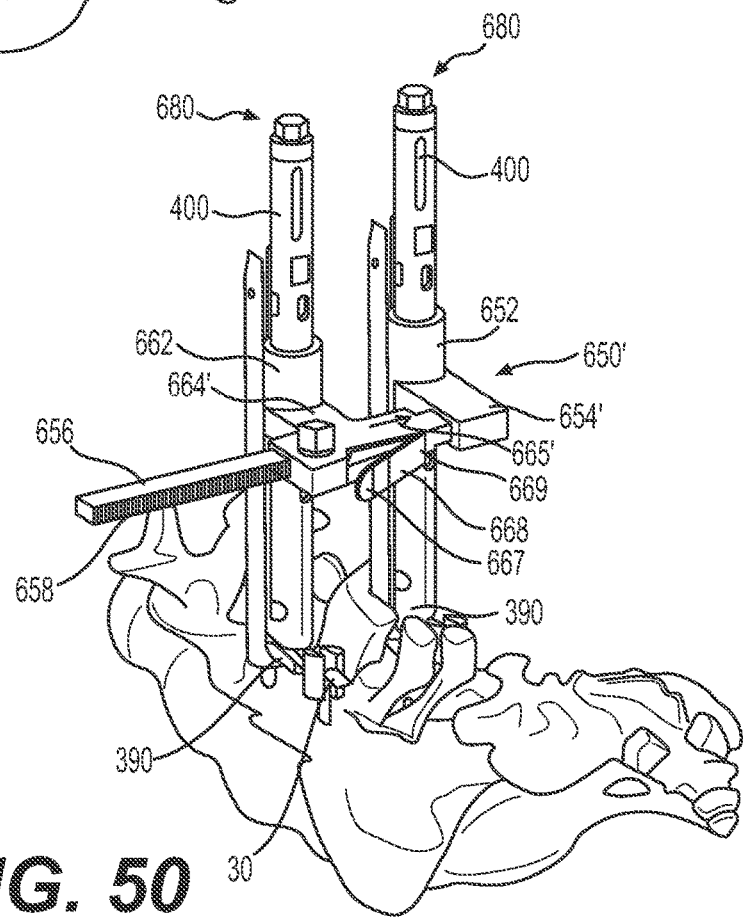
Figure 51:
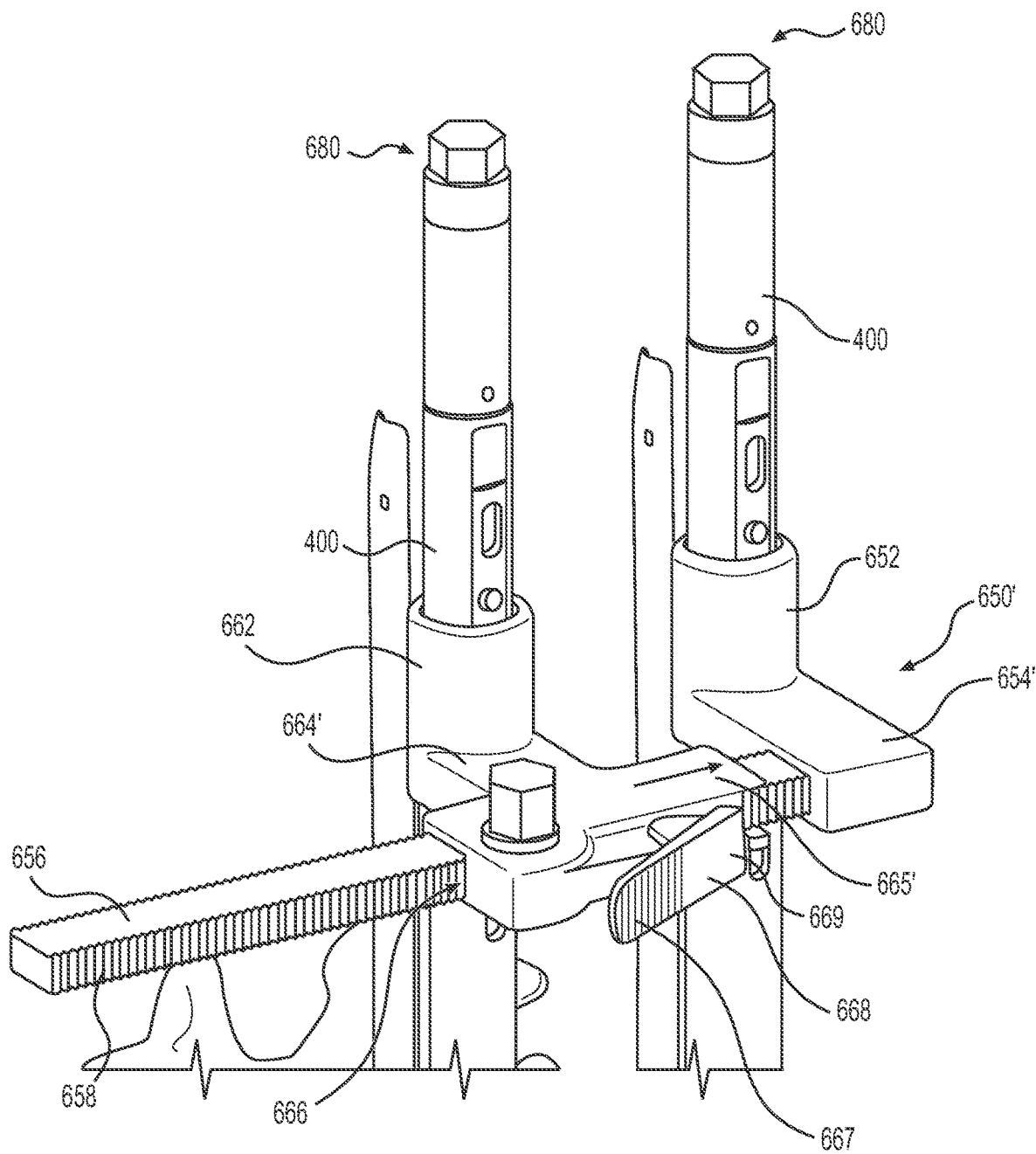
Figure 52:
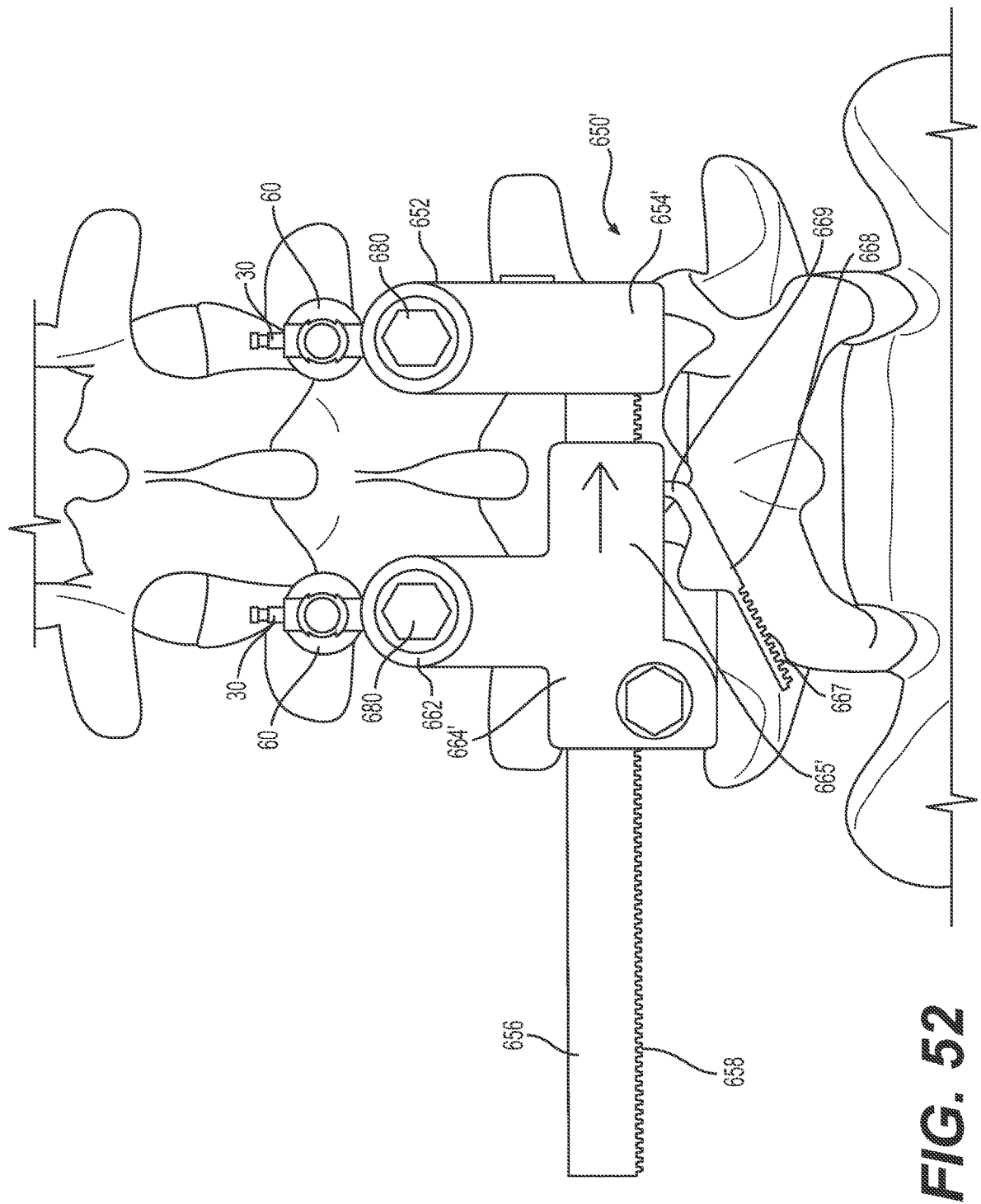

Turning to FIGS. 50-52, a compressor assembly 650' is positioned over the implant head inserters 400. The compressor assembly 650' is similar to the compressor assembly 650 and includes a first tube 652 configured to slide over a first of the inserters 400 and a second tube 662 configured to slide over the other inserter 400. In the present embodiment, the first tube 652 is fixedly connected to a first body 654'. The slide bar 656 extends from the first body 654' such that the first tube 652, the first body 654' and the slide bar 656 define a generally right angle. The slide bar 658 includes a series of teeth 658 defined along one edge thereof and configured to be engaged by a pivotal pawl 668 associated with the second tube 662, as will be described in more detail hereinafter.

Figure 53:
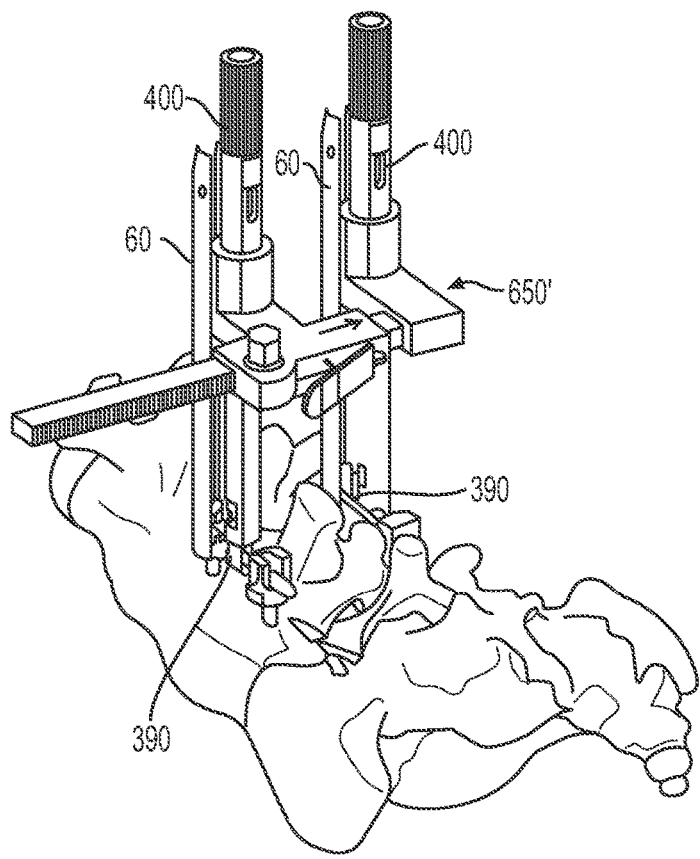
Figure 54:
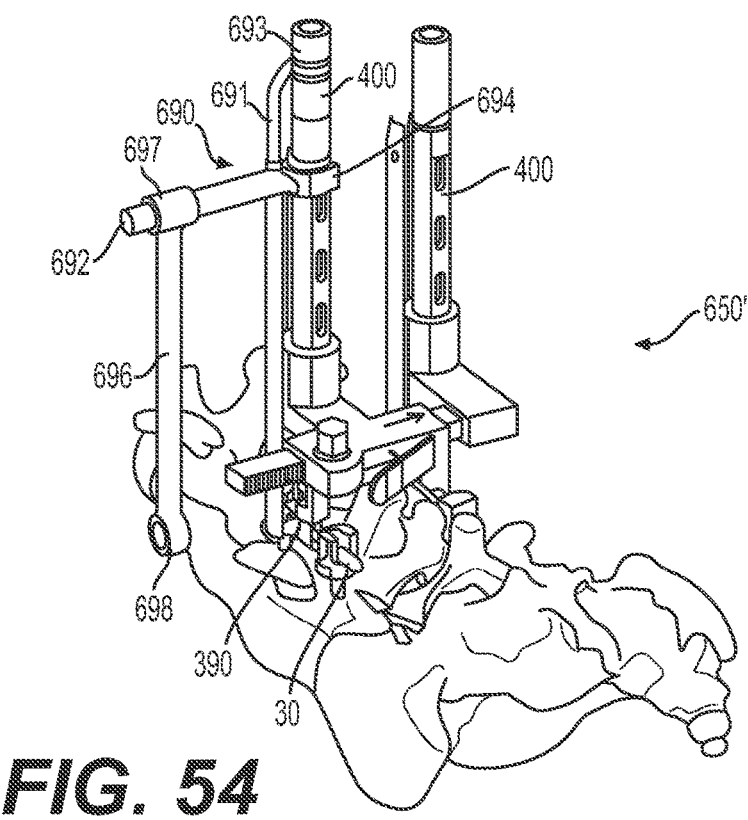
Figure 55:
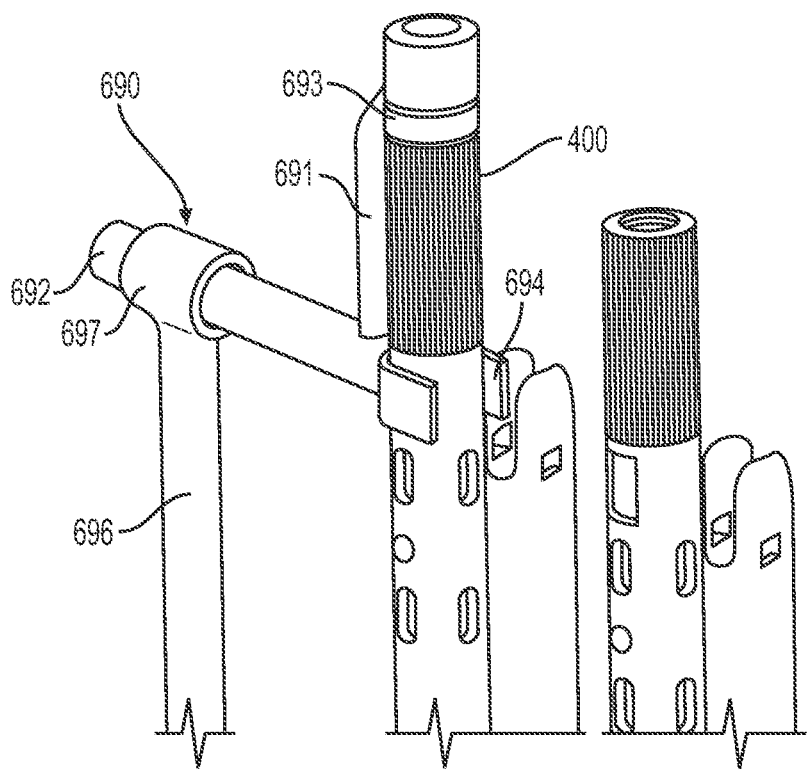
Figure 56:
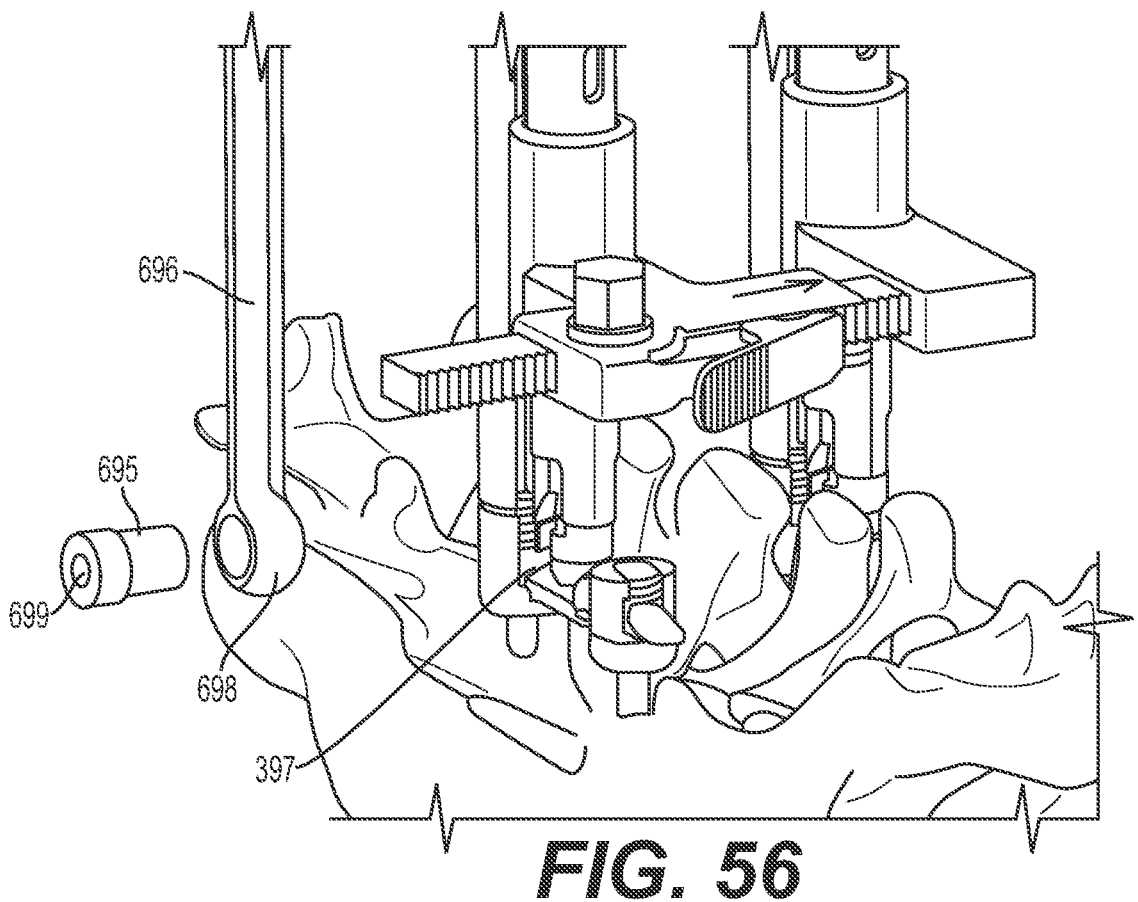
Figure 57:
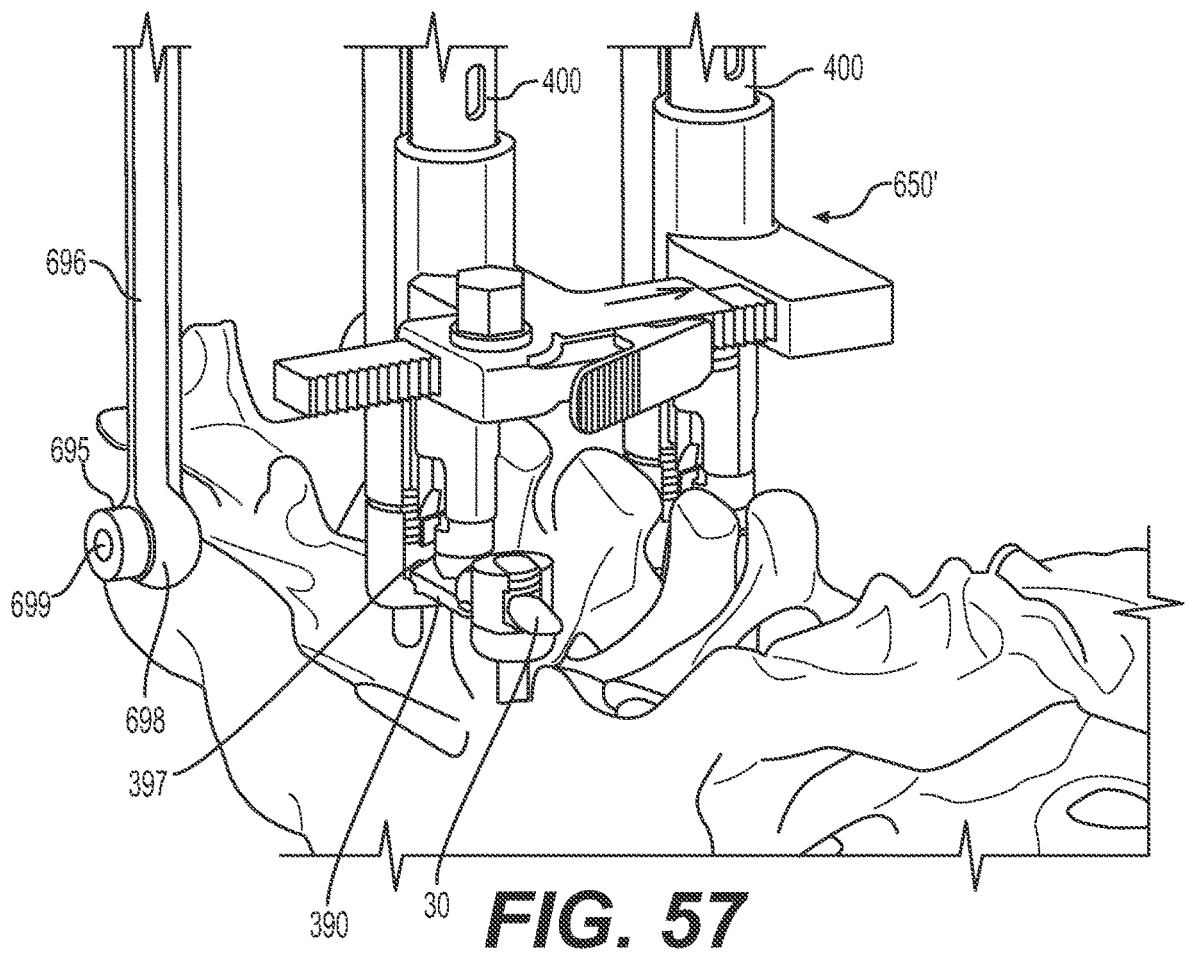

The second tube 662 has a second body 664' extending therefrom. The second body 664' includes a slide bar receiving portion 665' with a through opening 666 extending therethrough. The slide bar receiving portion 665' extends toward the first body 654' parallel to the slide bar 656 which extends through the opening 666. A pawl 668 is pivotally connected to the second body 664' and is biased such that a tip 669 of the pawl 668 is normally biased into engagement with the teeth 658 along the slide bar 656. An opposite end 667 of the pawl 668 may be pressed to disengage the tip 669 from the teeth 658. In the illustrated embodiment, the tip 669 is configured such that it may ratchet along the teeth 658 when the first and second tubes 652, 662 are moved toward one another, but remains engaged with the teeth 658 and prevents separation when a force is applied to separate the first and second tubes 652, 662. With the tubes 652, 662 positioned on the respective inserters 400, the first and second bodies 654', 664' may be moved toward one another to compress the inserters 400, and thereby the elongate members 30, toward one another, as illustrated in FIGS. 51 and 52. The ratchet design of the pawl tip 669 maintains the compressive force. With the hook members 390 maintained in a desired position and orientation, the preliminary locking instruments 680 may be removed as illustrated in FIG. 53.

Turning to FIGS. 53-57, with the compressor assembly 650' in position, an alignment assembly 690 is positioned on one of the implant head inserters 400. The alignment assembly 690 includes an extending bar 692 which includes a clip 694 at one end which engages the implant head inserter 400. A support arm 691 may extend between the extending bar 692 and a cap 693 secured into the inserter 400 to further support the extending bar 692. An alignment bar 696 depends from the extending bar 692 at junction 697. The junction 697 may be a fixed connection or may be slightly adjustable to provide alignment adjustment. The free end of the alignment bar 696 includes an alignment ring 698 with a through opening. With the extending bar 692 and alignment bar 696 in position, the through opening of the alignment ring 698 is preferably co-axial with the openings 397 of the hook members 390. In the illustrated embodiment, a bushing 695 may be positioned in the through opening of the alignment ring 698 to define a small opening 699 which is also co-axial with the openings 397 of the hook members 390.

Figure 58:
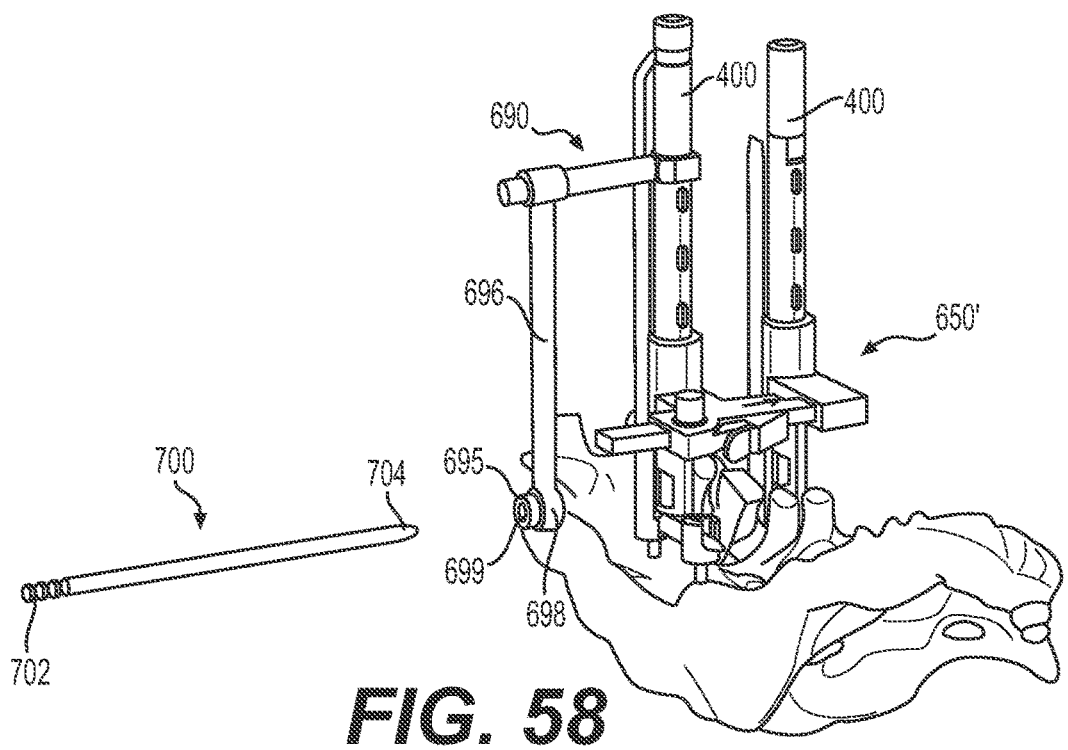
Figure 59:
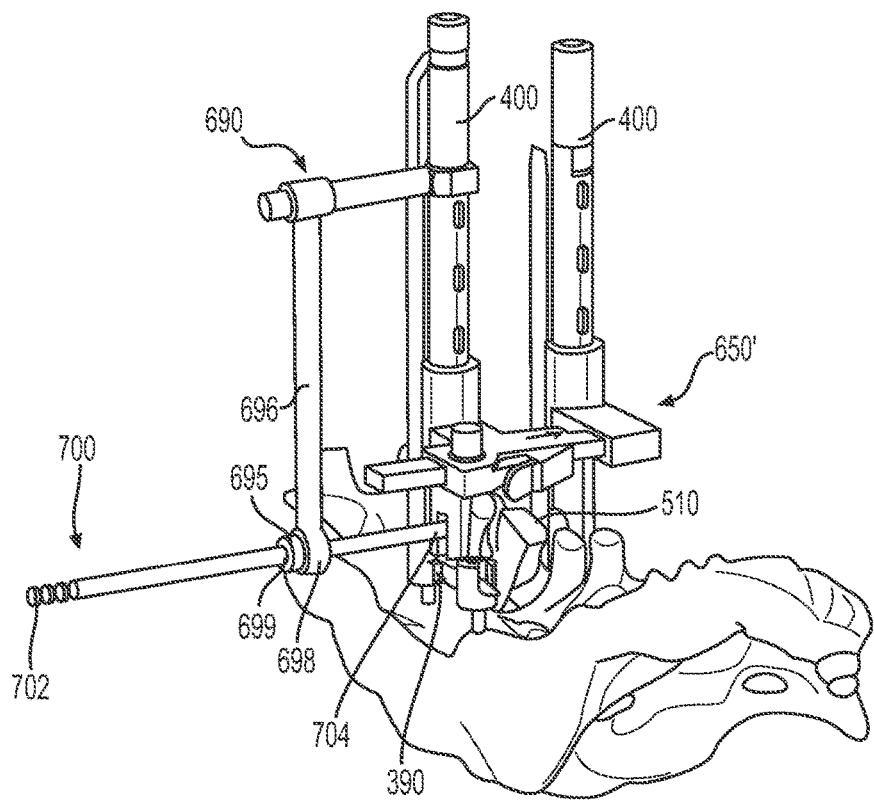

Referring to FIGS. 58-59, the opening 699 of the bushing 695 is configured to guide a first dilator 700 toward the openings 397 in the hook members 390. The first dilator 700 extends from a proximal end 702 to a pointed distal end 704. The first dilator 700 is advanced through the opening 699 and partially into the opening 397 of the first hook member 390. With the first dilator 700 so positioned, an aligned path is established between the alignment ring 698 and the opening 397 of the hook member 390.

Figure 60:
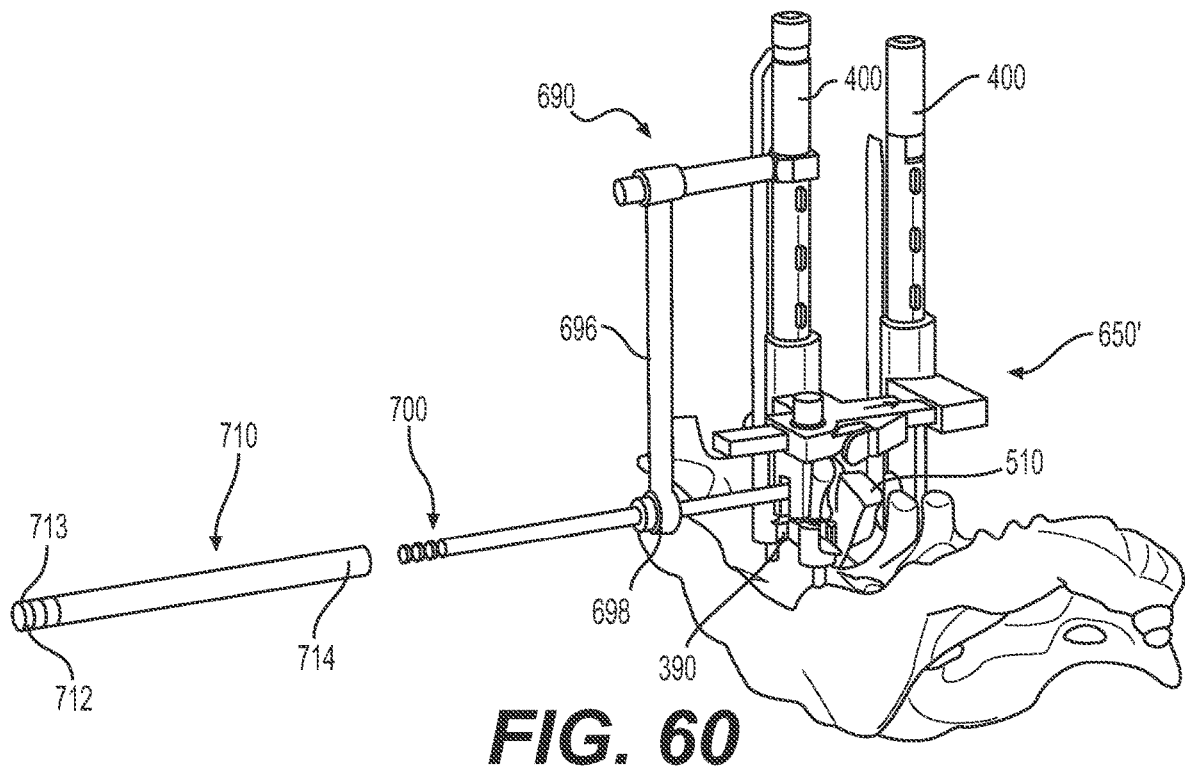
Figure 61:
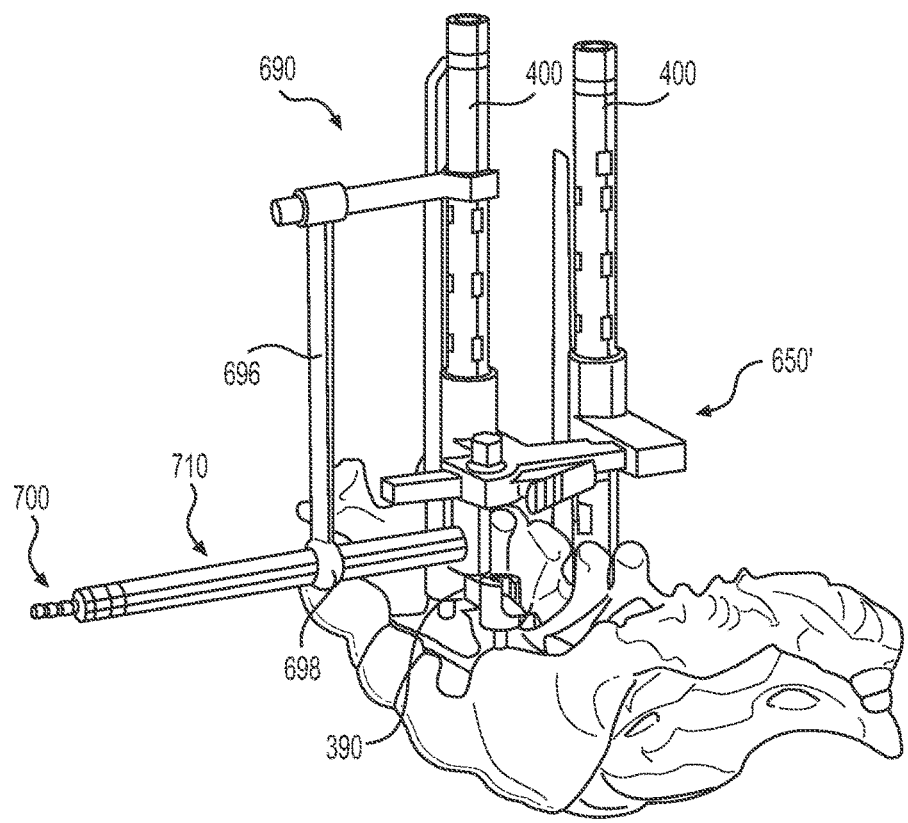

After the first dilator 700 has been positioned, the bushing 695 is removed and a second, larger dilator 710 is aligned to be slid over the first dilator 700, as illustrated in FIG. 60. The second dilator 710 extends from a proximal end 712 to a distal end 714 with a passage 713 therethrough. The passage 713 is sized such that the second dilator 710 slides over the first dilator 700. The second dilator 710 has an outside diameter configured to pass through the through opening of the alignment ring 698. The second dilator 710 is advanced until it contacts the first hook member 390, as illustrated in FIG. 61. With the second dilator 710 so positioned, an aligned passage 713 is established between the alignment ring 698 and the opening 397 of the hook member 390. The first dilator 700 may then be removed, with the aligned passage 713 remaining.

Figure 62:
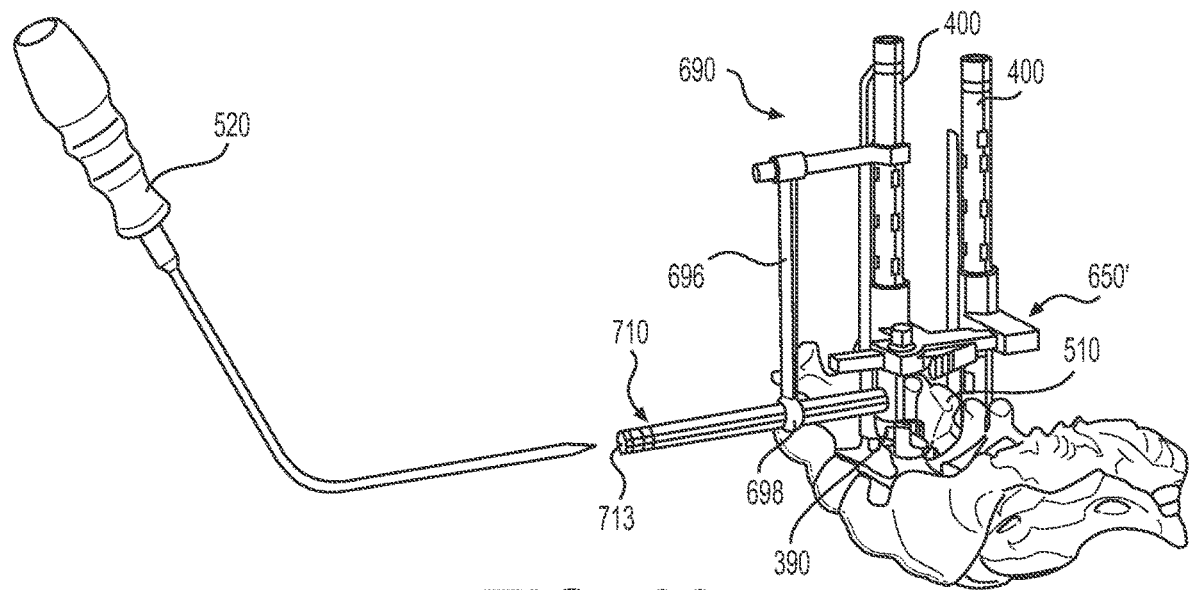
Figure 63:
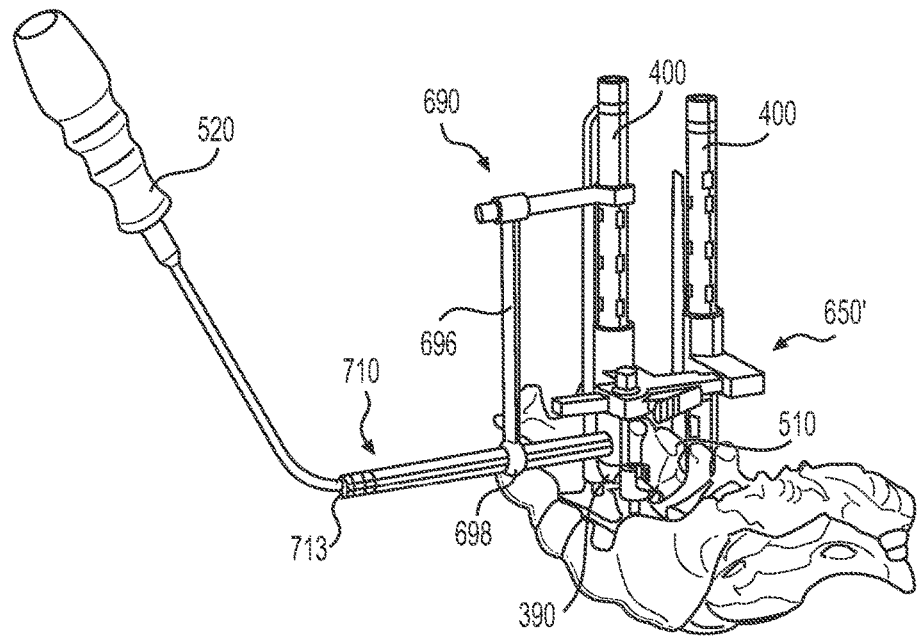

Referring to FIGS. 62-63, an awl 520 or the like is extended into the surgical opening and through the passage 713. The alignment assembly 690 and dilator 710 ensure that the awl 520 is properly directed through the openings 397 of the hook members 390 and various tissue, including ligaments and bone, of the vertebrae 510. The awl 520 thereby produces a proper path for the connector member 180 to be inserted. For example, as illustrated in FIG. 27, in the final construct, the connector member 180 passes through a spinous process of a vertebra 510.

Figure 64:
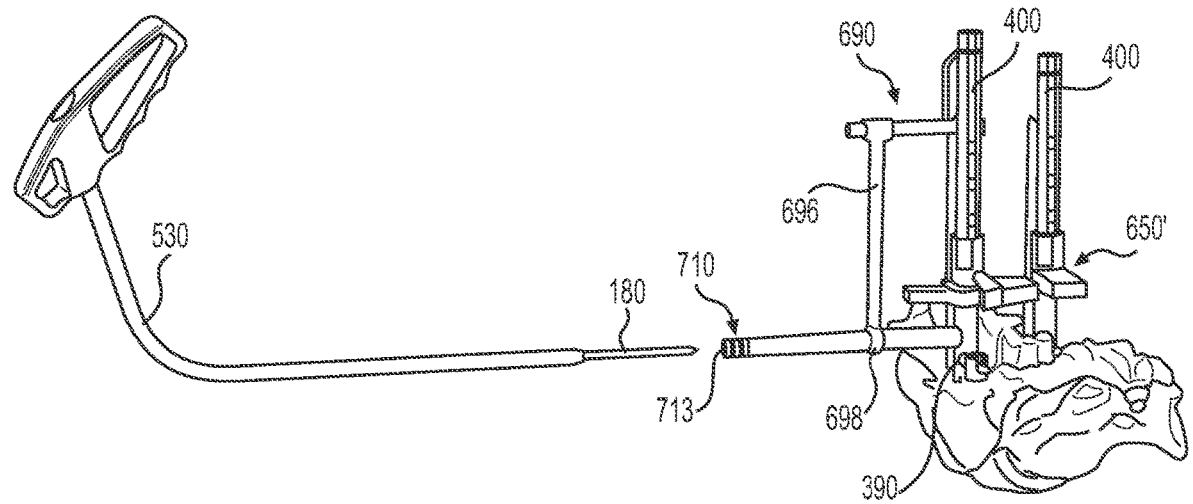
Figure 65:
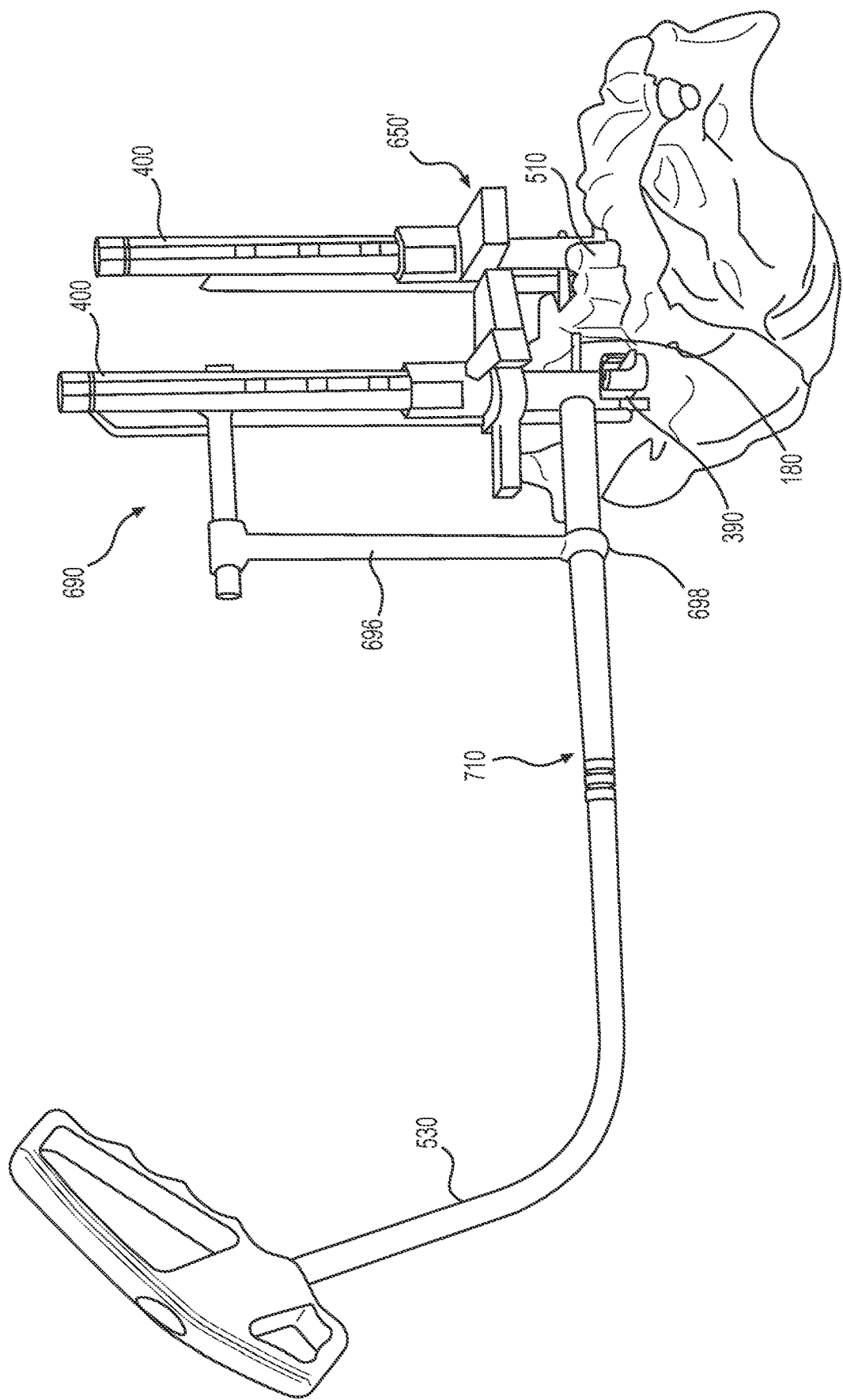

The awl 520 is removed and the connector member 180 is installed in the hook members 390 using, for example, the rod introduction instrument 530 to insert and position the connector member 180 in the hook members 390 (shown in FIGS. 64-65). In addition to the path created by the awl 520, the connector member 180 may include a frustoconical end which may further facilitate introduction of the connector member 180 through the various tissue including ligaments and bone.

Figure 66:
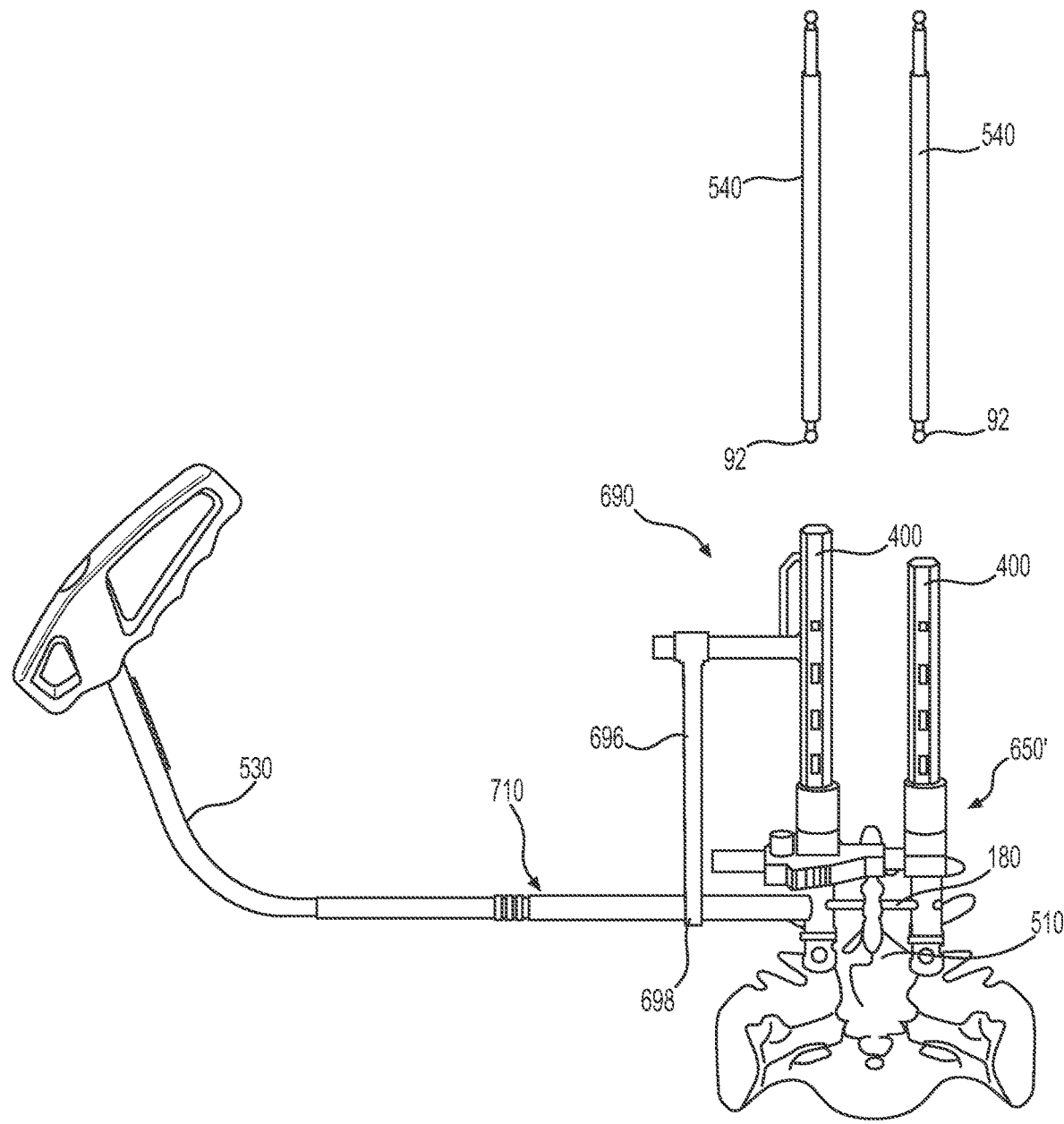
Figure 67:
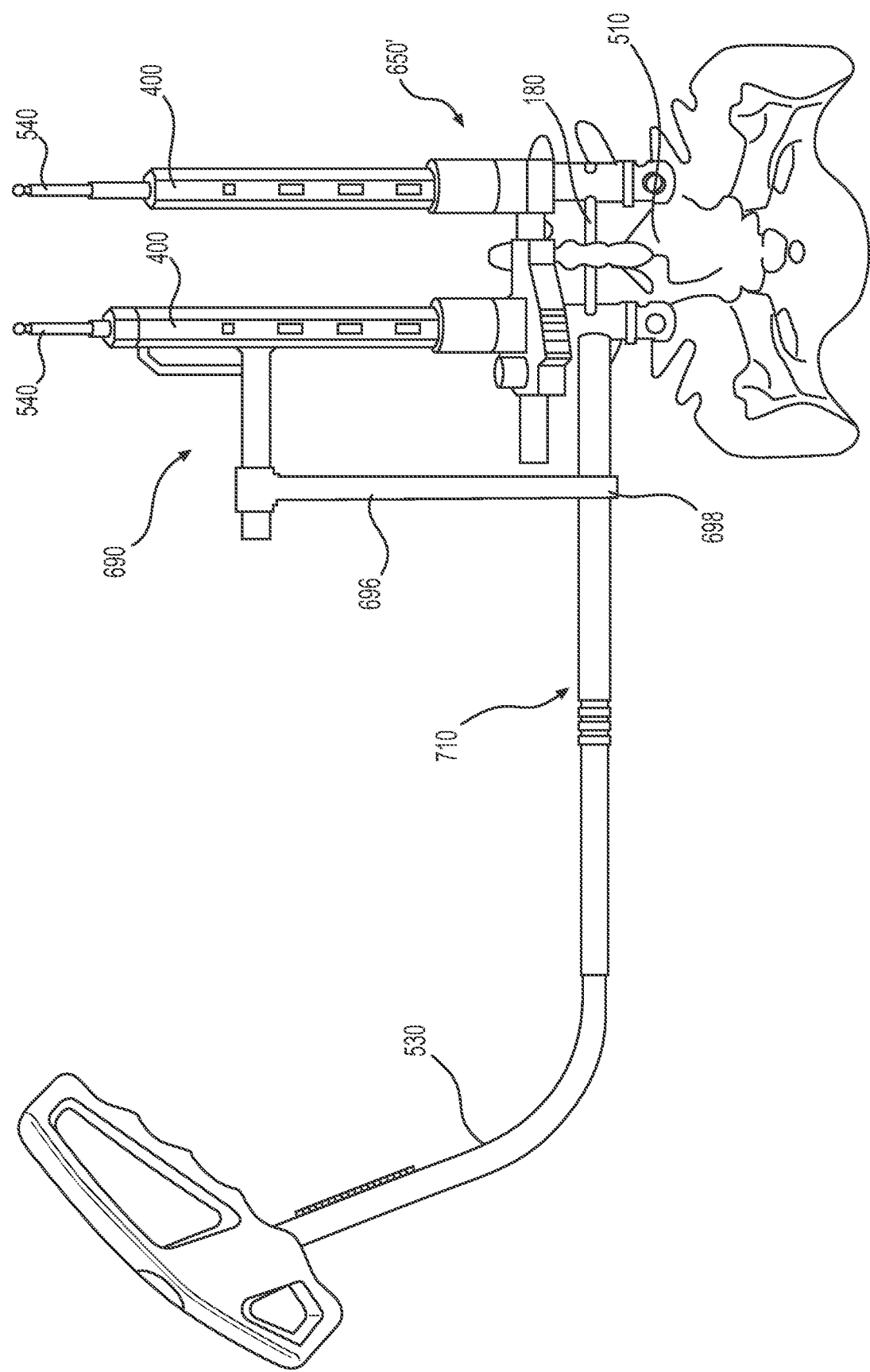

Once the connector member 180 is properly positioned in the hook members 390, fasteners 92 are installed in the hook members 390, as illustrated in FIGS. 66 and 67. Each fastener 92 is positioned on the tip of an insertion tool 540 and is then passed through an inner channel of the implant head inserter 400 so as to deliver the fastener 92 to the hook member 390 and install the fastener 92 into the hook member 390. Once the fasteners 92 are installed, the insertion tools 540, the compressor assembly 650' and the implant head inserters 400 may all be removed. The fasteners 92 secure the connector member 180 in the hook members 390 and the connector member 180 and hook members 390 to the elongate members 30 such that the final construct illustrated in FIG. 27 is achieved.

The terms "including," "comprising," and variations thereof, as used in this disclosure, mean "including, but not limited to," unless expressly specified otherwise.

The terms "a," "an," and "the," as used in this disclosure, means "one or more," unless expressly specified otherwise.

Devices that are in communication with each other need not be in continuous communication with each other, unless expressly specified otherwise. In addition, devices that are in communication with each other may communicate directly or indirectly through one or more intermediaries.

Although process steps, method steps, or the like, may be described in a sequential order, such processes and methods be configured to work in alternate orders. In other words, any sequence or order of steps that may be described does not necessarily indicate a requirement that the steps be performed in that order. The steps of the processes or methods described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

While the disclosure has been described in terms of exemplary embodiments, those skilled in the art will recognize that the disclosure can be practiced with modifications in the spirit and scope of the appended claims. These examples are merely illustrative and are not meant to be an exhaustive list of all possible designs, embodiments, applications or modifications of the disclosure.

What is claimed is:

1. A bone fixation system for implanting in bone, comprising:
   at least one bone fastener assembly configured to attach to bone;
   an elongate member configured to attach to each bone fastener;
   a connector member configured to engage the elongate member;
   a hook member configured to engage the elongate member and the connector member, wherein the hook member comprises a hook member body having a first opening formed between a pair of upwardly extending arms, a receptacle, a hook portion, and a second opening;
   an elongate implant head inserter having a distal tip configured to attach to the hook member;
   an elongate temporary locking instrument configured to slide over and around the implant head inserter and having a distal tip adapted to temporarily prevent the hook member from disengaging from the elongate member, and
   wherein the hook member body is configured to taper to the pair of upwardly extending arms to be received in the implant head inserter.

2. The bone fixation system of claim 1, wherein each bone fastener assembly comprises:
   a bone fastener configured to attach to bone;
   a coupler that connects to the bone fastener; and
   an extender that connects to the coupler.

3. The bone fixation system of claim 2, wherein the extender comprises:
   a coupling portion that attaches to the coupler; and
   a blade portion that attaches to the coupling portion.

4. The bone fixation system of claim 3, wherein coupling portion comprises a threading.

5. The bone fixation system of claim 3, wherein the blade portion comprises a pair of extender blades.

6. The bone fixation system of claim 3, wherein the hook member comprises a hook fastener.

7. The bone fixation system of claim 6, wherein the hook fastener secures the connector member to the hook member.

8. The bone fixation system of claim 7, wherein the hook fastener secures the hook member and the connector member to the elongate member.

9. The bone fixation system of claim 1, wherein the distal tip of the temporary locking instrument includes a plurality of fingers circumferentially spaced from one another.

10. The bone fixation system of claim 9, wherein when the temporary locking instrument is fully advanced into the implant head inserter, the fingers extend on opposed sides of the elongate member.

11. A bone fixation system for implanting in bone, comprising:
    a connector member that contacts a pair of elongate members; and
    a hook member configured to engage one of the elongate members and the connector member, wherein the hook member comprises a hook member body having a first opening formed between a pair of upwardly extending arms, a receptacle, a hook portion, and a second opening,
    an elongate implant head inserter having a distal tip configured to attach to the hook member;
    an elongate temporary locking instrument configured to slide over and around the implant head inserter and having a distal tip adapted to temporarily prevent the hook member from disengaging from the elongate member, and
    wherein the hook member body is configured to taper to the pair of upwardly extending arms to be received in the implant head inserter.

12. The bone fixation system of claim 11, further comprising a plurality of bone fastener assemblies.

13. The bone fixation system of claim 12, wherein each bone fastener assembly comprises:
    a bone fastener configured to attach to bone;
    a coupler that connects to the bone fastener; and
    an extender that connects to the coupler.

14. The bone fixation system of claim 13, wherein the extender comprises:
    a coupling portion that attaches to the coupler; and
    a blade portion that attaches to the coupling portion.

15. The bone fixation system of claim 14, wherein the coupling portion comprises a threading.

16. The bone fixation system of claim 15, wherein the blade portion comprises a pair of extender blades.

17. A bone fixation system for implanting in bone, comprising:

a plurality of bone fasteners configured to attach to bone;
a plurality of couplers that connect to the plurality of bone fasteners;
a plurality of extenders that connect to the plurality of couplers;
a pair of elongate members that attach to the plurality of bone fastener assemblies;
a connector member that contacts the pair of elongate members; and
a hook member configured to engage one of the elongate members and the connector member, wherein the hook member comprises a hook member body having a first opening formed between a pair of upwardly extending arms, a receptacle, a hook portion, and a second opening,
an elongate implant head inserter having a distal tip configured to attach to the hook member;
an elongate temporary locking instrument configured to slide over and around the implant head inserter and having a distal tip adapted to temporarily prevent the hook member from disengaging from the elongate member, and
wherein the hook member body is configured to taper to the pair of upwardly extending arms to be received in the implant head inserter.

18. The bone fixation system of claim 17, wherein the hook member comprises a hook fastener.

19. The bone fixation system of claim 18, wherein the hook fastener secures the connector member to the hook member.

20. The bone fixation system of claim 19, wherein the hook fastener secures the hook member and the connector member to the elongate member.

* * * * *